(12) United States Patent
Krivoruchko et al.

(10) Patent No.: US 11,692,209 B2
(45) Date of Patent: Jul. 4, 2023

(54) GENETICALLY MODIFIED FUNGAL CELLS FOR OVEREXPRESSION OF AN ACETYL-COA CARBOXYLASE AND A PYRUVATE CARBOXYLASE

(71) Applicant: Melt&Marble AB, Gothenburg (SE)

(72) Inventors: Anastasia Krivoruchko, Gothenburg (SE); Jens Nielsen, Hellerup (DK); Florian David, Gothenburg (SE); Tao Yu, Shenzhen (CN)

(73) Assignee: MELT&MARBLE AB, Gothenburg (SE)

(*) Notice: Subject to any disclaimer, the term of this patent is extended or adjusted under 35 U.S.C. 154(b) by 0 days.

(21) Appl. No.: 16/830,854

(22) Filed: Mar. 26, 2020

(65) Prior Publication Data
US 2021/0095319 A1    Apr. 1, 2021

Related U.S. Application Data

(60) Provisional application No. 62/824,398, filed on Mar. 27, 2019.

(51) Int. Cl.
| | | |
|---|---|---|
| *C12P 7/6409* | (2022.01) | |
| *C12N 1/16* | (2006.01) | |
| *C12N 9/00* | (2006.01) | |

(52) U.S. Cl.
CPC .......... *C12P 7/6409* (2013.01); *C12N 1/16* (2013.01); *C12N 9/93* (2013.01); *C12Y 604/01001* (2013.01); *C12Y 604/01002* (2013.01)

(58) Field of Classification Search
None
See application file for complete search history.

(56) References Cited

U.S. PATENT DOCUMENTS

| | | | | |
|---|---|---|---|---|
| 10,533,198 B2* | 1/2020 | Nielsen | .................. | C12N 15/81 |
| 11,162,119 B2* | 11/2021 | Nielsen | .................. | C12P 7/649 |
| 2004/0214306 A1* | 10/2004 | Bloom | .................. | C12N 1/205 |
| | | | | 435/252.33 |
| 2011/0125118 A1* | 5/2011 | Lynch | ...................... | C12N 1/20 |
| | | | | 604/367 |
| 2011/0223641 A1* | 9/2011 | Stephanopoulos | .. | C12N 15/815 |
| | | | | 435/134 |
| 2016/0215308 A1* | 7/2016 | Runguphan | ............ | C12N 15/81 |
| 2016/0237441 A1* | 8/2016 | Nielsen | ................ | C12N 9/1029 |

FOREIGN PATENT DOCUMENTS

| | | | | |
|---|---|---|---|---|
| CN | 107164254 A | * | 9/2017 | |
| WO | WO-2014016328 A1 | * | 1/2014 | ............... C12N 9/16 |
| WO | WO-2016159869 A1 | * | 10/2016 | ................ C12P 7/04 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Accession Q00955. Apr. 1, 1993 (Year: 1993).*
Accession P11154. Jul. 1, 1989 (Year: 1989).*
Accession Q5BAJ4. Apr. 26, 2005 (Year: 2005).*
Accession P38225. Oct. 1, 1994 (Year: 1994).*
CN107164254A. Machine translation in English. Sep. 15, 2017 (Year: 2017).*
Pfleger, Brian F. et al., Metabolic engineering strategies for microbial synthesis of oleochemicals, Metabolic Engineering, vol. 29, pp. 1-50 (2015).
Yu, Tao et al., Reprogramming Yeast Metabolism from Alcoholic Fermentation to Lipogenesis, Cell, vol. 174, pp. 1549-1558 (Sep. 6, 2018).

* cited by examiner

*Primary Examiner* — Christian L Fronda
(74) *Attorney, Agent, or Firm* — Porter Wright Morris & Arthur LLP

(57) ABSTRACT

A fungal cell is capable of producing high levels of fatty acids and fatty acid-derived products. The fungal cell comprises at least one modification to the endogenous fatty acid metabolism.

24 Claims, 17 Drawing Sheets
Specification includes a Sequence Listing.

Fig. 5A
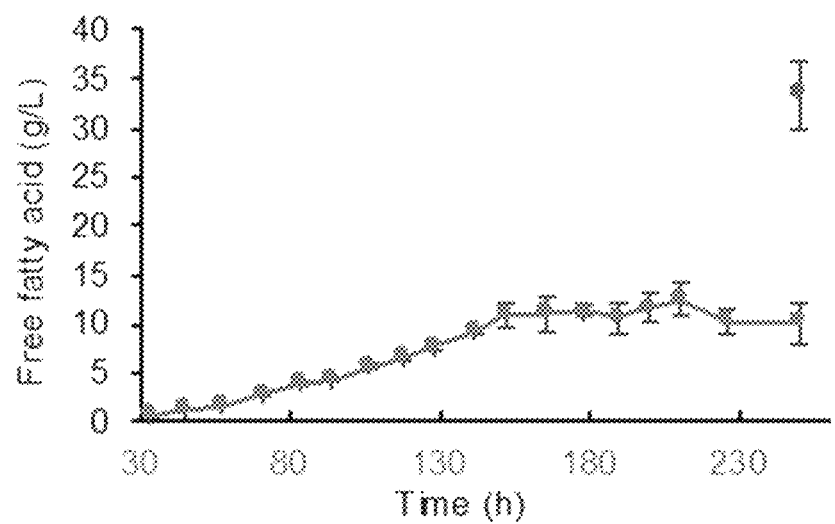
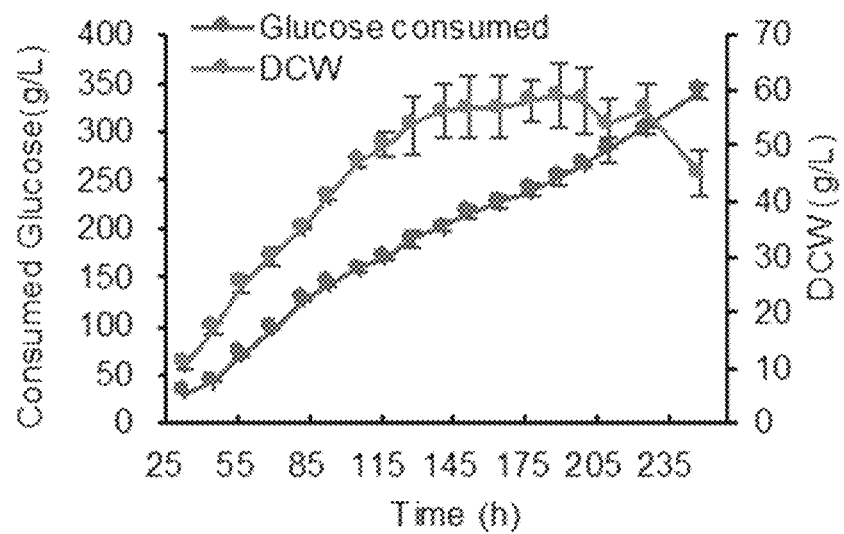
Fig. 5B

GENETICALLY MODIFIED FUNGAL CELLS FOR OVEREXPRESSION OF AN ACETYL-COA CARBOXYLASE AND A PYRUVATE CARBOXYLASE

CROSS-REFERENCE TO RELATED APPLICATION

This application is based on and claims priority to U.S. Provisional application No. 62/824,398, filed on Mar. 27, 2019, in the U.S. Patent and Trademark Office, the entire contents thereof are incorporated herein by reference.

The Sequence Listing submitted herewith, entitled "Dec. 11-2020-Sequence-Listing.txt", created Dec. 11, 2020 and having a size of 128,207 bytes, is incorporated herein by reference.

TECHNICAL FIELD

The present invention relates generally to the development of genetically engineered microorganisms. More specifically, the invention relates to fungal cells able to produce fatty acids and/or fatty acid-derived products in an economic fashion.

BACKGROUND

Fatty acids are carboxylic acids with a long aliphatic chain that is either saturated or unsaturated. Fatty acids and their derived products, e.g., fatty alcohols, fatty acid esters, etc., have numerous commercial applications including as surfactants, lubricants, plasticizers, solvents, emulsifiers, emollients, thickeners, flavors, pesticides, cosmetics, nutraceuticals and fuels. Current technologies for producing fatty acids and fatty acid-derived products are typically via extraction from plant or animal sources, such as coconut, palm, palm kernel, tallow and lard. However, due to concerns regarding the sustainability of these sources, as well as increasing demands for specialty fatty acids that cannot be easily derived from natural sources, alternative production methods are needed. For example, research efforts have focused on production of fatty acids via microbial fermentation (Pfleger et al., 2015). In addition, recent advances in genetic and metabolic engineering have allowed for precise manipulation of the microbial metabolism to produce tailor-made products. Other advantages of these production platforms include environmental friendliness, scalability, geographical independence, and cost effectiveness. Microbial fatty acid biosynthesis has attracted much attention for production of oleochemicals and biofuels. Engineering of central metabolism and fatty acid biosynthesis enabled fatty acid overproduction in *Escherichia coli, Saccharomyces cerevisiae*, and *Yarrowia lipolytica*. However, the production titer and yield need to be further enhanced to enable industrial production using new strategies.

There is therefore still a need for techniques for the production of fatty acids and/or fatty acid-derived products in yeast cells in an efficient way.

SUMMARY

It is a general objective to provide improved production of fatty acids and/or fatty acid-derived products in fungal cells.

The present invention provides a genetically engineered fungal cell, preferably a yeast cell, which comprises genetic modifications that allow increased production of fatty acids and/or fatty acid-derived products. The fungal cell is genetically modified for overexpression of an acetyl-CoA carboxylase and a pyruvate carboxylase.

The yeast *Saccharomyces cerevisiae* is a very important cell factory as it is already widely used for production of biofuels, chemicals and pharmaceuticals, and there is therefore much interest in developing platform strains of this yeast that can be used for production of a whole range of different products. It is, however, a problem that such a platform cell factory for efficient production of fatty acids and fatty acid-derived products is not as efficient as needed for good industrial application. This invention involves a multiple gene modification approach of the yeast to generate a stable and scalable platform for production fatty acids and fatty acid-derived products.

The present invention relates to a fungal cell and methods as defined in the independent claims. Further embodiments of the invention are defined in the dependent claims.

BRIEF DESCRIPTION OF THE DRAWINGS

The embodiments, together with further objects and advantages thereof, may best be understood by making reference to the following description taken together with the accompanying drawings, in which:

FIGS. 5A-5B: FFA production was further improved by growth decoupling. (A) Fed-batch fermentation of strain TY36 with glucose limited and nitrogen restriction. Time courses of FFA titers and end point are shown. Overall FFA production at the end of fermentation is 35 g/L. (B) Time courses of DCW (upper curve) and consumed glucose (lower curve) during the fermentation are shown.

DETAILED DESCRIPTION

Figure 1:
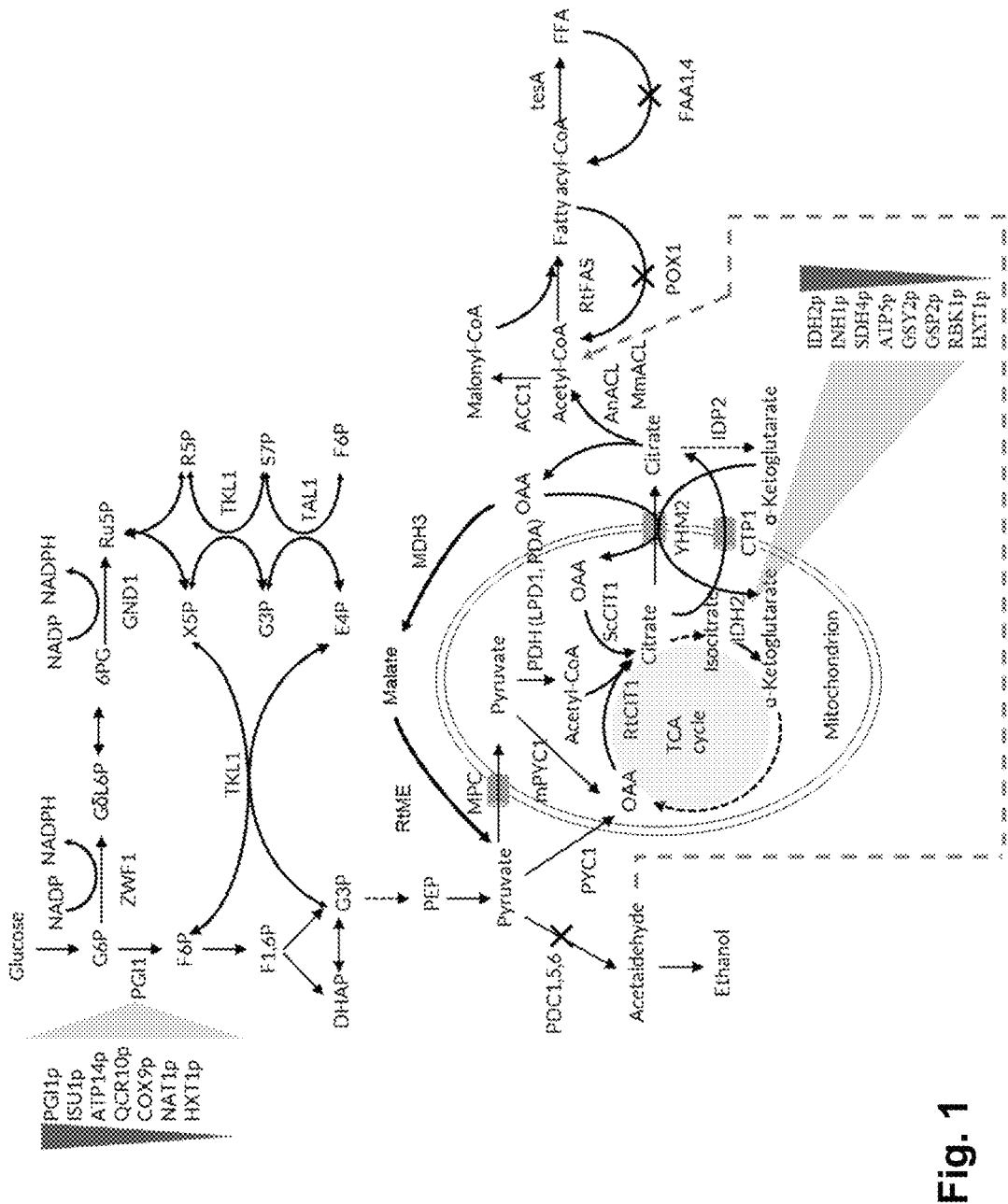
FIG. 1: Schematic illustration of various modifications for increased fatty acid production. Engineering targets include tesA, the truncated *E. coli* thioesterase; MmACL, ATP:citrate lyase from *Mus musculus*; RtME, cytosolic NADP+-dependent malic enzyme from *Rhodosporidium toruloides*; MDH3, endogenous malate dehydrogenase with removed peroxisomal signal; mPYC1, mitochondria-targeted pyruvate carboxylase; CTP1, citrate transporter and RtFAS, fatty acid synthase from *Rhodosporidium toruloides*. For free fatty acid (FFA) production, fatty acyl-CoA synthetase encoding genes FAA1 and FAA4, and fatty acyl-CoA oxidase encoding gene PDX1 were disrupted. Additional engineering targets include MPCox, overexpressed endogenous mitochondrial pyruvate carrier (MPC1 and MPC3); RtCIT1, citrate synthase from *Rhodosporidium toruloides*; ScCIT1, citrate synthase from *Saccharomyces cerevisiae*; AnACL, ATP:citrate lyase from *Aspergillus nidulans*; PDA1, pyruvate dehydrogenase alpha; E3 (LPD1), dihydrolipoamide dehydrogenase; PGI1, phosphoglucose isomerase; ZWF1, cytoplasmic glucose-6-phosphate dehydrogenase; GND1, the isoform 1 of phosphogluconate dehydrogenase; TKL1, transketolase 1; TAL1, transaldolase 1 and IDH2, subunit 2 of mitochondrial NAD(+)-dependent isocitrate dehydrogenase. Native PYC1 (pyruvate carboxylase 1), YHM2 (citrate and oxoglutarate carrier protein 2), IDP2 (cytosolic NADP-specific isocitrate dehydrogenase 2) and ACC1 (acetyl-CoA carboxylase 1) were overexpressed. For the abolishment of ethanol production, pyruvate carboxylase encoding genes PDC1, PDC5 and PDC6 were disrupted. To fine tune gene expression, the promoter of PGI1 was replaced by the promoters of ISU1 (IScU homolog 1), ATP14 (ATP synthase 14), QCR10 (ubiQuinol-cytochrome C oxidoReductase 10), COX9 (Cytochrome c Oxidase 9), NAT1 (N-terminal AcetylTransferase 1), and HXT1 (Low-affinity glucose transporter 1), and the promoter of IDH2 was replaced by the promoters of INH1 (Protein that inhibits ATP hydrolysis by the F1F0-ATP synthase 1), SDH4 (Membrane anchor subunit of succinate dehydrogenase 4), ATPS (ATP synthase 5), GSY2 (Glycogen synthase 2), GSP2 (GTP binding protein 2), RBK1 (RiBoKinase 1), and HXT1.

The present invention now will be described hereinafter with reference to the accompanying drawings and examples, in which embodiments of the invention are shown. This description is not intended to be a detailed catalogue of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined herein, scientific and technical terms used herein will have the meanings that are commonly understood by those of ordinary skill in the art.

Generally, nomenclatures used in connection with techniques of biochemistry, enzymology, molecular and cellular biology, microbiology, genetics and protein and nucleic acid chemistry and hybridization, described herein, are those well-known and commonly used in the art.

Conventional methods and techniques mentioned herein are explained in more detail, for example, in Molecular Cloning, a laboratory manual [second edition] Sambrook et al. Cold Spring Harbor Laboratory, 1989, for example in Sections 1.21 "Extraction And Purification Of Plasmid DNA", 1.53 "Strategies For Cloning In Plasmid Vectors", 1.85 "Identification Of Bacterial Colonies That Contain Recombinant Plasmids", 6 "Gel Electrophoresis Of DNA", 14 "In vitro Amplification Of DNA By The Polymerase Chain Reaction", and 17 "Expression Of Cloned Genes In *Escherichia coli*" thereof.

Enzyme Commission (EC) numbers (also called "classes" herein), referred to throughout this specification, are according to the Nomenclature Committee of the International Union of Biochemistry and Molecular Biology (NC-IUBMB) in its resource "Enzyme Nomenclature" (1992, including Supplements 6-17) available, for example, as "Enzyme nomenclature 1992: recommendations of the Nomenclature Committee of the International Union of Biochemistry and Molecular Biology on the nomenclature and classification of enzymes", Webb, E. C. (1992), San Diego: Published for the International Union of Biochemistry and Molecular Biology by Academic Press (ISBN 0-12-227164-5). This is a numerical classification scheme based on the chemical reactions catalyzed by each enzyme class.

The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

As used herein, the transitional phrase "consisting" essentially of means that the scope of a claim is to be interpreted to encompass the specified materials or steps recited in the claim and those that do not materially affect the basic and novel characteristic(s) of the claimed invention. Thus, the term "consisting essentially of when used in a claim of this invention is not intended to be interpreted to be equivalent to "comprising."

To facilitate understanding of the invention, a number of terms are defined below.

As used herein, the term "fatty acid" refers to a carboxylic acid with a long aliphatic chain, composed of 4 to 40 carbons, which is either saturated or unsaturated. An unsaturated fatty acid contains at least one double or triple bond within its aliphatic chain, which can occur at any position. To define the position of the double bond, the delta-x (delta(x) or Δ-x) nomenclature is used herein. In this nomenclature, each double bond is indicated by "delta(x)", where the double bond is located on the $x^{th}$ carbon-carbon bond, counting from the carboxylic acid end. A fatty acid can be either straight-chained or have branches, i.e., with one or more alkyl groups, such as methyl groups, on the carbon chain. Furthermore, a fatty acid can have additional modifications, such as hydroxylation, i.e., a hydroxy fatty acid, epoxidation, i.e., an epoxy fatty acid and/or comprise multiple, i.e., at least two, carboxylic groups, such as a dicarboxylic fatty acid. Within the cell, fatty acids can occur as free fatty acids (FFAs), fatty acyl-CoAs, fatty acyl-ACPs, fatty acids within triacylglycerols (TAGs), fatty acids within steryl esters, or fatty acids within phospholipids.

As used herein, the term "fatty acid-derived product" refers to any molecule that is created by further modification of a fatty acid in the fungal cell. Examples of fatty acid derived products include, but are not limited to fatty alcohols, fatty aldehydes, fatty acid esters, hydrocarbons, triacylglycerides, lactones and phospholipids.

The term "fatty acyl-CoA" refers to a fatty acid that is bound to a coenzyme A (CoA).

The term "fatty acyl-ACP" refers to a fatty acid that is found to an acyl carrier protein (ACP).

Also, as used herein, the terms "nucleotide sequence" "nucleic acid," "nucleic acid molecule," "oligonucleotide" and "polynucleotide" refer to RNA or DNA, including cDNA, a DNA fragment or portion, genomic DNA, synthetic DNA, plasmid DNA, mRNA, and anti-sense RNA, any of which can be single stranded or double stranded, linear or branched, or a hybrid thereof. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

As used herein the term "recombinant" when used means that a particular nucleic acid (DNA or RNA) is the product of various combinations of cloning, restriction, and/or ligation steps resulting in a construct having a structural coding or non-coding sequence distinguishable from endogenous nucleic acids found in natural systems.

As used herein, the term "gene" refers to a nucleic acid molecule capable of being used to produce mRNA, anti-sense RNA, miRNA, anti-microRNA antisense oligodeoxyribonucleotide (AMO) and the like. Genes may or may not be capable of being used to produce a functional protein or gene product. Genes can include both coding and non-coding regions, e.g., introns, regulatory elements, promoters, enhancers, termination sequences and/or 5' and 3' untranslated regions. A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

A "disrupted gene" as defined herein involves any mutation or modification to a gene resulting in a partial or fully non-functional gene and gene product. Such a mutation or modification includes, but is not limited to, a missense mutation, a nonsense mutation, a deletion, a substitution, an insertion, addition of a targeting sequence and the like. Furthermore, a disruption of a gene can be achieved also, or alternatively, by mutation or modification of control elements controlling the transcription of the gene, such as mutation or modification in a promoter, terminator and/or enhancement elements. In such a case, such a mutation or modification results in partially or fully loss of transcription of the gene, i.e., a lower or reduced transcription as compared to native and non-modified control elements. As a result a reduced, if any, amount of the gene product will be available following transcription and translation. Furthermore, disruption of a gene could also entail adding or removing a localization signal from the gene, resulting in decreased presence of the gene product in its native subcellular compartment.

The objective of gene disruption is to reduce the available amount of the gene product, including fully preventing any production of the gene product, or to express a gene product that lacks or having lower enzymatic activity as compared to the native or wild type gene product.

As used herein the term "deletion" or "knock-out" refers to a gene that is inoperative or knocked out.

The term "lowered activity" or "attenuated activity" when related to an enzyme refers to a decrease in the activity of the enzyme in its native compartment compared to a control or wild-type state. Manipulations that result in attenuated activity of an enzyme include, but are not limited to, a missense mutation, a nonsense mutation, a deletion, a substitution, an insertion, addition of a targeting sequence, removal of a targeting sequence, or the like. Furthermore, attenuation of enzyme activity can be achieved also, or alternatively, by mutation or modification of control elements controlling the transcription of the gene encoding the enzyme, such as mutation or modification in a promoter, terminator and/or enhancement elements. A cell that contains modifications that result in attenuated enzyme activity will have a lower activity of the enzyme compared to a cell that does not contain such modifications. Attenuated activity of an enzyme may be achieved by encoding a nonfunctional gene product, e.g., a polypeptide having essentially no activity, e.g., less than about 10% or even 5% as compared to the activity of the wild type polypeptide.

A "codon optimized" version of a gene refers to an exogenous gene introduced into a cell and where the codons of the gene have been optimized with regard to the particular cell. Generally, not all tRNAs are expressed equally or at the same level across species. Codon optimization of a gene sequence thereby involves changing codons to match the most prevalent tRNAs, i.e., to change a codon recognized by a low prevalent tRNA with a synonymous codon recognized by a tRNA that is comparatively more prevalent in the given cell. This way the mRNA from the codon optimized gene will be more efficiently translated. The codon and the synonymous codon preferably encode the same amino acid.

As used herein, the term "allele" refers to a variant form of a given gene. This can include a mutated form of a gene where one or more of the amino acids encoded by the gene have been removed or substituted by a different amino acid.

As used herein, the terms "peptide", "polypeptide", and "protein" are used interchangeably to indicate to a polymer of amino acid residues. The terms "peptide", "polypeptide" and "protein" also includes modifications including, but not limited to, lipid attachment, glycosylation, glycosylation, sulfation, hydroxylation, γ-carboxylation of L-glutamic acid residues and ADP-ribosylation.

As used herein, the term "enzyme" is defined as a protein which catalyzes a chemical or a biochemical reaction in a cell. Usually, according to the present invention, the nucleotide sequence encoding an enzyme is operably linked to a nucleotide sequence (promoter) that causes sufficient expression of the corresponding gene in the cell to confer to the cell the ability to produce fatty acids.

As used herein, the term "open reading frame (ORF)" refers to a region of RNA or DNA encoding polypeptide, a peptide, or protein.

As used herein, the term "genome" encompasses both the plasmids and chromosomes in a host cell. For instance, encoding nucleic acids of the present disclosure which are introduced into host cells can be portion of the genome whether they are chromosomally integrated or plasmids-localized.

As used herein, the term "promoter" refers to a nucleic acid sequence which has functions to control the transcription of one or more genes, which is located upstream with respect to the direction of transcription of the transcription initiation site of the gene. Suitable promoters in this context include both constitutive and inducible natural promoters as well as engineered promoters, which are well known to the person skilled in the art. In this application, promoters are designed with a "p" in front of the gene name (e.g., "pTEF1" is the promoter of the gene TEF1).

Suitable promoters for use in eukaryotic host cells, such as yeast cells, may be the promoters of PDC, GPD1, TEF1, PGK1 and TDH. Other suitable promoters include the promoters of GAL1, GAL2, GAL10, GAL7, CUP1, HIS3, CYC1, ADH1, PGL, GAPDH, ADC1, URA3, TRP1, LEU2, TPI, AOX1 and ENO1.

As used herein, the term "promoter activity" refers to the ability of a promoter to facilitate expression of the gene lying immediately downstream of said promoter. Typical indicators of a promoter's activity include the timing of expression and level of expression of its downstream gene relative to other genes. A promoter with high or strong activity will lead to high levels of transcription of the gene lying immediately downstream of said promoter, subsequently resulting in high mRNA (and subsequently protein) levels of said gene. A promoter with weak or low activity will lead to low levels of transcription of the gene lying immediately downstream of said promoter, subsequently resulting in low mRNA levels of said gene. Promoter activity can usually be assessed by measuring the mRNA expression of its downstream gene, or by placing a reporter gene immediately downstream of a promoter and observing e.g., fluorescence or colour formation upon respective protein formation. Factors influencing the strength and activity of a promoter can include transcription factor binding (dependent on binding sites in the promoter), efficiency of recruiting RNA polymerases, environmental conditions, etc.

As used herein, the term "terminator" refers to a "transcription termination signal" if not otherwise noted. Terminators are sequences that hinder or stop transcription of a polymerase.

As used herein, "recombinant eukaryotic cells" according to the present disclose is defined as cells which contain additional copies or copy of an endogenous nucleic acid sequence or are transformed or genetically modified with polypeptide or a nucleotide sequence that does not naturally occur in the eukaryotic cells. The wildtype eukaryotic cells are defined as the parental cells of the recombinant eukaryotic cells, as used herein.

As used herein, "recombinant prokaryotic cells" according to the present disclose is defined as cells which contain additional copies or copy of an endogenous nucleic acid sequence or are transformed or genetically modified with polypeptide or a nucleotide sequence that does not naturally occur in the prokaryotic cells. The wildtype prokaryotic cells are defined as the parental cells of the recombinant prokaryotic cells, as used herein.

As used herein, the terms "increase," "increases," "increased," "increasing," "enhance," "enhanced," "enhancing," and "enhancement" (and grammatical variations thereof) indicate an elevation of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more, or any range therein, as compared to a control.

As used herein, the terms "reduce," "reduces," "reduced," "reduction," "diminish," "suppress," and "decrease" and similar terms mean a decrease of at least about, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more, or any range therein, as compared to a control.

A reduced expression of a gene as used herein involves a genetic modification that reduces the transcription of the gene, reduces the translation of the mRNA transcribed from the gene and/or reduces post-translational processing of the protein translated from the mRNA. Such genetic modification includes insertion(s), deletion(s), replacement s) or mutation(s) applied to the control sequence, such as a promoter and enhancer, of the gene. For instance, the promoter of the gene could be replaced by a less active or inducible promoter to thereby result in a reduced transcription of the gene. Also a knock-out of the promoter would result in reduced, typically zero, expression of the gene.

As used herein, the term "portion" or "fragment" of a nucleotide sequence of the invention will be understood to mean a nucleotide sequence of reduced length relative to a reference nucleic acid or nucleotide sequence and comprising, consisting essentially of and/or consisting of a nucleotide sequence of contiguous nucleotides identical or almost identical, e.g., 80%, 81%, 82%, 83%, 84%, 85%, 86%, 87%, 88%, 89%, 90%, 91%, 92%, 93%, 94%, 95%, 96%, 98%, 99% identical, to the reference nucleic acid or nucleotide sequence. Such a nucleic acid fragment or portion according to the invention may be, where appropriate, included in a larger polynucleotide of which it is a constituent.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity, i.e., sequence similarity or identity. Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity, e.g., at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100%, to said nucleotide sequence.

The term "overexpress," "overexpresses", "overexpression" or "upregulation" as used herein refers to higher levels of activity of a gene, e.g., transcription of the gene; higher levels of translation of mRNA into protein; and/or higher levels of production of a gene product, e.g., polypeptide, than would be in the cell in its native or control, e.g., not transformed with the particular heterologous or recombinant polypeptides being overexpressed, state. A typical example of an overexpressed gene is a gene under transcription control of another promoter as compared to the native promoter of the gene. Also, or alternatively, other changes in the control elements of a gene, such as enhancers, could be used to overexpress the particular gene. Furthermore, modifications that affect, i.e., increase, the translation of the mRNA transcribed from the gene could, alternatively or in addition, be used to achieve an overexpressed gene as used herein. These terms can also refer to an increase in the number of copies of a gene and/or an increase in the amount of mRNA and/or gene product in the cell. Overexpression can also be achieved by introducing one or more exogenous versions of the gene from another species. Overexpression can result in levels that are 25%, 50%, 100%, 200%, 500%, 1000%, 2000% or higher in the cell, or any range therein, as compared to control levels.

The term "downregulation" or "down-regulation" as used herein refers to lower levels of activity of a gene, e.g., transcription of the gene; lower levels of translation of mRNA into protein; and/or lower levels of production of a gene product, e.g., polypeptide, than would be in the cell in its native or control, e.g., not transformed with the particular heterologous or recombinant polypeptides being overexpressed, state. A typical example of downregulated gene is a gene under transcription control of another promoter with lower activity as compared to the native promoter of the gene. Also, or alternatively, other changes in the control elements of a gene, such as silencer elements, could be used to downregulate the particular gene. Furthermore, modifications that affect, i.e., decrease, the translation of the mRNA transcribed from the gene could, alternatively or in addition, be used to achieve a downregulated gene as used herein. These terms can also refer to a decrease in the amount of mRNA and/or gene product in the cell. In addition, this term can be used to refer to a gene that is disrupted or completely deleted. Downregulation can result in levels that are 10%, 20%, 50% or 100% lower in the cell, or any range therein, as compared to control levels.

As used herein, the terms "exogenous" or "heterologous" when used with respect to a nucleic acid (RNA or DNA), protein or gene refer to a nucleic acid, protein or gene which occurs non-naturally as part of the cell, organism, genome, RNA or DNA sequence into which it is introduced, including non-naturally occurring multiple copies of a naturally occurring nucleotide sequence. Such an exogenous gene could be a gene from another species or strain, a modified, mutated or evolved version of a gene naturally occurring in the host cell or a chimeric version of a gene naturally occurring in the host cell or fusion genes. In these former cases, the modification, mutation or evolution causes a change in the nucleotide sequence of the gene to thereby obtain a modified, mutated or evolved gene with another nucleotide sequence as compared to the gene naturally occurring in the host cell. Evolved gene refers to genes encoding evolved genes and obtained by genetic modification, such as mutation or exposure to an evolutionary pressure, to derive a new gene with a different nucleotide sequence as compared to the wild type or native gene. A chimeric gene is formed through the combination of portions of one or more coding sequences to produce a new gene. These modifications are distinct from a fusion gene, which merges whole gene sequences into a single reading frame and often retain their original functions.

An "endogenous", "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid sequence is a nucleotide sequence naturally associated with a host cell into which it is introduced.

As used herein, the term "modified", when it is used with respect to an organism, refers to a host organism that has been modified to increase production of fatty acids and/or derived products, as compared with an otherwise identical host organism that has not been so modified. In principle, such "modification" in accordance with the present disclosure may comprise any physiological, genetic, chemical, or other modification that appropriately alters production of fatty acids in a host organism as compared with such production in an otherwise identical organism which is not subject to the said modification. In most of the embodiments, however, the modification will comprise a genetic modification. In certain embodiments, as described herein, the modification comprises introducing genes into a host cell. In some embodiments, a modification comprises at least one physiological, chemical, genetic, or other modification; in other embodiments, a modification comprises more than one chemical, genetic, physiological, or other modification. In certain aspects where more than one modification is made use of, such modifications can include any combinations of physiological, genetic, chemical, or other modification (e.g., one or more genetic, chemical and/or physiological modification(s)). Genetic modifications which boost the activity of a polypeptide include, but are not limited to: introducing one or more copies of a gene encoding the polypeptide (which may distinguish from any gene already present in the host cell encoding a polypeptide having the same activity); altering a gene present in the cell to increase transcription or translation of the gene (e.g., altering, adding additional sequence to, replacement of one or more nucleotides, deleting sequence from, or swapping for example, regulatory, a promoter or other sequence); and altering the sequence (e.g., non-coding or coding) of a gene encoding the polypeptide to boost activity (e.g., by increasing enzyme activity, decrease feedback inhibition, targeting a specific subcellular location, boost mRNA stability, boost protein stability). Genetic modifications that reduce activity of a polypeptide include, but are not limited to: deleting a portion or all of a gene encoding the polypeptide; inserting a nucleic acid sequence which disrupts a gene encoding the polypeptide; changing a gene present in the cell to reduce transcription or translation of the gene or stability of the mRNA or polypeptide encoded by the gene (for example, by adding additional sequence to, altering, deleting sequence from, replacement of one or more nucleotides, or swapping for example, replacement of one or more nucleotides, a promoter, regulatory or other sequence).

The term "overproducing" is used herein in reference to the production of fatty acids or derived products in a host cell and indicates that the host cell is producing more fatty acids or derived products by virtue of the introduction of nucleic acid sequences which encode different polypeptides involved in the host cell's metabolic pathways or as a result of other modifications as compared with the unmodified host cell or wild-type cell.

As used herein, the term "flux", "metabolic flux" or "carbon flux" refers to the rate of turnover of molecules through a given reaction or a set of reactions. Flux in a metabolic pathway is regulated by the enzymes involved in the pathway. Pathways or reactions characterized by a state of increased flux compared to a control have an increased rate of generation of products from given substrates. Pathways or reactions characterized by a state of decreased flux compared to a control have a decreased rate of generation of products from given substrates. Flux towards products of interest can be increased by removing or decreasing competitive reactions or by increasing the activities of enzymes involved in generation of said products.

As used herein, the term "acetyl-CoA derived products" refers to molecules for which acetyl-Coenzyme A (acetyl-CoA) is a precursor. Acetyl-CoA serves as a key precursor metabolite for the production of important cellular constituents such as fatty acids, sterols, and amino acids as well as it is used for acetylation of proteins. Besides these important functions it is also precursor metabolite for many other biomolecules, such as polyketides, isoprenoids, 3-hydroxypropionic acid, 1-butanol and polyhydroxyalkanoids, which encompass many industrially relevant chemicals.

As used herein the term "vector" is defined as a linear or circular DNA molecule comprising a polynucleotide encoding a polypeptide of the invention, and which is operably linked to additional nucleotides that ensure its expression.

"Introducing" in the context of a yeast cell means contacting a nucleic acid molecule with the cell in such a manner that the nucleic acid molecule gains access to the interior of the cell. Accordingly, polynucleotides and/or nucleic acid molecules can be introduced yeast cells in a single transformation event, in separate transformation events. Thus, the term "transformation" as used herein refers to the introduction of a heterologous nucleic acid into a cell. Transformation of a yeast cell can be stable or transient.

"Transient transformation" in the context of a polynucleotide means that a polynucleotide is introduced into the cell and does not integrate into the genome of the cell.

By "stably introducing" or "stably introduced" in the context of a polynucleotide introduced into a cell, it is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. Stable transformation as used herein can also refer to a nucleic acid molecule that is maintained extrachromasomally, for example, as a minichromosome.

Embodiments of the present invention also encompass variants of the polypeptides as defined herein. As used herein, a "variant" means a polypeptide in which the amino acid sequence differs from the base sequence from which it is derived in that one or more amino acids within the sequence are substituted for other amino acids. For example, a variant of SEQ ID NO:1 may have an amino acid sequence at least about 50% identical to SEQ ID NO:1, for example, at least about 55%, 60%, 65%, 70%, 75%, 80%, 85%, 90%, 91%, 92%, 93%, 94%, 95%, 96%, 97%, 98%, 99% or about 100% identical. The variants and/or fragments are functional variants/fragments in that the variant sequence has similar or identical functional enzyme activity characteristics to the enzyme having the non-variant amino acid sequence specified herein (and this is the meaning of the term "functional variant" as used throughout this specification).

A "functional variant" or "functional fragment" of any of the presented amino acid sequences, therefore, is any amino acid sequence which remains within the same enzyme category (i.e., has the same EC number) as the non-variant sequences. Methods of determining whether an enzyme falls within a particular category are well known to the skilled person, who can determine the enzyme category without use of inventive skill. Suitable methods may, for example, be obtained from the International Union of Biochemistry and Molecular Biology.

Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

Class Amino Acid Examples
Nonpolar: A, V, L, I, P, M, F, W
Uncharged polar: G, S, T, C, Y, N, Q
Acidic: D, E
Basic: K, R, H.

As it is well known to those skilled in the art, altering the primary structure of a polypeptide by a conservative substitution may not significantly alter the activity of that polypeptide because the side-chain of the amino acid which is inserted into the sequence may be able to form similar bonds and contacts as the side chain of the amino acid which has been substituted out. This is so even when the substitution is in a region which is critical in determining the polypeptide's conformation.

In embodiments of the present invention, non-conservative substitutions are possible provided that these do not interrupt the enzyme activities of the polypeptides, as defined elsewhere herein. The substituted versions of the enzymes must retain characteristics such that they remain in the same enzyme class as the non-substituted enzyme, as determined using the NC-IUBMB nomenclature discussed above.

Broadly speaking, fewer non-conservative substitutions than conservative substitutions will be possible without altering the biological activity of the polypeptides. Determination of the effect of any substitution (and, indeed, of any amino acid deletion or insertion) is wholly within the routine capabilities of the skilled person, who can readily determine whether a variant polypeptide retains the enzyme activity according to aspects of the invention. For example, when determining whether a variant of the polypeptide falls within the scope of the invention (i.e., is a "functional variant or fragment" as defined above), the skilled person will determine whether the variant or fragment retains the substrate converting enzyme activity as defined with reference to the NC-IUBMB nomenclature mentioned elsewhere herein. All such variants are within the scope of the invention.

Using the standard genetic code, further nucleic acid sequences encoding the polypeptides may readily be conceived and manufactured by the skilled person, in addition to those disclosed herein. The nucleic acid sequence may be DNA or RNA, and where it is a DNA molecule, it may for example comprise a cDNA or genomic DNA. The nucleic acid may be contained within an expression vector, as described elsewhere herein.

Embodiments of the invention, therefore, encompass variant nucleic acid sequences encoding the polypeptides contemplated by embodiments of the invention. The term "variant" in relation to a nucleic acid sequence means any substitution of, variation of, modification of, replacement of, deletion of, or addition of one or more nucleotide(s) from or to a polynucleotide sequence, providing the resultant polypeptide sequence encoded by the polynucleotide exhibits at least the same or similar enzymatic properties as the polypeptide encoded by the basic sequence. The term includes allelic variants and also includes a polynucleotide (a "probe sequence") which substantially hybridizes to the polynucleotide sequence of embodiments of the present invention. Such hybridization may occur at or between low and high stringency conditions. In general terms, low stringency conditions can be defined as hybridization in which the washing step takes place in a 0.330-0.825 M NaCl buffer solution at a temperature of about 40-48° C. below the calculated or actual melting temperature (Tm) of the probe sequence (for example, about ambient laboratory temperature to about 55° C.), while high stringency conditions involve a wash in a 0.0165-0.0330 M NaCl buffer solution at a temperature of about 5-10° C. below the calculated or actual Tm of the probe sequence (for example, about 65° C.). The buffer solution may, for example, be SSC buffer (0.15M NaCl and 0.015M tri-sodium citrate), with the low stringency wash taking place in 3×SSC buffer and the high stringency wash taking place in 0.1×SSC buffer. Steps involved in hybridization of nucleic acid sequences have been described for example in Molecular Cloning, a laboratory manual [second edition] Sambrook et al. Cold Spring Harbor Laboratory, 1989, for example in Section 11 "Synthetic Oligonucleotide Probes" thereof (herein incorporated by reference)

Preferably, nucleic acid sequence variants have about 55% or more of the nucleotides in common with the nucleic acid sequence of embodiments of the present invention, more preferably at least 60%, 65%, 70%, 80%, 85%, or even 90%, 95%, 98% or 99% or greater sequence identity.

Variant nucleic acids of the invention may be codon-optimized for expression in a particular host cell.

As used herein, "sequence identity" refers to sequence similarity between two nucleotide sequences or two peptide or protein sequences. The similarity is determined by sequence alignment to determine the structural and/or functional relationships between the sequences.

Sequence identity between amino acid sequences can be determined by comparing an alignment of the sequences using the Needleman-Wunsch Global Sequence Alignment Tool available from the National Center for Biotechnology Information (NCBI), Bethesda, Md., USA, for example via http://blast.ncbi.nlm.nih.gov/Blast.cgi, using default parameter settings (for protein alignment, Gap costs Existence:11 Extension:1). Sequence comparisons and percentage identities mentioned in this specification have been determined using this software.

An aspect of the embodiments relates to a fungal cell suitable for the production of fatty acids and/or fatty acid-derived products. The fungal cell is, in this aspect, genetically modified for overexpression of an acetyl-CoA carboxylase (EC 6.4.1.2) and a pyruvate carboxylase (EC 6.4.1.1).

In the following, various embodiments of the present invention will be described in more detail.

In an embodiment, the fungal cell is a fungal cell selected from a group consisting of *Saccharomyces, Kluyveromyces, Zygosaccharomyces, Candida, Hansenula, Torulopsis, Kloeckera, Pichia, Schizosaccharomyces, Trigonopsis, Brettanomyces, Debaromyces, Nadsonia, Lipomyces, Cryptococcus, Aureobasidium, Trichosporon, Lipomyces, Rhodo-* torula, Yarrowia, Rhodosporidium, Phaffia, Schwanniomyces, Aspergillus and Ashbya. In a particular embodiment, the fungal cell can be Saccharomyces cerevisiae, Pichia pastoris, Ashbya gossypii, Saccharomyces boulardii, Zygosaccharomyces bailii, Kluyveromyces lactis, Rhodosporidium toruloides and Yarrowia lipolytica. Saccharomyces cerevisiae and Yarrowia lipolytica are preferred yeast species.

According to the invention, the fungal cell is engineered for increased supply of acetyl-CoA and/or malonyl-CoA, precursors for fatty acids. This is achieved by upregulation of genes coding for pyruvate carboxylase (PYC) to increase oxaloacetate supply and acetyl-CoA carboxylase (ACC) to increase pull towards malonyl-CoA. For instance, production of the enzymes PYC1 (YGL062W) and ACC1 (YNR016C) could be upregulated in the fungal cell.

In an embodiment, the fungal cell is genetically modified for overexpression of a mitochondrial pyruvate carrier to increase pyruvate import into mitochondria under high glucose. For instance, production of the proteins MPC1 (YGL080W) and/or MPC3 (YGR243W) could be upregulated in the fungal cell. These modifications could be combined with the modifications above, or be completely independent.

In an embodiment, the fungal cell is further genetically modified for overexpression of a citrate and oxoglutarate carrier protein, which is an antiporter contributing to increased NADPH in the cytosol. For instance, production of the protein YHM2 (YMR241W) could be upregulated in the fungal cell.

In an embodiment, the fungal cell is further genetically modified for overexpression of a cytosolic isocitrate dehydrogenase (IDH) (EC 1.1.1.42). For instance, production of the enzyme IDP2 (YLR174W) could be upregulated in the fungal cell.

Any or all of the above mentioned embodiments could be combined in the fungal cell.

According to the invention, the fungal cell is genetically modified for enhanced activity of acetyl-CoA carboxylase, preferably ACC1 (SEQ ID NO: 1), or a variant of SEQ ID NO: 1. This may be achieved via overexpression of ACC1 and/or via expression or overexpression of a mutant ACC1 variant with higher activity. Illustrative, but non-limiting, example of such mutant ACC1 variants include ACC1 from Saccharomyces cerevisiae, in which serine 659 in SEQ ID NO: 1 and/or serine 1157 in SEQ ID NO: 1 is/are replaced with alanine.

According to the invention, the fungal cell is genetically modified for enhanced activity of pyruvate carboxylase, preferably PYC1 (SEQ ID NO: 2), or a variant of SEQ ID NO: 2. This can be achieved, for example, via overexpression of PYC1.

Another aspect of the embodiments relates to a fungal cell for the production of fatty acids and/or fatty acid-derived products. The fungal cell is genetically modified for overexpression of an acetyl-CoA carboxylase, preferably ACC1, and for overexpression of a mitochondrial pyruvate carrier, preferably MPC1 and/or MPC3. In another embodiment, the fungal cell is genetically modified for overexpression of a pyruvate carboxylase, preferably PYC1, and for overexpression of a mitochondrial pyruvate carrier, preferably MPC1 and/or MPC3.

In the fungal cell is genetically modified for:
Overexpression or enhanced activity of an acetyl-CoA carboxylase, preferably ACC1, and
Overexpression or enhanced activity of a pyruvate carboxylase, preferably PYC1, and
Overexpression or enhanced activity of a mitochondrial pyruvate carrier, preferably MPC1 and/or MPC3

In an embodiment, the fungal cell also comprises modifications focusing on increasing the synthesis of citrate as precursor for acetyl-CoA in the fungal cell. This could be achieved by overexpression of a citrate synthase (EC 2.3.3.16), such as overexpression of S. cerevisiae citrate synthase ScCIT1 (YNR001C) and/or overexpression of citrate synthase RtCIT1 from Rhodosporidium toruloides (SEQ ID NO: 3), or a variant of SEQ ID NO: 3.

In another embodiment, the fungal cell instead or in addition comprises modifications to enhance mitochondrial oxaloacetate production required for citrate synthesis by targeting the cytosolic pyruvate carboxylase into the mitochondria (mPYC1) (SEQ ID NO: 4), or a variant of SEQ ID NO: 4.

In another embodiment, the fungal cell instead or in addition comprises modifications to enhance the flux from citrate to acetyl-CoA via expression, preferably overexpression, of an ATP-citrate-lyase (EC 2.3.3.8), preferably a heterologous ATP-citrate lyase, such as AnACL from Aspergillus nidulans (SEQ ID NO: 5), or a variant of SEQ ID NO: 5.

In another embodiment, the fungal cell instead or in addition comprises modifications to enhance export of citrate from the mitochondria to the cytosol by downregulation of the gene coding for the mitochondrial NAD+-dependent isocitrate dehydrogenase IDH2 (YOR136W, EC 1.1.1.41) (SEQ ID NO: 14). This modification could be combined with any of the modifications above or be completely independent. In the latter case, the invention relates to a fungal cell, preferably a fungal cell for the production of fatty acids and/or fatty acid-derived products, wherein the fungal cell is genetically modified for downregulation of the gene coding for the mitochondrial NAD+-dependent isocitrate dehydrogenase IDH2 (YOR136W, EC 1.1.1.41) (SEQ ID NO: 14).

The downregulation of the endogenous mitochondrial NAD+-dependent isocitrate dehydrogenase can be achieved by having a native promoter of the mitochondrial NAD+-dependent isocitrate dehydrogenase replaced by a comparatively weaker promoter. For instance, the native promoter can be replaced by a weaker promoter selected from the group consisting of pINH1, pSDH4, pATP5, pGSY2, pGSP2, and pRBK1.

Any of the above described modifications can be combined.

A further aspect of the embodiments relates to a fungal cell for the production of fatty acids and/or fatty acid-derived products. The fungal cell is genetically modified for overproduction of an acetyl-CoA carboxylase, preferably ACC1, and for overexpression of a citrate synthase, preferably CIT1 from Rhodosporidium toruloides. In another embodiment, the fungal cell is genetically modified for overexpression of a citrate synthase, preferably CIT1 from Rhodosporidium toruloides, and for overexpression of a pyruvate carboxylase, preferably PYC1.

In an embodiment, the fungal cell is genetically modified for:
Overexpression or enhanced activity of an acetyl-CoA carboxylase, preferably ACC1, and
Overexpression or enhanced activity of a pyruvate carboxylase, preferably PYC1, and
Overexpression or enhanced activity of a citrate synthase, preferably CIT1 from Rhodosporidium toruloides.

In an embodiment, the fungal cell is genetically modified for overexpression of the citrate synthase, preferably CIT1 from *Rhodosporidium toruloides*, and for overexpression of a citrate and oxoglutarate carrier protein, preferably YHM2.

In an embodiment, the fungal cell is instead or in addition genetically modified for overexpression of the citrate synthase, preferably CIT1 from *Rhodosporidium toruloides*, and for overexpression of a cytosolic isocitrate dehydrogenase, preferably IDP2.

In an embodiment, the fungal cell is modified for overexpression of the citrate synthase, preferably CIT1 from *Rhodosporidium toruloides*, and for overexpression of an ATP-citrate-lyase, preferably AnACL from *Aspergillus nidulans*.

In an embodiment, the fungal cell with any of the above modifications is further genetically modified for downregulation of an endogenous mitochondrial NAD+-dependent isocitrate dehydrogenase, for example IDH2. Downregulation of the mitochondrial NAD+-dependent isocitrate dehydrogenase can be accomplished by replacement of the native promoter of the mitochondrial NAD+-dependent isocitrate dehydrogenase with a weaker promoter, preferably taken from the group consisting of pINH1, pSDH4, pATP5, pGSY2, pGSP2, pRBK1.

In a preferred embodiment, a fungal cell is modified for increased NADPH supply for elongation and reduction reactions. This could be achieved by downregulation of a gene encoding for an endogenous phosphoglucose isomerase (PGI) (YBR196C, EC 5.3.1.9), thereby directing the metabolic flux into the pentose phosphate pathway (PPP) for increased generation of NADPH. Thus, in an embodiment, the fungal cell with any of the above modifications is further genetically modified for downregulation of the endogenous phosphoglucose isomerase, for example PGI1. Downregulation of the endogenous phosphoglucose isomerase may be accomplished by replacement of the native promoter controlling the expression of the phosphoglucose isomerase by a weaker promoter, preferably selected from the group consisting of pISU1, pATP14, pQCR10, pCOX9, pNAT1 and pHXT1. This modification could be combined with any of the modifications above or be completely independent. In the latter case, the invention relates to a fungal cell, preferably a fungal cell for the production of fatty acids and/or fatty acid-derived products, wherein the fungal cell is genetically modified for downregulation of the endogenous phosphoglucose isomerase, for example PGI1 (YBR196C, EC 5.3.1.9).

In another preferred embodiment, NADPH supply in the fungal cell is further increased by overexpressing genes coding for a glucose-6-phosphate dehydrogenase (ZWF1; YNL241C, EC 1.1.1.49) catalyzing the irreversible and rate limiting first step of PPP and is responsible for the main NADPH regeneration from NADP+; GND1 (YHR183W, EC 1.1.1.44) encoding the major phosphogluconate dehydrogenase that catalyzes the second oxidative reduction of NADP+ to NADPH; TKL1 (YPR074C, EC 2.2.1.1) and TAL1 (YLR354C, EC 2.2.1.2) encoding a transketolase and a transaldolase of the non-oxidative PPP. Other ways to increase NADPH could include expression of a gene coding for a non-phosphorylating NADP+-dependent glyceraldehydes-3-phosphate dehydrogenase (GAPN; preferably from *Streptococcus mutans*), or a phosphoketolase pathway e.g., from *Aspergillus nidulans* (heterologous expression of xpkA and ack). In an embodiment, the fungal cell is a *Saccharomyces cerevisiae* cell genetically modified for overexpression of an endogenous GDH2 (YDL215C, EC 1.4.1.2) gene encoding a NAD-dependent glutamate dehydrogenase. These modifications could be combined with any of the modifications above, or be completely independent.

In a preferred embodiment, the fungal cell is genetically modified for overexpression of an acetyl-CoA carboxylase, preferably ACC1, and overexpression of a pyruvate carboxylase, preferably PYC1, and any of the following:

Overexpression of a mitochondrial pyruvate carrier, preferably MPC1 and/or MPC3, and/or Overexpression of a citrate synthase, preferably CIT1 from *Rhodosporidium toruloides*, and/or Overexpression of a citrate and oxoglutarate carrier protein, preferably YHM2, and/or Overexpression of a cytosolic isocitrate dehydrogenase, preferably IDP2, and/or Overexpression of an ATP-citrate lyase, preferably from *Aspergillus nidulans*, and/or Downregulation of the endogenous mitochondrial NAD+-dependent isocitrate dehydrogenase, preferably IDH2, and/or Downregulation of the endogenous phosphoglucose isomerase, preferably PGI1.

In an embodiment, the fungal cell is a *S. cerevisiae* with the following modifications:

Upregulation of genes coding for PYC1 (YGL062W, EC 6.4.1.1) (increasing oxaloacetate supply), ACC1 (YNR016C; EC 6.4.1.2) (increasing pull towards malonyl-CoA), IDP2 (YLR174W, EC 1.1.1.42), YHM2 (YMR241W) (antiporter contributing to increased NADPH in cytosol), MPC1 (YGL080W) and MPC3 (YGR243W) (increase pyruvate import into mitochondria under high glucose), and Downregulation of endogenous genes encoding for a phosphoglucose isomerase PGI1 (YBR196C, EC 5.3.1.9), thereby directing the metabolic flux into the pentose phosphate pathway for increased generation of NADPH;

Increasing NADPH supply in the fungal cell by overexpressing genes coding for a glucose-6-phosphate dehydrogenase (ZWF1, YNL241C, EC 1.1.1.49), the major phosphogluconate dehydrogenase GND1 coded by GND1 (YHR183W, EC 1.1.1.44), a transketolase and a transaldolase coded by TKL1 (YPR074C, EC 2.2.1.1) and TAL1 (YLR354C, EC 2.2.1.2); and Enhanced export of citrate from the mitochondria to the cytosol by downregulation of the gene coding for the mitochondrial NAD+-dependent isocitrate dehydrogenases IDH2 (YOR136W, EC 1.1.1.41) and IDP1 (YDL066W, EC 1.1.1.42) (SEQ ID NO: 6), ora variant of SEQ ID NO: 6.

In an embodiment, the fatty acid production in the fungal cell could be increased by redirecting the flux from cell growth to fatty acid production by limiting cell growth through downregulation of essential genes by replacing a native promoter of the essential gene by a carbon-source dependent promoter. For example, the PHXT1 promoter could be introduced to control the expression of the essential genes ERG9 (YHR190W, EC 2.5.1.21) and/or LEU2 (YCL018W, EC 1.1.1.85) in, for instance, *S. cerevisiae* or *Y. lipolytica* to limit cell growth at low glucose concentrations. These modifications could be combined with any of the modifications above, or be completely independent.

In an embodiment, the fatty acid production in the fungal cell factory could be increased by redirecting the flux from cell growth to fatty acid production by limiting cell growth through limiting supply of an essential nutrient. For example the supply of nitrogen is limiting cell growth in *S. cerevisiae* and leads to increase of fatty acid production.

In an embodiment, any of the modifications above may be combined with genetic modifications in the fungal cell to abolish ethanol formation. This includes downregulating pyruvate decarboxylase activity in the fungal cell by deletion of one or more genes coding for pyruvate decarboxylases catalyzing the decarboxylation of pyruvate to acetaldehyde. For example, deletion of the genes PDC1, PDC5, and/or PDC6 (YLR044C, YLR134W, YGR087C, SEQ ID NO: 7-9), or variants of SEQ ID NI: 7-9, in the yeast *S. cerevisiae* leads to abolishment of ethanol formation (Zhang et al., 2015.) and all or some of these could be deleted or downregulated to decrease or completely abolish ethanol production.

In another embodiment, any of the modifications above are combined with genetic modifications to restore growth on glucose of fungal cells abolished for ethanol formation. This includes inserting specific mutations in the gene MTH1$^{81D}$ (YDR277C) or truncated versions of the MTH1 gene (SEQ ID NO: 10), coding for a version with higher activity.

In another embodiment any of the modifications above are combined with adaptive laboratory evolution (ALE) to restore growth on glucose of fungal cells abolished for ethanol formation. This includes e.g., exposing the engineered yeast cell stepwise to lower concentrations of ethanol with at the same time increasing the concentration of glucose in the cultivation medium.

In an embodiment, the fungal cell is modified to abolish ethanol formation as well as lower the activity of a fructose-1,6-bisphosphate (FBP)-sensitive pyruvate kinase, for example PYK1 (SEQ ID NO: 11), also known as CDC19, or a variant of SEQ ID NO: 11. In another embodiment, the fungal cell is alternatively, or in addition, modified for increased activity of a FBP-insensitive pyruvate kinase, such as PYK2 (SEQ ID NO: 12), or a variant of SEQ ID NO: 12. Downregulation of PYK1 activity can be accomplished by deletion, promoter replacement, or mutation, for example in the R68, K196, or R91 residues. Increased activity of PYK2 can be accomplished by overexpression, for example via promoter replacement or introduction of additional copies. For example, in a preferred embodiment a fungal cell with deletions in the genes PDC1 and PDC5 is further modified for downregulation of PYK1 and overexpression of PYK2. These modifications can be combined with the above modifications for fatty acid production, or be completely independent.

In an embodiment, the fungal cell is genetically modified for:
Overexpression or enhanced activity of an acetyl-CoA carboxylase, preferably by overexpression of ACC1, and
Overexpression or enhanced activity of a pyruvate carboxylase, preferably by overexpression of PYC1, and
Downregulation or decreased activity of a pyruvate decarboxylase, preferably by deletion of PDC1, PDC5 and/or PDC6, and
Downregulation or decreased activity of a FBP-sensitive pyruvate kinase, preferably by deletion or downregulation of PYK1.

In an embodiment, the fungal cell is genetically modified for:
Overexpression or enhanced activity of an acetyl-CoA carboxylase, preferably by overexpression of ACC1, and
Overexpression or enhanced activity of a pyruvate carboxylase, preferably by overexpression of PYC1, and
Downregulation or decreased activity of a pyruvate decarboxylase, preferably by deletion of PDC1, PDC5 and/or PDC6, and
Overexpression or enhanced activity of a FBP-insensitive pyruvate kinase, preferably by overexpression of PYK2.

In an embodiment, the fungal cell is a *Saccharomyces cerevisiae* yeast cell genetically modified for overproduction of an acetyl-CoA-derived product. The yeast cell is further modified for decreased ethanol production via deletion or downregulation of PDC1, PDC5 and/or PDC6. In a further embodiment the yeast cell is genetically modified for deletion or downregulation of PYK1. In a further embodiment the aforementioned yeast cell is further modified for overexpression of PYK2. These modifications can be combined with the above modifications for fatty acid production, or be completely independent.

In a preferred embodiment, the fungal cell is genetically modified for:
Overexpression or enhanced activity of an acetyl-CoA carboxylase, preferably by overexpression of ACC1, and
Overexpression or enhanced activity of a pyruvate carboxylase, preferably by overexpression of PYC1, and
Downregulation or decreased activity of a pyruvate decarboxylase, preferably by deletion of PDC1, PDC5 and/or PDC6, and
Downregulation or decreased activity of a FBP-sensitive pyruvate kinase, preferably by deletion or downregulation of PYK1, and
Overexpression or enhanced activity of a FBP-insensitive pyruvate kinase, preferably by overexpression of PYK2.

In some embodiments, the fungal cell has increased production capacities for free fatty acids incorporating genetic modifications, including deletion of the genes coding for a fatty aldehyde dehydrogenase (HFD1, YMR110C, EC 1.2.1.3), a fatty-acyl coenzyme A oxidase (POX1, YGL205W, EC 1.3.3.6) and/or fatty acyl-CoA synthetases FAA1 (YOR317W, EC 6.2.1.3) and FAA4 (YMR246W, EC 6.2.1.3). In addition, or alternatively, the fungal cell is genetically modified for overexpression of heterologous genes including *Mus musculus* ATP-citrate-lyase (MmACL, EC 2.3.3.8), *R. toruloides* malic enzymes (RtME, EC 1.1.1.40), a truncated version of *E. coli* thioesterase (tesA, EC 3.1.2.2.) and overexpression of *R. toruloides* FAS encoding genes (RtFAS1 and RtFAS2). In an embodiment, to further increase free fatty acid production endogenous genes coding for mitochondrial citrate transporter (CTP1, YBR291C) and malate dehydrogenase (MDH3, YDL078C, EC 1.1.1.37) may be overexpressed. These modifications could be combined with any of the modifications above, or be completely independent.

In an embodiment, the fungal cell is genetically modified for:
Deletion in PDX1, FAA1 and FAA4, and
Overexpression of a thioesterase, preferably tesA from *Escherichia coli*, and
Overexpression of endogenous ACC1 and PYC1, and
Deletion of PDC1, PDC5 or PDC6, and
Deletion of PYK1, and
Overexpression of PYK2.

In another embodiment, the fungal cell is *Saccharomyces cerevisiae* and is genetically modified for:
Deletion of HFD1, PDX1, FAA1 and FAA4, and
Overexpression of an ATP-citrate lyase, preferably from *Mus Musculus* or *Aspergillus nidulans*, and Overexpression of a cytosolic NADP+-dependent malic enzyme, preferably from *Rhodosporidium toruloides*, and Overexpression of endogenous CTP1 and MDH3, and Overexpression of a thioesterase, preferably tesA from *Escherichia coli*, and Overexpression of FAS1 and/or FAS2, preferably from *Rhodosporidium toruloides*, and Overexpression of endogenous ACC1 and PYC1, and Overexpression of CIT1, preferably from *Rhodosporidium toruloides*, and Overexpression of endogenous PDA1, IDP2 and YHM2, and Downregulation of PGI1, and Overexpression of endogenous GND1, TKL1, TAL1, and ZWF1, and Downregulation of IDH2, and Deletion of PDC1, PDC5 and PDC6, and Deletion of PYK1, and Overexpression of PYK2.

In an embodiment, increased production of fatty acids and/or fatty acid-derived products is, instead or in addition, achieved through overexpression of one or more endogenous yeast genes selected from the group consisting of M-Phase Phosphoprotein 6 homolog (MPP6) (SEQ ID NO: 27), or a variant of SEQ ID NO:27; Acyl Carrier Protein (ACP1) (SEQ ID NO: 28), or a variant of SEQ ID NO: 28; EthanolaminePhosphoTransferase (EPT1) (SEQ ID NO: 29), or a variant of SEQ ID NO: 29; Long chain fatty acyl-CoA synthetase (FAA1) (SEQ ID NO: 30), or a variant of SEQ ID NO: 30; Mitochondrial phosphatidylglycerophosphatase (GEP4) (SEQ ID NO: 31), or a variant of SEQ ID NO: 31; ADP-ribosylation factor-binding protein GGA2 (GGA2) (SEQ ID NO: 13), or a variant of SEQ ID NO: 13; NADP-dependent isocitrate dehydrogenase (IDP3) (SEQ ID NO: 32), or a variant of SEQ ID NO: 32; Phosphatidylinositol 4,5-bisphosphate 5-phosphatase (INP54) (SEQ ID NO: 33), or a variant of SEQ ID NO: 33; Lipid phosphate phosphatase (LPP1) (SEQ ID NO: 34), or a variant of SEQ ID NO: 34; Mitochondrial NADH-cytochrome b5 reductase (MCR1) (SEQ ID NO: 35), or a variant of SEQ ID NO: 35; sphingolipid homeostasis protein ORM1 (ORM1) (SEQ ID NO: 36), or a variant of SEQ ID NO: 36; Restriction of telomere capping protein 3 (RTC3) (SEQ ID NO: 37), or a variant of SEQ ID NO: 37; SPO7 (SEQ ID NO: 38), or a variant of SEQ ID NO: 38; TriGlyceride Lipase (TGL1) (SEQ ID NO: 39), or a variant of SEQ ID NO: 39; YFT2 (SEQ ID NO: 40), or a variant of SEQ ID NO: 40. These modifications can be combined with any of the above modifications or be completely independent. In a preferred embodiment, the fungal cell overexpresses GGA2 (SEQ ID NO: 13), or a variant of SEQ ID NO: 13. This modification can be combined with any of the above modifications or be completely independent.

In an embodiment, the fungal cell overexpresses GGA2 and INP54. This modification can be combined with any of the above modifications or be completely independent.

In an embodiment, the fungal cell overexpresses GGA2 and IDP3. This modification can be combined with any of the above modifications or be completely independent.

In an embodiment, the fungal cell overexpresses GGA2 and TGL1. This modification can be combined with any of the above modifications or be completely independent.

In an embodiment, the fungal cell overexpresses INP54 and IDP3. This modification can be combined with any of the above modifications or be completely independent.

In an embodiment, the fungal cell overexpresses GGA2, INP54 and IDP3. This modification can be combined with any of the above modifications or be completely independent.

In an embodiment, the fungal cell overexpresses GGA2, INP54, IDP3 and TGL1. This modification can be combined with any of the above modifications or be completely independent.

In an embodiment, the fungal cell overexpresses GGA2 and is used for production of a fatty acid composed of 16 carbons, including, but not limited to, palmitic acid or palmitoleic acid. This modification can be combined with any of the above modifications or be completely independent.

In an embodiment, the fungal cell overexpresses EPT1 and is used for production of a fatty acid composed of 16 carbons, including, but not limited to, palmitic acid or palmitoleic acid. This modification can be combined with any of the above modifications or be completely independent.

In an embodiment, the fungal cell overexpresses IDP3 and is used for production of a fatty acid composed of 16 carbons, including, but not limited to, palmitic acid or palmitoleic acid. This modification can be combined with any of the above modifications or be completely independent.

In an embodiment, the fungal cell overexpresses TGL1 and is used for production of a fatty acid composed of 16 carbons, including, but not limited to, palmitic acid or palmitoleic acid. This modification can be combined with any of the above modifications or be completely independent.

In an embodiment, the fungal cell overexpresses RTC3 and is used for production of oleic acid. This modification can be combined with any of the above modifications or be completely independent.

In an embodiment, the fungal cell for production of fatty acids is genetically modified for:
  Overexpression or enhanced activity of an acetyl-CoA carboxylase and/or a pyruvate carboxylase, and
  Overexpression or enhanced activity of GGA2

In an embodiment, the fungal cell for production of fatty acids is genetically modified for:
  Overexpression or enhanced activity of an acetyl-CoA carboxylase and/or a pyruvate carboxylase, and
  Overexpression or enhanced activity of a citrate synthase and/or a mitochondrial pyruvate carrier, and
  Overexpression or enhanced activity of GGA2.

In an embodiment, the fungal cell is genetically modified for:
  Reduction in ethanol formation by downregulation or deletion of genes selected from the group consisting of PDC1, PDC5 and PDC6, and
  Downregulation of PYK1 and/or overexpression of PYK2, and
  Overexpression of GGA2.

In some embodiments, the fungal cell is further modified for reduced expression or knockout of pathways competing for fatty acids. This can include genes selected from a group consisting of acyl-CoA: sterol acyltransferase (ARE1, YCR048W, EC 2.3.1.26; ARE2, YNR019W, EC 2.3.1.26), diacylglycerol acyltransferase (DGA1, YOR245C, EC 2.3.1.20), lecithin cholesterol acyl transferase (LRO1, YNR008W, EC 2.3.1.158), fatty-acyl coenzyme A oxidase (POX1, YGL205W, EC 1.3.3.6).

In some embodiments, the fungal cell is further modified for reduced expression or knockout of genes involved in fatty acid activation in order to increase accumulation of free fatty acids. This can include, for example, fatty acyl-coA synthetases, such as the genes FAA1 (YOR317W, EC 6.2.1.3), FAA2 (YER015W, EC 6.2.1.3), FAA3 (YIL009W, EC 6.2.1.3), FAA4 (YMR246W, EC 6.2.1.3) and FAT1 YBR041W, EC 6.2.1.3).

In some embodiments, endogenous fatty acid genes are de-regulated. For example, the elongation genes, ELO1, ELO2 and/or ELO3, can be de-regulated if shorter-chain (less than 16 carbons) or longer-chain (more than 18 carbons) fatty acids are required so that a) their expression and/or activity is lower during the production phase than during the growth phase and (b) the expression and/or activity during the production phase is lower than the endogenous expression and/or activity during this phase as compared to a non-de-regulated control. Such de-regulation could be achieved via promoter replacement or via other means as described above.

In some embodiments, the fungal cell is modified for increased conversion of fatty acyl CoAs to free fatty acids with the overexpression of a thioesterase. This can be done via overexpression of endogenous thioesterases, or heterologous thioesterases, such as mammalian ACOT genes, for instance, *Homo sapiens* ACOT2 (GenBank: P 006812.3), *Homo sapiens* ACOT9 (Genbank: P_001028755.2), *Rattus norvegicus* ACOT2 (GenBank: P_620262.2) or *Rattus norvegicus* ACOT 1 (Genbank: P_112605.1).

In some embodiments, any of the modifications above can be combined with expression of acyl-CoA oxidases (EC 1.3.3.6) or acyl-CoA dehydrogenases (EC 1.3.8.7) to facilitate chain shortening of the fatty acid.

In an embodiment, the fungal cell is genetically modified for overexpression of at least one enzyme involved in fatty acid synthesis in the fungal cell and selected from the group consisting of a fatty acid synthase, such as FAS1 and/or FAS2; an acyl-CoA-binding protein, such as ACB1; a mitochondrial citrate transporter, such as CTP1; a malate dehydrogenase, such as MDH3; cytosolic isocitrate dehydrogenase, such as IDP2; a citrate and oxoglutarate carrier protein, such as YHM2; a mitochondrial pyruvate carrier, such as MPC1 and/or MPC3; a citrate synthase, such as CIT1; a glucose-6-phosphate dehydrogenase, such as ZWF1; a transketolase, such as TKL1; a transaldolase, such as TAL1; and a glutamate dehydrogenase, such as GDH2.

In an embodiment, the fungal cell is genetically modified for attenuated activity or downregulation of at least one enzyme involved in fatty acid biosynthesis in the fungal cell and selected from the group consisting of a fatty-acyl-CoA synthetase, such as FAA1, FAA2, FAA3, FAA4 and/or FAT1; a fatty aldehyde dehydrogenase, such as HFD1; a fatty-acyl-CoA oxidase, such as PDX1; a mitochondrial isocitrate dehydrogenase, such as IDH2 and/or IDP1; a phosphoglucose isomerase, such as PGI1; an acyl-CoA-sterol acyltransferase, such as ARE1 and/or ARE2; a diacylglycerol acyltransferase, such as DGA1; and a lecithin cholesterol acyl transferase, such as LRO1.

In an embodiment, the fungal cell is a yeast cell.

In an embodiment, the fatty acid is selected from the group consisting of stearic acid, oleic acid, palmitic acid, palmitoleic acid and a mixture thereof.

In some embodiments, the fatty acids are further processed into fatty acid-derived products, such as fatty alcohols, fatty aldehydes, fatty esters, hydrocarbons, triacylglycerides, lactones, phospholipids, etc. Preferably hydroxy fatty acids, fatty alcohols or fatty aldehydes.

This can be achieved by introduction of additional genes encoding the appropriate fatty acid modification activity. For example, conversion of fatty acids to fatty alcohols can be facilitated by expression of a fatty acyl-CoA reductase (FAR; EC 1.2.1.84). Conversion of fatty acids to hydroxy fatty acids can be achieved by expression of a fatty acid hydratase (EC 4.2.1.53) or a fatty acid hydroxylase (EC 1.11.2.4, EC 1.14.14.1, EC 1.14.15.12 or EC 1.14.15.3). Conversion of fatty acids to branched-chain fatty acids can be achieved by expression of a fatty acid methyltransferase. Conversion of fatty acids to epoxy fatty acids can be achieved by expression of a peroxygenase (EC 1.11.2.3). Conversion of free fatty acids to fatty aldehydes can be achieved by expression of carboxylic acid reductase (CAR; EC 1.2.99.6), while conversion of fatty acyl-CoAs to fatty aldehydes can be achieved by expression of an aldehyde-forming fatty acyl-CoA reductase (EC 1.2.1.50).

In some embodiments the fungal cell is genetically modified to increase the production of unsaturated fatty acids. This can be achieved by overexpressing a desaturase, for example, a fatty acyl-CoA desaturase. Examples of desaturases can include: a delta 3 desaturase, delta 4 desaturase, delta 5 desaturase, delta 6 desaturase, delta 7 desaturase, delta 8 desaturase, delta 9 desaturase, delta 10 desaturase, delta 11 desaturase, delta 12 desaturase, delta 13 desaturase, delta 14 desaturase, delta 15 desaturase, delta 16 desaturase and delta 17 desaturase. In some embodiments the desaturase might have a bifunctional or trifunctional activity with any combination of the above.

In some embodiments, a fungal cell comprises of overexpression of at least one exogenous or endogenous gene encoding a transport protein to facilitate increased secretion of fatty acids or fatty acid derived products into the media. The transport protein can be selected from the group consisting of an ATP-binding cassette (ABC) protein, a lipid transfer protein (LTP), a fatty acid transporter protein (FATP) and a plant wax ester transporter, preferably selected from the group consisting of ABCG11, ABCG12, LTPG1 and/or LTPG2. For example, ABC transporters of *Arabidopsis* such as ABCG11 and/or ABCG12 as well as lipid transfer proteins (LTPs) such as LTPG1 and LTPG2 can be introduced into a host cell. In some embodiments, fatty acid transporter (FATP) genes from species including *Saccharomyces, Drosophila, Mycobacteria*, or mammalian species can be introduced into a host cell. In some embodiments, the transporter protein increases the amount of fatty acids or fatty acid derived products such as fatty alcohols, fatty aldehydes, fatty esters, hydrocarbons, triacylglycerides, hydroxy fatty acids, dicarboxylic fatty acids, branched chain fatty acids, epoxy fatty acids or lactones, released into the growth media of a microorganism. Preferred transport proteins include FATP1 from *Homo sapiens* (Genbank: NP_940982; XP_352252), FATP4 from *Homo sapiens* (Genbank; NP_005085), and FAT1 from *S. cerevisiae* (Genebank: NP_009597). Expression of a transporter protein can in some embodiments also increase production of fatty acids or fatty acid derived products by a host strain. In a preferred embodiment, expression of FATP1 from *Homo sapiens* (Genbank: NP_940982) or another mammalian source in *S. cerevisiae* or *Y. lipolytica* facilitates the export into the growth medium of fatty acids or fatty acid derived products such as fatty alcohols, fatty aldehydes, fatty esters, hydrocarbons, triacylglycerides, hydroxy fatty acids, dicarboxylic fatty acids, branched chain fatty acids, epoxy fatty acids or lactones. In another preferred embodiment, expression of FATP4 from *Homo sapiens* (Genbank; NP_005085) or another mammalian source in *S. cerevisiae* or *Y. lipolytica* facilitates the export into the growth medium of fatty acids or fatty acid derived products such as fatty alcohols, fatty aldehydes, fatty esters, hydrocarbons, triacylglycerides, hydroxy fatty acids, dicarboxylic fatty acids, branched chain fatty acids, epoxy fatty acids or lactones. In yet another preferred embodiment overexpression of FAT1 from *S. cerevisiae* Genebank: NP_009597) in *S. cerevisiae* or *Y. lipolytica* facilitates the export into the growth medium of fatty acids or fatty acid derived products such as fatty alcohols, fatty aldehydes, fatty esters, hydrocarbons, triacylglycerides, hydroxy fatty acids, dicarboxylic fatty acids, branched chain fatty acids, epoxy fatty acids or lactones. Expression/overexpression of transporter proteins to increase secretion/production of fatty acids or fatty acid derived products such as fatty alcohols, fatty aldehydes, fatty esters, hydrocarbons, triacylglycerides, hydroxy fatty acids, dicarboxylic fatty acids, branched chain fatty acids, epoxy fatty acids or lactones, can be combined with any of the embodiments outlines above, or be completely independent.

In an embodiment, the fungal cell is capable of producing more than 100 mg of fatty acids per L of culture medium, and/or more than 10 mg of fatty acids per g dry cell weight (DCW).

In a particular embodiment, the fungal cell is capable of producing more than 250 mg, preferably more than 500 mg, and more preferably more than 750 mg, such as more than 1 g of fatty acids per L of culture medium.

In an alternative or additional particular embodiment, the fungal cell is capable of producing more than 15 mg, preferably more than 25 mg, and more preferably more than 30 mg fatty acid per g CDW.

The above described embodiments may be combined.

Other aspects of the invention provide methods for the production of fatty acids and/or fatty acid-derived products. Such methods comprises culturing a fungal cell according to any of the embodiments in a culture medium and in culture conditions suitable for production of the fatty acid and/or fatty acid-derived product by the fungal cell. The method also comprises collecting the fatty acid and/or fatty acid-derived product from the culture medium and/or the fungal cell.

The fatty acid-derived product is preferably selected from the group consisting of fatty alcohols, fatty aldehydes, fatty esters, hydrocarbons, triacylglycerides, lactones, phospholipids and a mixture thereof, preferably from the group consisting of fatty alcohols, fatty aldehydes, fatty esters, and a mixture thereof, and more preferably from the group consisting of hydroxy fatty acids, fatty alcohols, fatty aldehydes, and a mixture thereof.

In an embodiment, the culture medium is nitrogen-limited.

In an embodiment, the production process is composed of a growth phase, where the fungal cell is cultivated in the presence of high levels of the carbon source, e.g., glucose, and a production phase, where the fungal cell is cultivated in limiting conditions of the carbon source. This can be achieved, for example in a fed-batch process.

EXAMPLES

Example 1: Metabolic Engineering of the Acetyl-CoA Supply Results in High Production of Free Fatty Acids (FFA) in Fungal Cells This example shows that fatty acid production in a fungal cell can be increased by improving the conversion of pyruvate to acetyl-CoA through novel modifications in the acetyl-CoA metabolism. In particular, mitochondrial citrate synthesis was enhanced. The resulting citrate could be used by the enzyme ATP:citrate lyase (ACL), which cleaves citrate to oxaloacetate and acetyl-CoA. Acetyl-CoA is in turn used for the production of fatty acids. Acetyl-CoA Carboxylase (ACC) catalyzes the first step in fatty acids formation from acetyl-CoA.

Genetic modifications in yeast were carried out via promoter replacement, deletion of genes and integration of expression cassettes. Standard molecular biology methods were used, including the use of integration cassettes, use of the selective markers Ura, His and Kanamycin and marker loop out as described in David and Siewers, 2015.

As background yeast strain the strain YJZ45 (CEN.PK 113-110 (MATa; MAL2-8c; SUC2; his3Δ1; ura3-52; hfd1Δ; pox1Δ; faa1Δ; faa4Δ; ura3Δ:HIS3+MmACL+RtME+CTP1+'MDH3+tTesA+'lesA; URA3Δ::RtFAS1+RtFAS2+amdSym)) was used. Genetic modifications included promoter replacement in front of various genes including PYC1 (from −200 bp to 0 bp), ACC1 (from −481 bp to 0 bp), MP3, MP2, YHM2 replacing the native promoter with the constitutive active TEF1, PGK1 and TPI promoter, respectively. Heterologous expression of AnACL and RtCIT1 was facilitated via genomic integration of GAL1p-ACLa and GAL10p-ACLb, and HXT7p-RtCIT1 expression cassettes.

Yeast strains for preparation of competent cells were cultivated in YPD consisting of 10 g/L yeast extract (Merck Millipore, Billerica, Mass., USA), 20 g/L peptone (Difco) and 20 g/L glucose (Merck Millipore). Constructed plasmids and integration cassettes were transformed into respective yeast strains via the Lithium acetate method as previously described (Gietz et al., 2007). Strains containing URA3-based plasmids or cassettes were selected on synthetic complete media without uracil (SC-URA), which consisted of 6.7 g/L yeast nitrogen base (YNB) without amino acids (Formedium, Hunstanton, UK), 0.77 g/L complete supplement mixture without uracil (CSM-URA, Formedium), 20 g/L glucose (Merck Millipore) and 20 g/L agar (Merck Millipore). The URA3 maker was removed and selected against on 5-FOA plates, which contained 6.7 g/L YNB, 0.77 g/L CSM-URA and 0.8 g/L 5-fluoroorotic acid. Shake flask batch fermentations for production of free fatty acids were carried out in minimal medium containing 2.5 g/L $(NH4)_2SO_4$, 14.4 g/L $KH_2PO_4$, 0.5 g/L $MgSO_4.7H_2O$, 30 g/L glucose, trace metal and vitamin solutions supplemented with 60 mg/L uracil if needed. Cultures were inoculated, from 24 h precultures, at an initial $OD_{600}$ of 0.1 with 15 ml minimal medium in 100 mL unbaffled flask and cultivated at 200 rpm, 30° C. for 72 h. Glucose feed beads (SMFB63319, Kuhner Shaker, Basel, Switzerland) with a release rate of 0.25 g/L/h were added to the medium to replace the 30 g/L glucose if needed, and the culture time is 80 h for totally release the glucose. For nitrogen restricted culture, 1.4 g/L $(NH4)_2SO_4$ were used.

FFA titers in whole-cell culture (only FFA was measured in this study) were quantified following previously published methods (Zhou et al., 2016). Specifically, 0.2 ml of cell culture (or an appropriate volume of cell culture diluted to 0.2 ml) were transferred to glass vials from 72 h or 80 h incubated cultures, then 10 ml 40% tetrabutylammonium hydroxide (base catalyst) was added immediately followed by addition of 200 ml dichloromethane containing 200 mM methyl iodide as methyl donor and 100 mg/L pentadecanoic acid as an internal standard. The mixtures were shaken for 30 min at 1,200 rpm by using a vortex mixer, and then centrifuged at 4,000×g to promote phase separation. A 150 ml dichloromethane layer was transferred into a GC vial with glass insert, and evaporated 3 h to dryness. The extracted methyl esters were resuspended in 150 ml hexane and then analyzed by gas chromatography (Focus G C, Thermo Fisher Scientific) equipped with a Zebron ZB-5MS GUARDIAN capillary column (30 m×0.25 mm×0.25 mm, Phenomenex) and a DSQII mass spectrometer (Thermo Fisher Scientific). The GC program was as follows: initial temperature of 40° C., hold for 2 min; ramp to 130° C. at a rate of 30° C. per minute, then raised to 280° C. at a rate of 10° C. per min and hold for 3 min. The temperatures of inlet, mass transfer line and ion source were kept at 280, 300 and 230° C., respectively. The injection volume was 1 µl. The flow rate of the carrier gas (helium) was set to 1.0 ml/min, and data were acquired at full-scan mode (50-650 m/z). Final quantification was performed using the Xcalibur software.

The extracellular glucose, glycerol, ethanol and organic acid concentrations were determined by high-performance liquid chromatography analysis. In detail, a 1.5 ml broth sample was filtered through a 0.2 mm syringe filter and analyzed on an Aminex HPX-87G column (Bio-Rad) on an Ultimate 3000 HPLC (Dionex Softron GmbH). The column was eluted with 5 mM $H_2SO_4$ at a flow rate of 0.6 ml/min at 45° C. for 26 min.

Figure 2A:
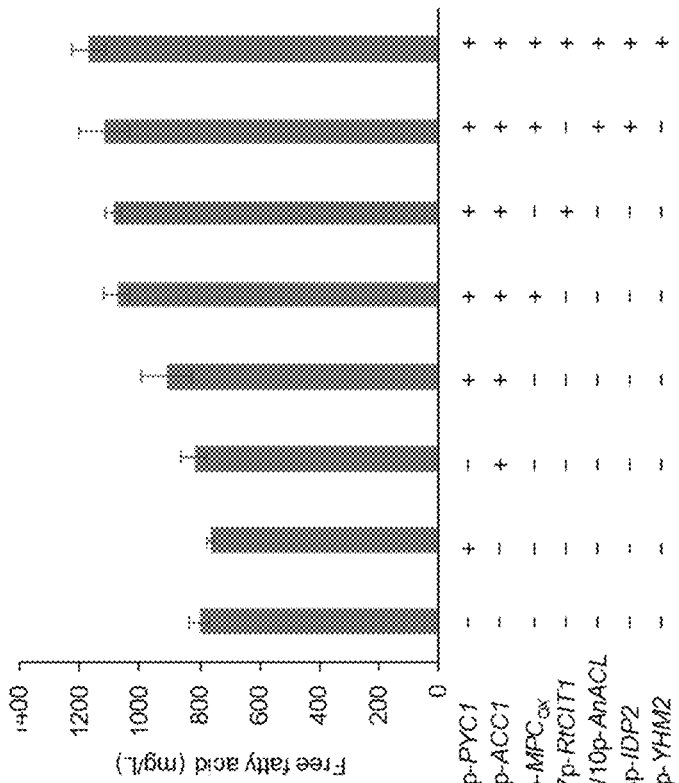
FIGS. 2A-2B: Metabolic engineering for enhancing the supply of the cytosolic acetyl-CoA. (A) Schematic illustration of the subcellular flux trafficking and engineering targets. (B) FFA production obtained with engineered strains in shake flasks after 72 h cultivation at 200 rpm, 30° C. on 30 g/L glucose. All data is presented as mean±SD of biological triplicates.
Figure 2B:
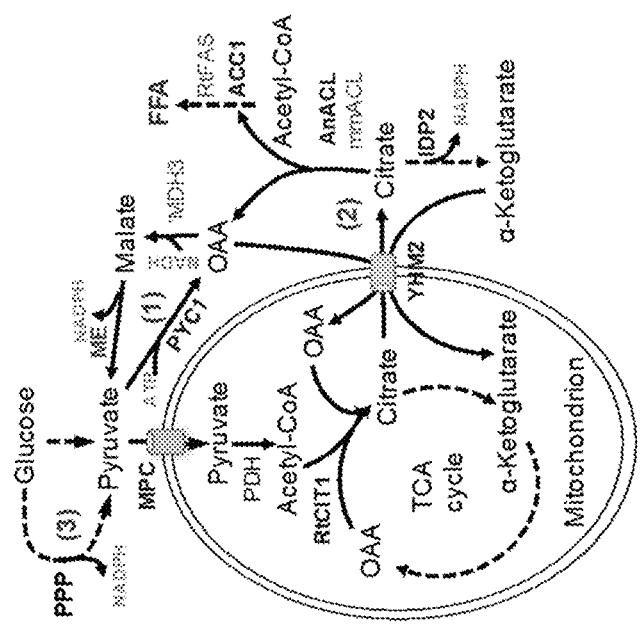

Overexpression of pyruvate carboxylase (PYC1) to ensure efficient formation of oxaloacetate required for citrate production did not result in a significant increase in FFA production (FIG. 2B). Neither did overexpression of acetyl-CoA carboxylase (ACC1) (FIG. 2B). However, combination of both modifications surprisingly resulted in a 14% increase in production of free fatty acids (FIG. 2B). When MPC1 and MPC3 (which together form the $MPC_{ox}$ pyruvate transport complex) were overexpressed in a strain overexpressing PYC1 and ACC1 in order to improve transport of pyruvate to the mitochondria, a further 17% improvement in production was observed (FIG. 2B). When citrate synthase from *Rhodosporidium toruloides* (RtCIT1) was overexpressed in a strain overexpressing PYC1 and ACC1, a further 18% improvement in fatty acid titers was observed compared to the parental strain (FIG. 2B). Combining overexpression of PYC1, ACC1, MPC1, MPC3 and YHM2 with heterologous expression of AnACL and RtCIT1 lead to a 256% increase in FFA production compared to a strain only overexpressing PYC1 and ACC1, and a 46% improvement compared to the starting strain (FIG. 2B).

Example 2: Further Fine-Tuning of Gene Expression Improves Free Fatty Acid (FFA) Production by Fungal Cells Additional engineering was done through fine tuning of gene expression of the gene PGI1 (from −405 bp to 0 bp) involved in glycolysis and IDH2 (from −456 bp to 0 bp) in TCA cycle through promoter replacement with promoters displaying lower activity. All genetic modifications, cultivations, and analysis were performed as described in Example 1.

For PGI1, the promoter replacement was done through integration cassettes with the promoters of ISU1 (SEQ ID NO: 15), ATP14 (SEQ ID NO: 16), QCR10 (SEQ ID NO: 17), COX9 (SEQ ID NO: 18), NAT1 (SEQ ID NO: 19) and HXT1 (SEQ ID NO: 20), which were amplified from CEN.PK113-5D genomic DNA. Additionally integration cassettes were constructed for overexpression of Pentose Phosphate Pathway associated genes, including: $P_{HXT1}$-TKL1, $P_{PGK1}$-TAL1, $P_{TEF1}$-ZWF1, $P_{TDH3}$-GND1.

Figure 3A:
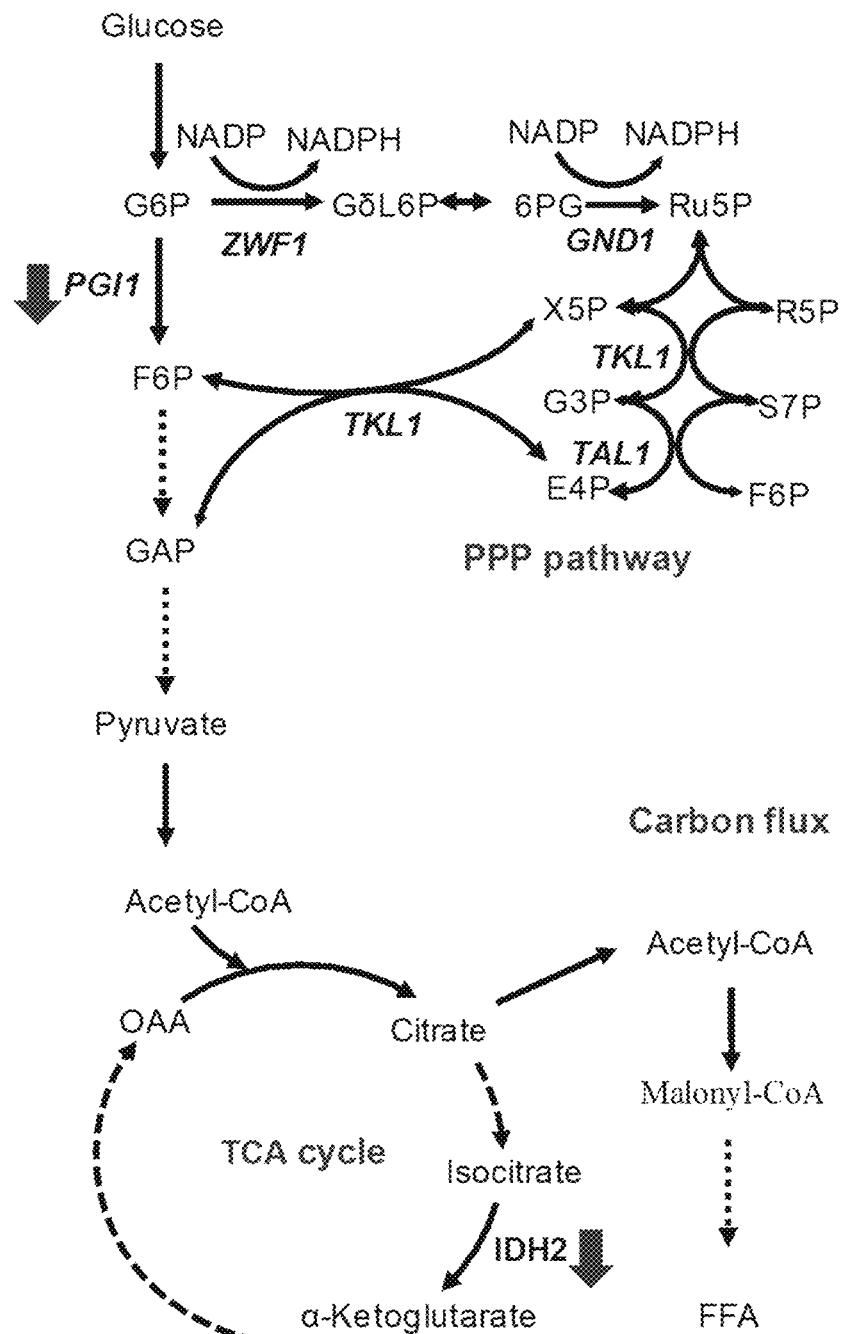
FIGS. 3A-3C: Fine-tuning the pentose phosphate pathway (PPP), tricarboxylic acid cycle (TCA) cycle and glycolysis for FFA production. (A) Schematic illustration of metabolic connections between glycolysis, TCA cycle and PPP. Pushing carbon flux into PPP for improving FFA production by tuning PGI1 and IDH2 expression. Fine tuning of PGI1 (B) and IDH2 (C) improved FFA production up to 60%. The strains were cultivated in shake flasks for 80 h at 200 rpm, 30° C. with glucose feed beads corresponding to 30 g/L glucose. All data represent the mean±s.d. of biological triplicates.
Figure 3B:
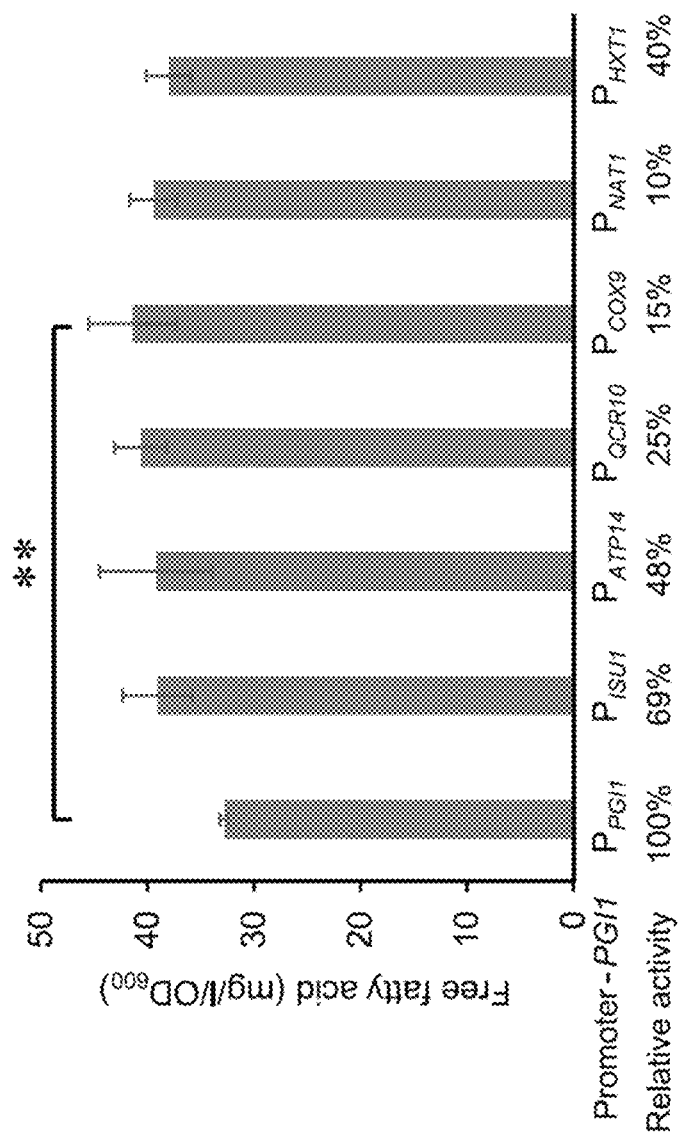

Replacing the native promoter of PGI1 with a weaker promoter increased FFA production by 20-27%, with the COX9 promoter displaying the best results (FIG. 3B).

Figure 3C:
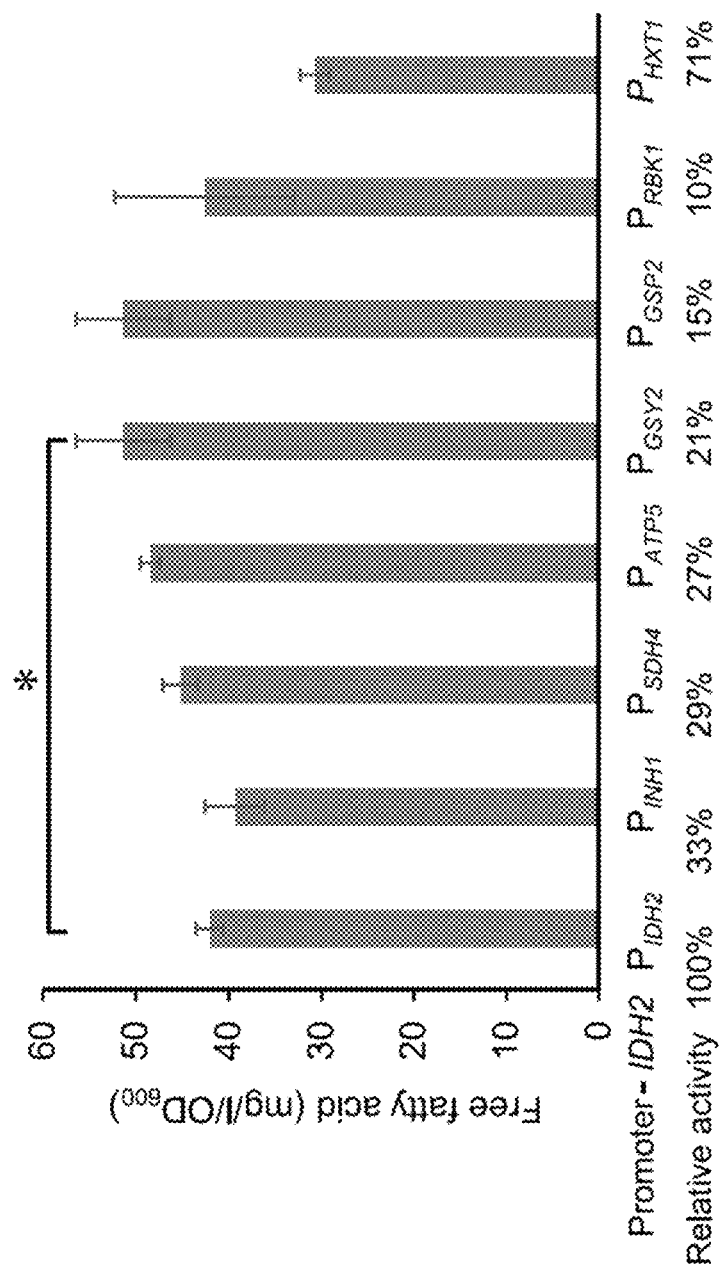

For IDH2, the promoter replacement was done through integration cassettes with the promoters of INH1 (SEQ ID NO: 21), SDH4 (SEQ ID NO: 22), ATPS (SEQ ID NO: 23), GSY2 (SEQ ID NO: 24), GSP2 (SEQ ID NO: 25), RBK1 (SEQ ID NO: 26) and HXT1 (SEQ ID NO: 20), which were amplified from CEN.PK113-5D genomic DNA. Replacing the native promoter of IDH2 with a weaker promoter increased FFA production by up to 22%, with the GSY2 and GSP2 promoters displaying the best results (FIG. 3C).

The resulting strain TY36 having the following genetic background: MATa; MAL2-8c; SUC2; his3Δ1; ura3-52; hfd1Δ; pox1Δ; faa1Δ; faa4Δ; ura3Δ::HIS3+MmACL+RtME+CTP1+'MDH3+tTesA+'tesA; URA3Δ::RtFAS1+RtFAS2+amdSym; acc1::TEF1p-ACC1; pyc1::TEF1p-PYC1; X1-4::MPC1+MPC3; gal80Δ; X1-2::AnACL; gal1Δgal7Δgal10Δ::RtCIT1+IDP2+YHM2; pgi1Δ::COX9p-PGI1+GND1+TKL1+TAL1+ZWF1; idh2Δ::GSY1p-IDH2, which combined all modifications was tested under fed-batch conditions (see Example 3).

Example 3: Growth-Production De-Coupling

Figure 4:
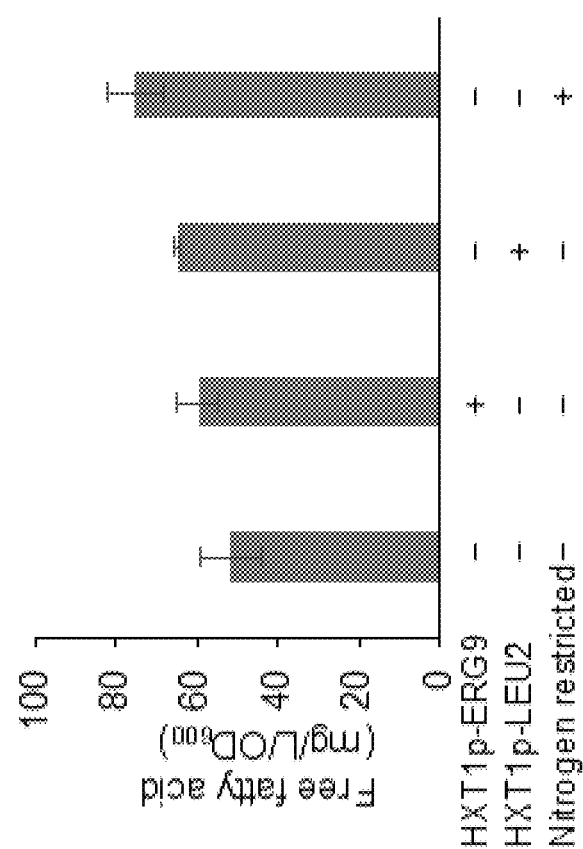
FIG. 4: FFA production was further improved by growth decoupling. Limited cell growth by downregulation of essential genes and nitrogen restriction improved FFA production. The strains were cultivated in shake flasks for 80 h at 200 rpm, 30° C. with glucose feed beads (corresponding to 30 g/L glucose). All data represent the mean±SD of biological triplicates.

In oleaginous fungi, lipid overproduction is always initiated by growth stagnation that is triggered by limitation of nutrients such as nitrogen, which is due to the fact that biomass formation competes for carbon and energy. We therefore decoupled FFA production from cell growth through limiting cell growth by dynamically controlling the expression of essential genes under the HXT1 promoter, whereby we can tune cell growth by controlling the glucose concentration. The native promoter of LEU2 (from −195 bp to 0 bp) and ERG9 (from −138 bp to 0 bp) were replaced by the HXT1 promoter using standard techniques involving integration cassettes, marker selection and removal as previously described in Example 1. Genetic modifications, cultivation and analytics were carried out as described in Example 1. The promoter replacement lead to 15% increase in free fatty acid production in case of the ERG9 promoter and 25% for the LEU2 promoter (FIG. 4). Cultivation of this particular strain without any promoter replacement regarding LEU2 and ERG9 but under nitrogen limitation lead to 47% increase in free fatty acid production (FIG. 4). A fed-batch cultivation of strain TY36 under nitrogen limiting conditions was carried out leading to very high titers of free fatty acids of 35 g/L (FIG. 5). The batch and fed-batch fermentations for free fatty acid production were performed in 1.0 L bioreactors, with an initial working volume of 0.25 L, in a DasGip Parallel Bioreactors System (DasGip). The initial batch fermentation was carried out in minimal medium containing 5 g/L $(NH4)_2SO_4$, 3 g/L $KH_2PO_4$, 0.5 g/L $MgSO_4.7H_2O$, 60 mg/L URA, 20 g/L glucose, trace metal and vitamin solutions. The temperature, agitation, aeration and pH were monitored and controlled using a DasGip Control 4.0 System. The temperature was kept at 30° C., initial agitation set to 800 rpm and increased to maximally 1,200 rpm depending on the dissolved oxygen level. Aeration was initially provided at 36 sl/h and increased to maximally 48 sl/h depending on the dissolved oxygen level. The dissolved oxygen level was maintained above 30%, the pH was kept at 5.6 by automatic addition of 4 M KOH and 2 M HCl. The aeration was controlled and provided by a DasGip MX4/4 module. The composition of the off-gas was monitored using a DasGip Off gas Analyzer GA4. Addition of the acid, base, and glucose feed was carried out with DasGip MP8 multi-pump modules (pump head tubing: 0.5 mm ID, 1.0 mm wall thickness). The pumps, pH and DO probes were calibrated before the experiment. During the fed-batch cultivation, the cells were initially fed with a 200 g/L glucose solution with a feed rate that was exponentially increased (µ=0.05/h) to maintain a constant biomass-specific glucose consumption rate. The used minimal medium contained 15 g/L $(NH_4)_2SO_4$, 9 g/L $KH_2PO_4$, 1.5 g/L $MgSO_4.7H_2O$, 180 mg/L uracil, 3×trace metal and 3×vitamin solution. When the volume of the fermentation broth reached 0.4-0.45 L, the feed solution was switched to the following composition: 25 g/L $(NH_4)_2SO_4$, 15 g/L $KH_2PO_4$, 2.5 g/L $MgSO_4.7H_2O$, 300 mg/L uracil, 600 g/L glucose, 5× trace metal and 5× vitamin solution. The initial feed rate was calculated using the biomass yield and concentration that were obtained during prior duplicate batch cultivations with these strains. The feeding was started once the dissolved oxygen level was higher than 30%. Dry cell weight measurements were performed by filtrating 3-5 ml of broth through a weighed 0.45 mm filter membrane (Sartorius Biolab, Gottingen, Germany) and measuring the weight increase after drying for 48 h in a 65° C. oven. The filter was washed once before and three times after filtrating the broth with 5 ml deionized water. During fermentation, floating dead cells and fatty acid residues were found to stick to the inner wall or the bottom of the fermenter. After fermentation, all particles were resuspended in the fermentation culture to accurately measure the total FFA production. Measurements were performed three times.

Example 4: Abolishment of Ethanol Production

Ethanol is often a side-product of fermentation and might be undesired if production of fatty acids is the main goal. Pyruvate decarboxylases (PDC1, PDC5, and PDC6) catalyze the decarboxylation of pyruvate to acetaldehyde, which plays a key role in alcoholic fermentation in S. cerevisiae. Deletion of these genes leads to abolishment of ethanol production. However, a PDC-negative strain with a triple deletion of all PDC genes is unable to grow on glucose as the sole carbon source.

Figure 6A:
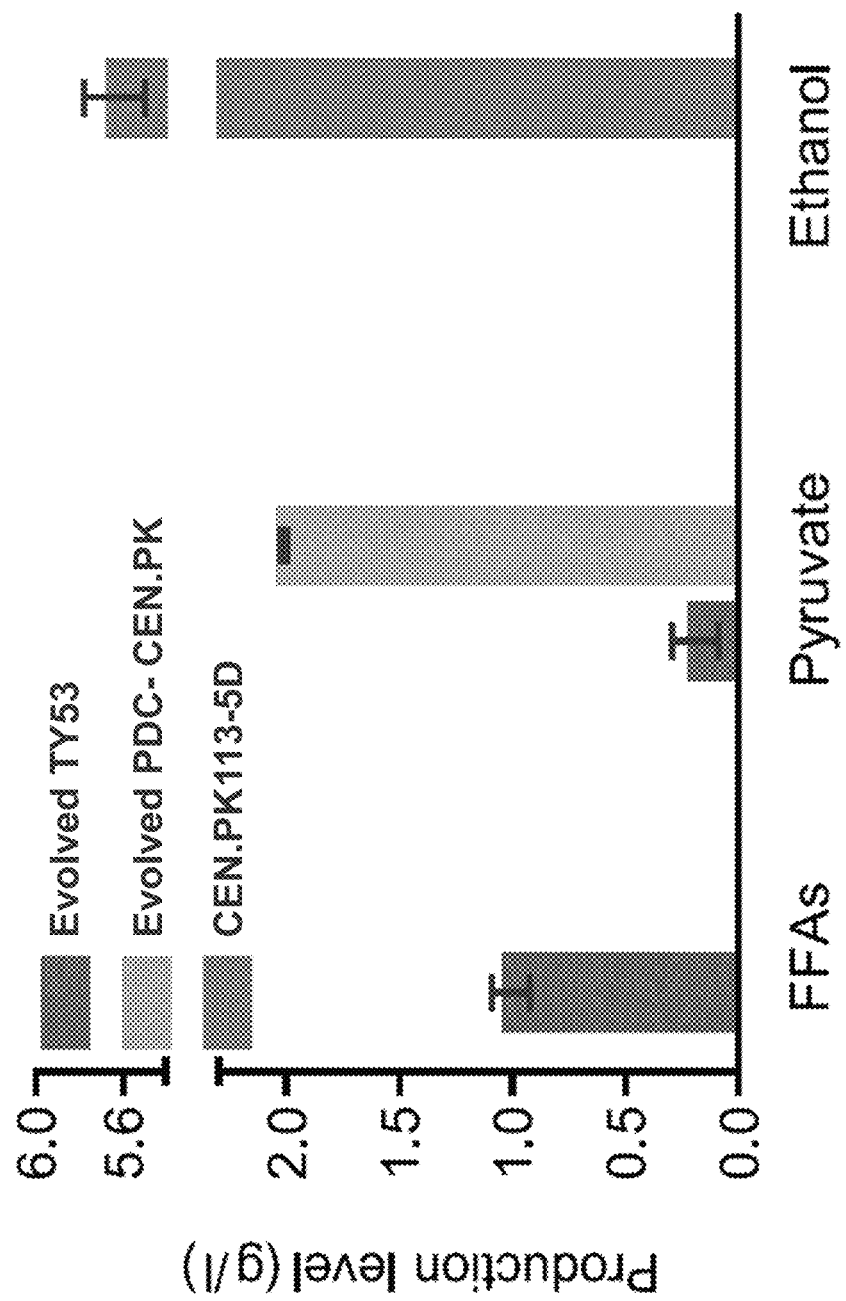
FIGS. 6A-6C: Rewiring yeast from alcoholic fermentation to fatty acid production. (A) The production profile of wild-type S. cerevisiae (CEN.PK113-5D), an evolved wild-type pyruvate dexarboxylase (PDC)-negative strain and the evolved TY53 strain. Strains were cultured in shake flasks at 200 rpm, 30° C. on 30 g/L glucose. All data represent the mean±SD of biological triplicates. (B) Free fatty acid production in fed-batch cultures of the evolved PDC-negative yeast with glucose limitation and nitrogen restriction. Circle indicates overall free fatty acid production at the end of fermentation. (C) Time-course for glucose consumption and dry cell weight accumulation during fed-batch fermentation of evolved pyruvate decarboxylase-negative yeast.
Figure 6B:
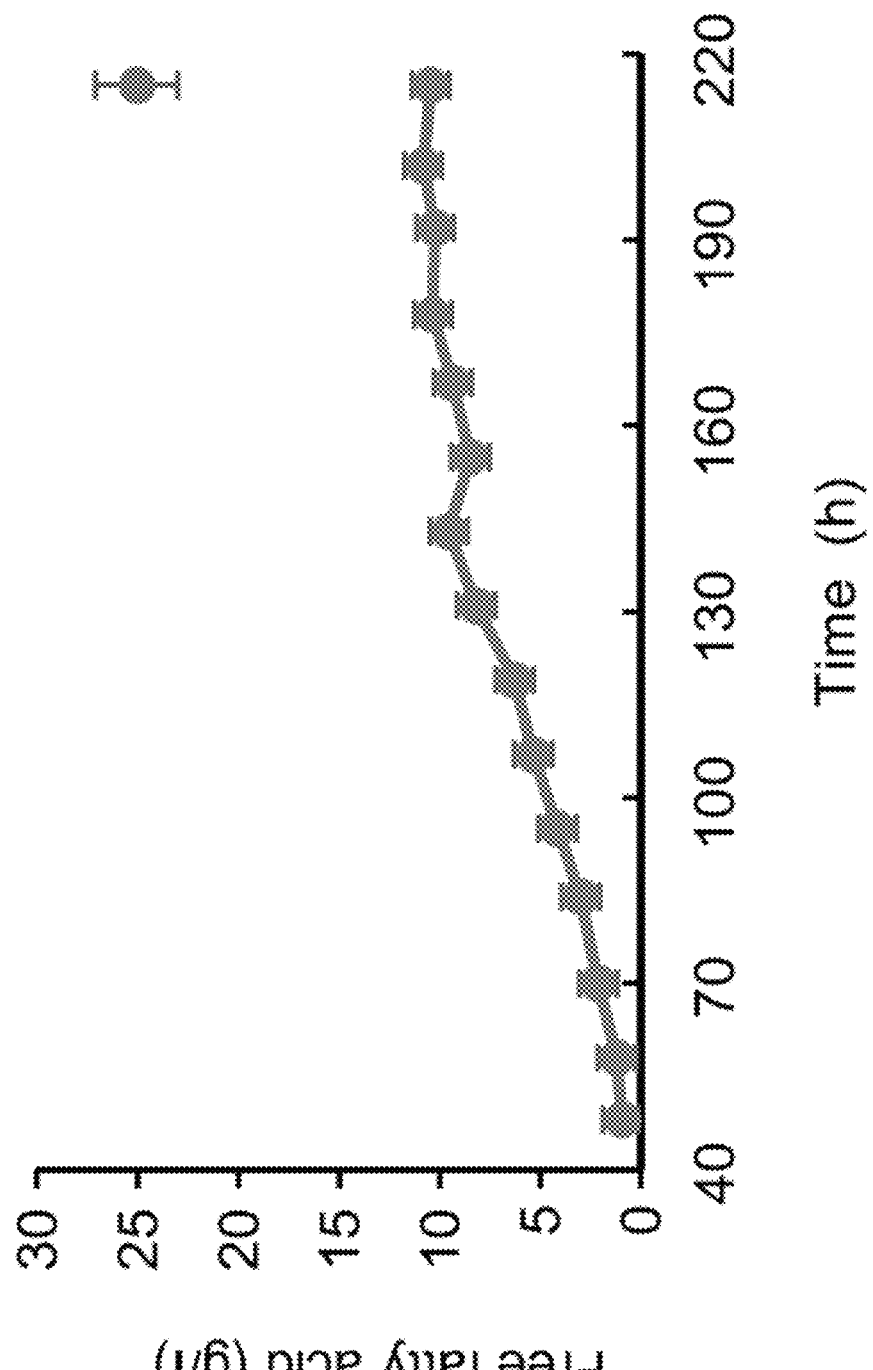
Figure 6C:
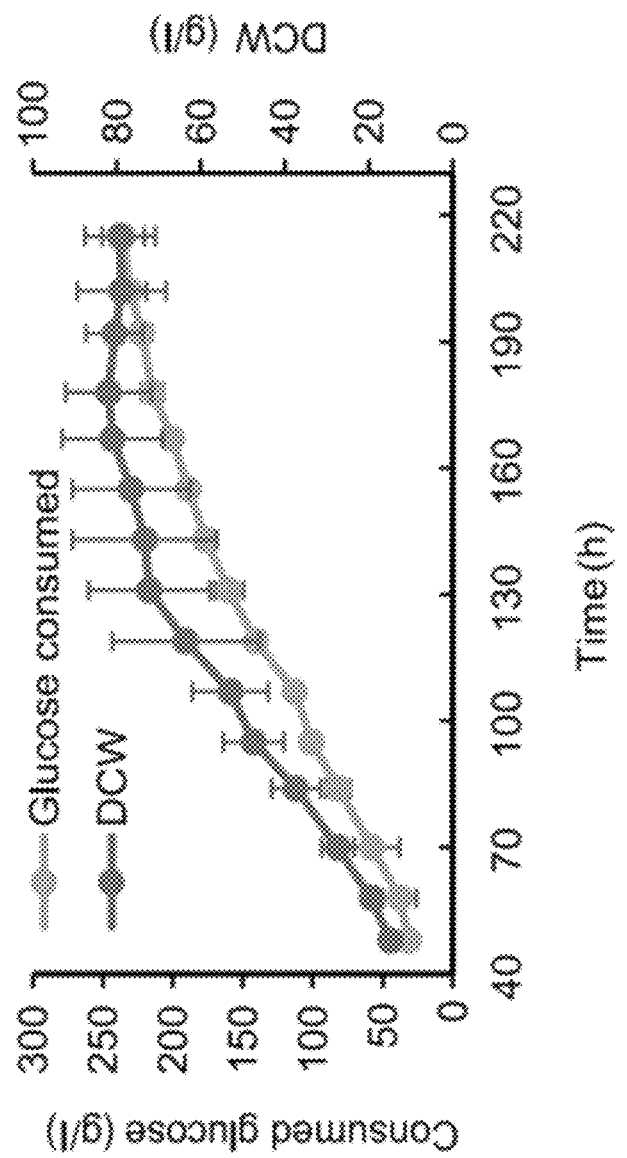

PDC1, PDC5 and PDC6 were deleted from the fatty acid-producing strain TY36 using the methodology outlined in Example 1, resulting in strain TY53. However, the resulting strain was unable to grow on glucose. In order to facilitate growth on glucose, the strain was evolved using Adaptive Laboratory Evolution. The adaptive evolution of TY53 (TY36 pdc1Δ, pdc5Δ, pdc6Δ) toward growth on glucose as the sole carbon source were performed in three independent culture lines in 100 mL shake flasks with 15 mL medium at 30 C, which involved two phases. In the first phase, strains were cultivated in minimal medium containing 0.5% glucose and 2% ethanol and then serially transferred every 48 or 72 h using minimal medium with a gradually decreased ethanol concentration and increased glucose concentration for 45 days. Subsequently, the strains were transferred into minimal medium containing 2% glucose as the sole carbon source and evolved for increased growth by serial transfer every 48 or 72 h for 50 days. Several strains were isolated from the evolved populations and tested. The evolved TY53 strains could grow on glucose. The performance of the evolved strains was compared to a wild-type strain (CEN.PK113-5D) and an evolved PDC-negative wild-type strain (evolved PDC-CEN.PK) (FIG. 6A). When cultured under shake-flask conditions (as described in Example 1), the evolved TY53 strains could produce fatty acids, produced less pyruvate than evolved PDC-CEN.PK and did not produce ethanol (FIG. 6A). When grown under fed-batch conditions (performed as described in Example 3) the strains produced up to 25 g/L of free fatty acids (FIG. 6B) and accumulated biomass (FIG. 6C)

To evaluate the underlying mechanisms, total genomic DNA of selected strains was extracted by using the Blood & Cell Culture DNA Kit (QIAGEN). Then DNA was prepared using the Illumina TruSeq Nano DNA HT 96 protocol, according to the manufacturer's instructions. The samples were sequenced using an Illumina NextSeq High kit, paired-end 300 cycles (2×150 bp). Each sample was represented by 2.2-6.4 million sequence reads. Breseq (Deatherage and Barrick, 2014) 0.30.2 with bowtie (Langmead and Salzberg, 2012) 2.2.8 was used to map the reads of each sample to the genome of S. cerevisiae CEN.PK 113-7D (Jenjaroenpun et al., 2018). The option junction-alignment-pair-limit set to 0 (no limit) to ensure all possible new junctions were evaluated. The sequencing data for the initial strain (TY36) was also processed with breseq and used as a reference for removing false-positives from the sample analysis.

Figure 7:
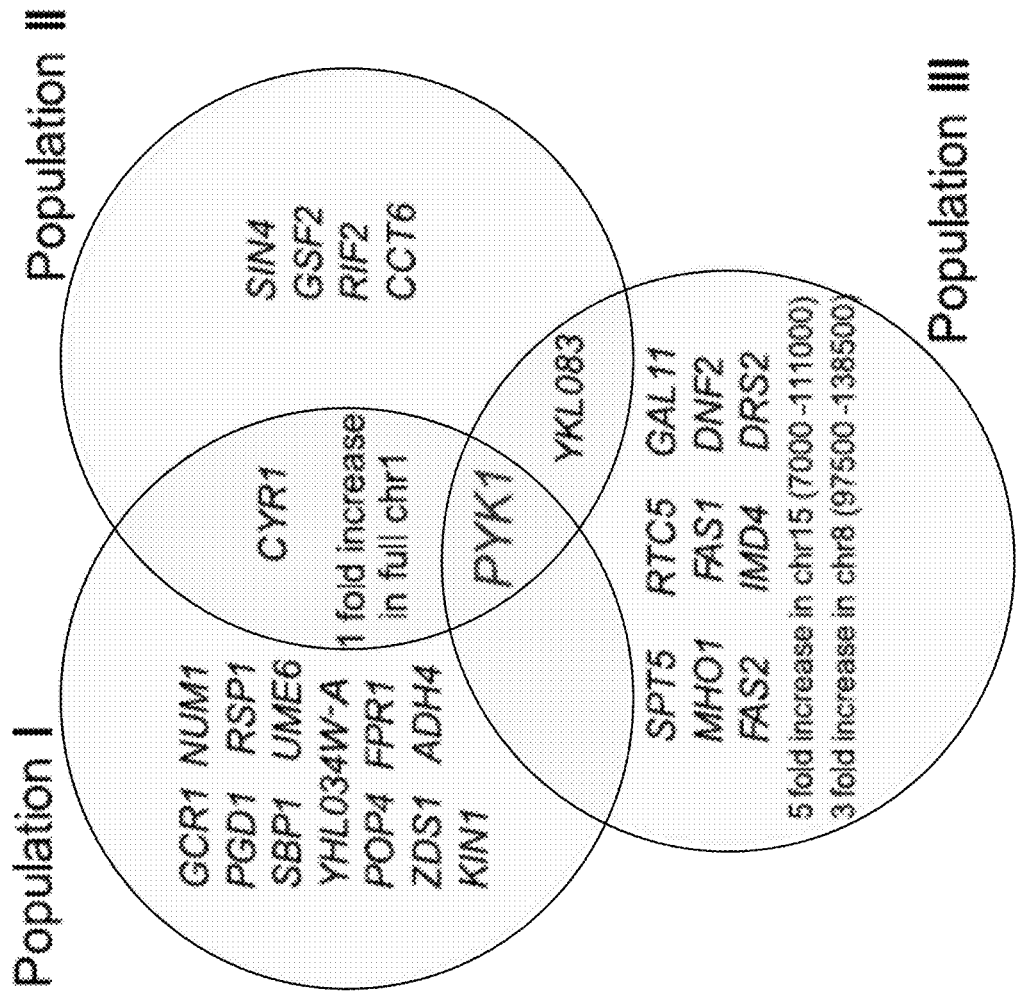
FIG. 7: Venn diagram summarizing the intersection among mutations accumulated in the evolved strains TY53 isolated from three distinct evolution experiments.
Figure 8:
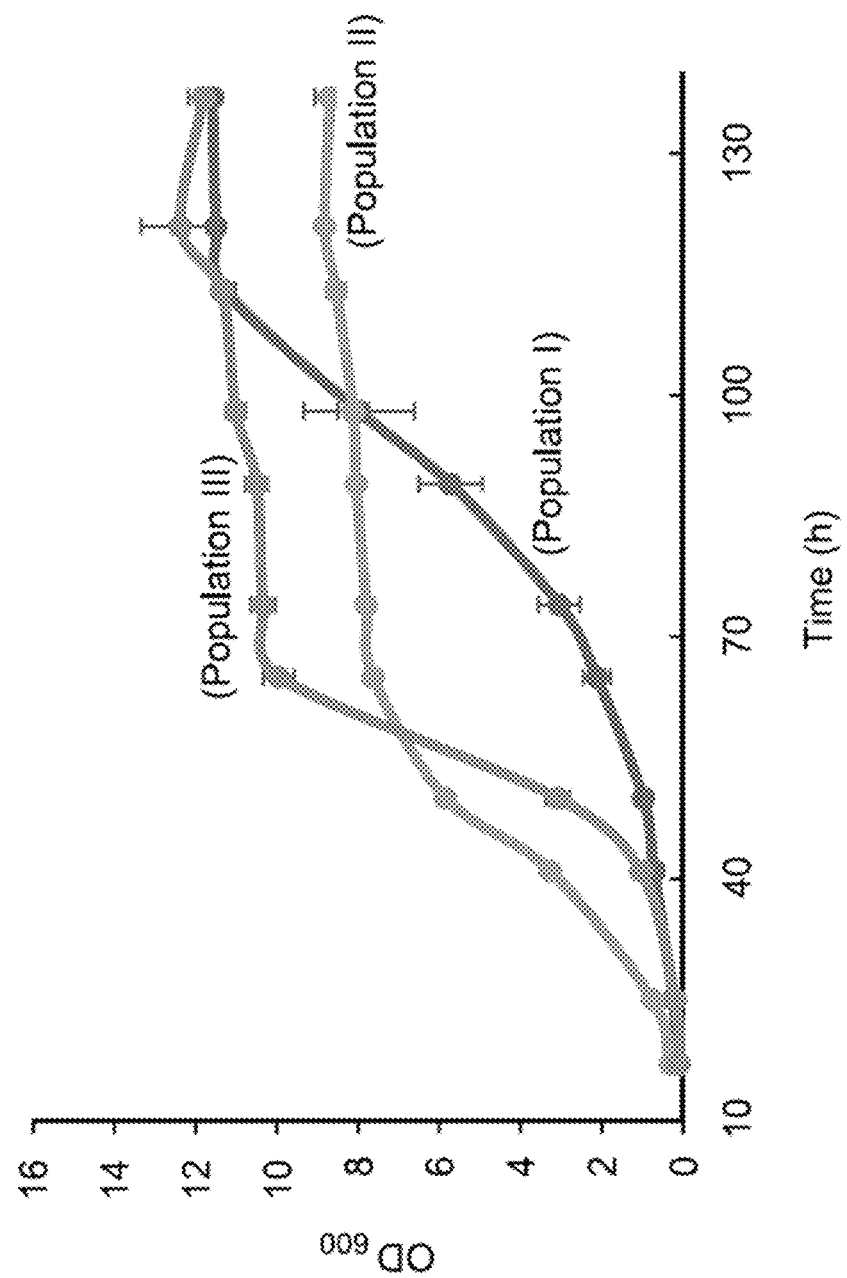
FIG. 8: Growth curves for the three evolved TY53 populations. The strains were cultured in shake flasks at 200 rpm, 30° C. with 20 g/L glucose. All data represent the mean±SD of biological triplicates.

The mutations found in the three clones are shown in FIG. 7. The growth of each clone (under shake-flask conditions, as described in Example 1) is shown in FIG. 8.

It was found that mutations in pyruvate kinase (PYK1), also known as CDC19 in S. cerevisiae, occurred in all three evolved clones: two nonsense mutations (R68* and K196*) and a missense mutation (R91I). PYK1 (CDC19) is the major pyruvate kinase which converts phosphoenolpyruvate (PEP) and ADP to pyruvate and ATP. PYK1 is tightly regulated and activated by fructose-1,6-bisphosphate (FBP) and considered as a key control point of glycolytic flux. The mutations in PYK1 across the evolved mutants suggested that decease in PYK1 activity is important for growth on glucose.

Figures 9A, 9B:
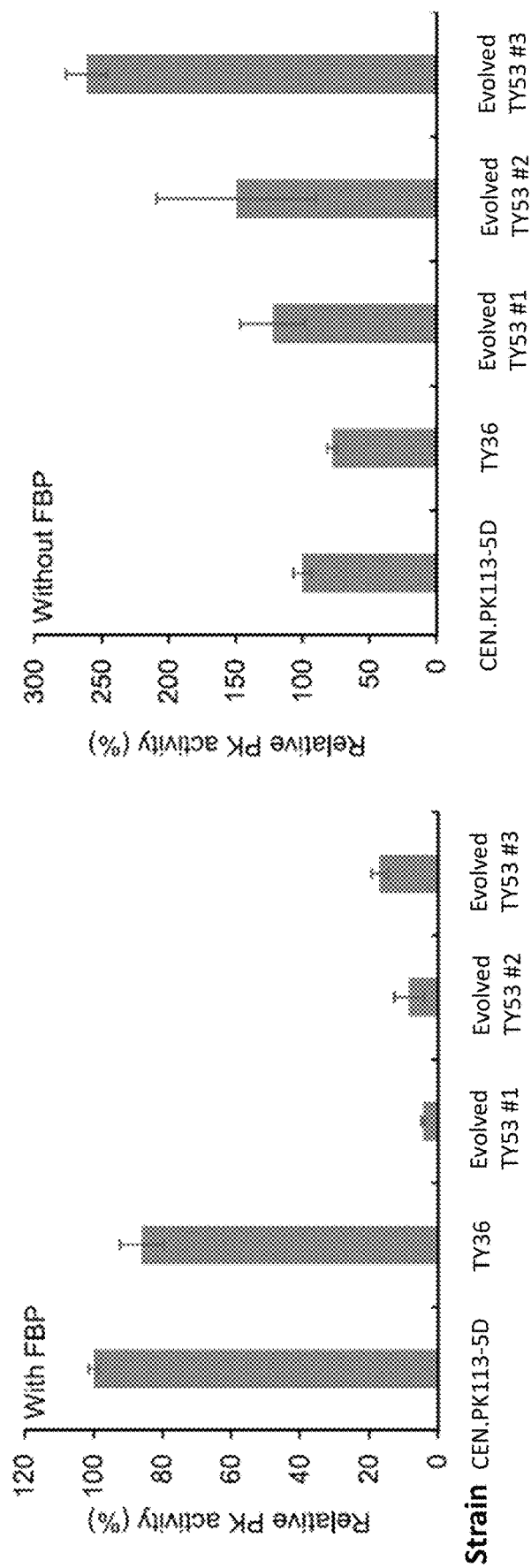
FIGS. 9A-9B: Activity of pyruvate kinase (PK). (A) The overall activity of PK in the evolved strains was downregulated. Fructose-1,6-bisphosphate (FBP) was added as an activator of PYK1. (B) The activity of PYK2 in the evolved strains was increased. Here, no FBP was added as an activator.
Figure 10:
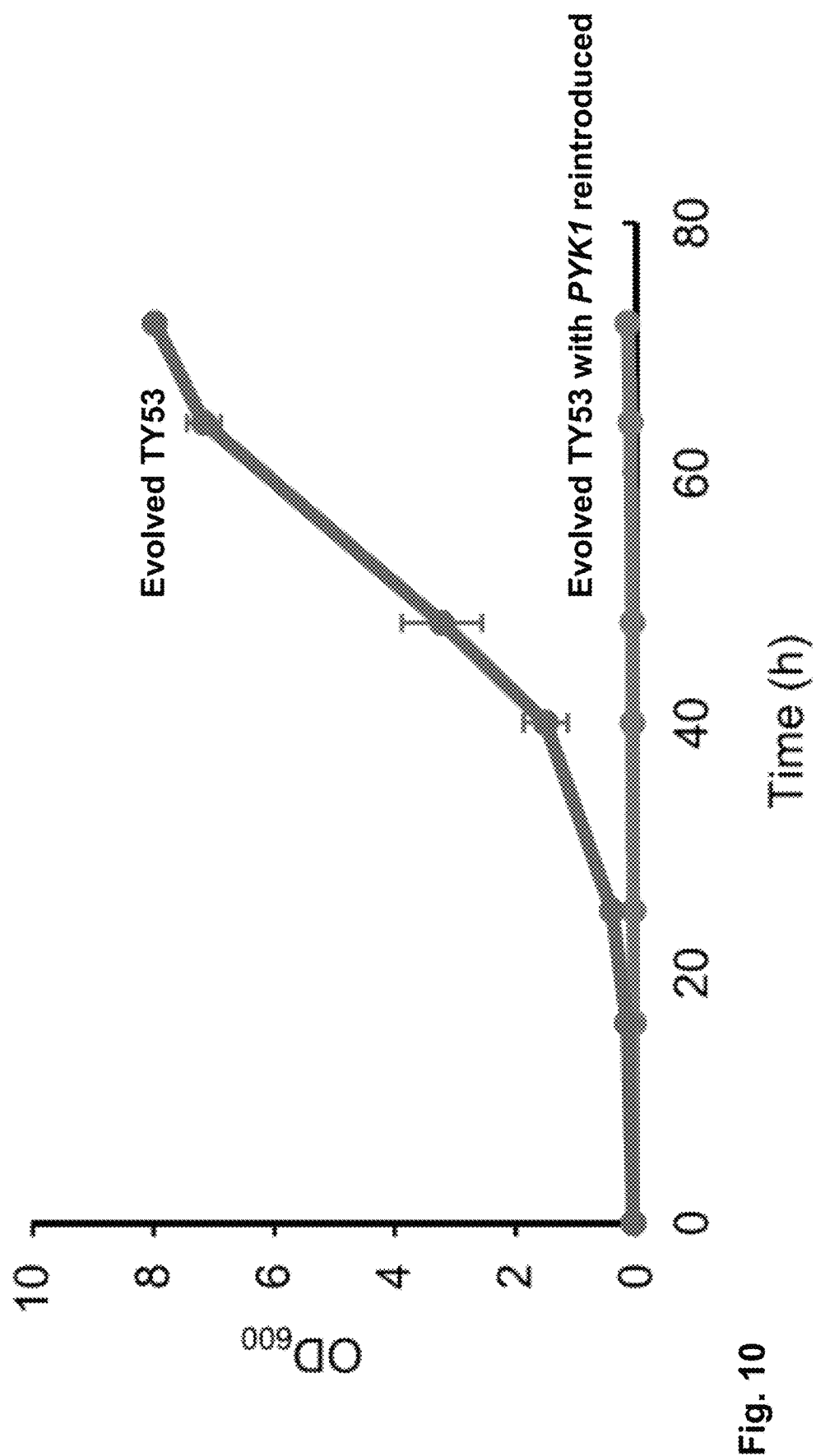
FIG. 10: The evolved phenotype was abolished by expression of PYK1. The strains were precultured in shake flasks at 200 rpm, 30° C. with 20 g/L glucose for 3 days to remove intracellular stores of C2 metabolites, then subcultured in shake flasks at 200 rpm, 30° C. with 20 g/L glucose for measurement of optical density at 600 nm ($OD_{600}$). All data represent the mean±SD of biological triplicates.
Figure 11:
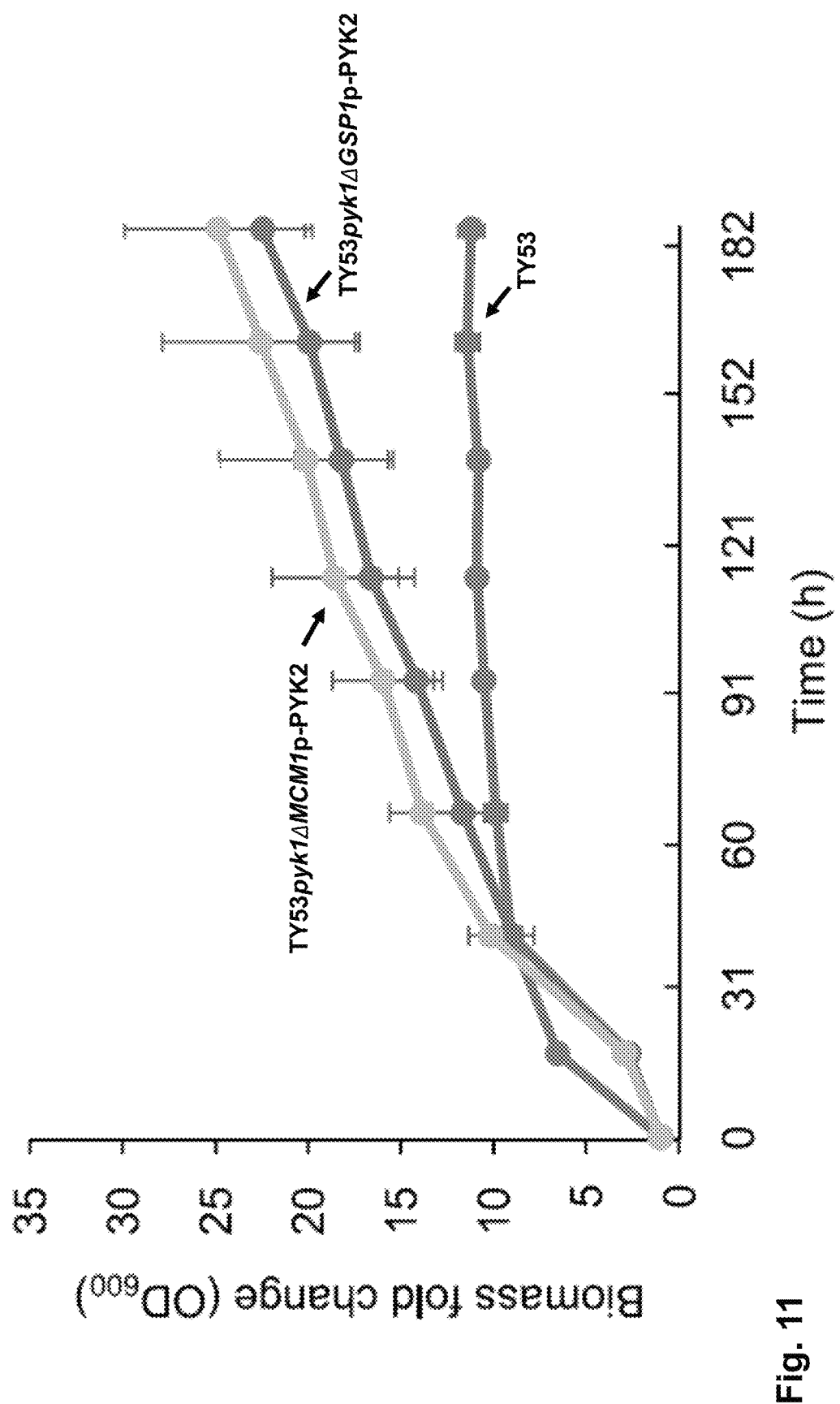
FIG. 11: Downregulation of FBP-sensitive and upregulation of FBP-insensitive pyruvate kinase enabled the growth of PDC-negative strain in high concentration of glucose. The strains were cultured in shake flasks at 200 rpm, 30° C. with 20 g/L glucose and 0.5% (v/v) ethanol. All data represent the mean±SD of biological triplicates. The activity of GSP1 promoter is 6-fold of native PYK2 promoter. The activity of MCM1 promoter is 3-fold of native PYK2 promoter. The PYK1 gene was deleted in TY53, then a PYK2 gene under the promoter of GSP1 or MCM1 in a low-copy plasmid was introduced into the cell to get the strain TY53 pyk1ΔGSP1p-PYK2 or TY53pyk1ΔMCM1p-PYK2.

In addition, it was found that while the evolved mutants had a much lower PYK activity in general, they had a higher PYK2 activity (FIG. 9) compared to the unevolved strain and PYK2 was found to be increased in copy number in the evolved strains. In order to confirm the role of PYK in growth on glucose, wild-type PYK1 was reintroduced into the evolved strain, which resulted in abolishment of growth in glucose medium (FIG. 10). In addition, we found that deletion of PYK1 and overexpression of PYK2 in the PDC-negative strain TY53 enabled growth on glucose (FIG. 11).

Overall, these results demonstrate that it is possible to abolish production of the by-product ethanol and maintain growth on glucose by deleting the PDC genes, down-regulating PYK1 and overexpressing PYK2.

Example 5: Overexpression of Endogenous Genes

This example demonstrates that increased production of fatty acids can be achieved through overexpression of selected endogenous genes.

The endogenous genes MPP6, ACP1, EPT1, FAA1, GEP4, GGA2, IDP3, INP54, LPP1, MCR1, ORM1, RTC3, SPO7, TGL1 and YFT2 were amplified from the genomic DNA of S. cerevisiae strain IMX581 (derived from the strain CEN.PK113-5D Mans et al., 2015). The genes were integrated into the integration site X_3 (Jessop-Fabre et al., 2016) in the background strain IMX581. Promoter PTEF1 and terminator TCYC1 were used for controlling gene expression of the selected genes. Amplified genetic parts, including homologous regions and promoter-gene-terminator, were assembled into a cassette through a two-step fusion PCR procedure adapted from (Zhou et al., 2012) and transformed into strain IMX581. This resulted in 15 *S. cerevisiae* strains, each overexpressing one of the following genes: MPP6, ACP1, EPT1, FAA1, GEP4, GGA2, IDP3, INP54, LPP1, MCR1, ORM1, RTC3, SPO7, TGL1 and YFT2.

The above strains, as well as a control strain (IMX581) not overexpressing any of the endogenous genes mentioned above, were inoculated from 48 h pre-cultures at an $OD_{600}$ of 0.1 in 25 mL minimal medium (described in Example 1) supplemented with 60 mg/L uracil in 100 mL shake flasks. Strains were cultivated at 30° C. at 200 rpm. Samples for fatty acid analysis were taken after 48 hours of cultivation and processed as described in Example 1.

Figure 12:
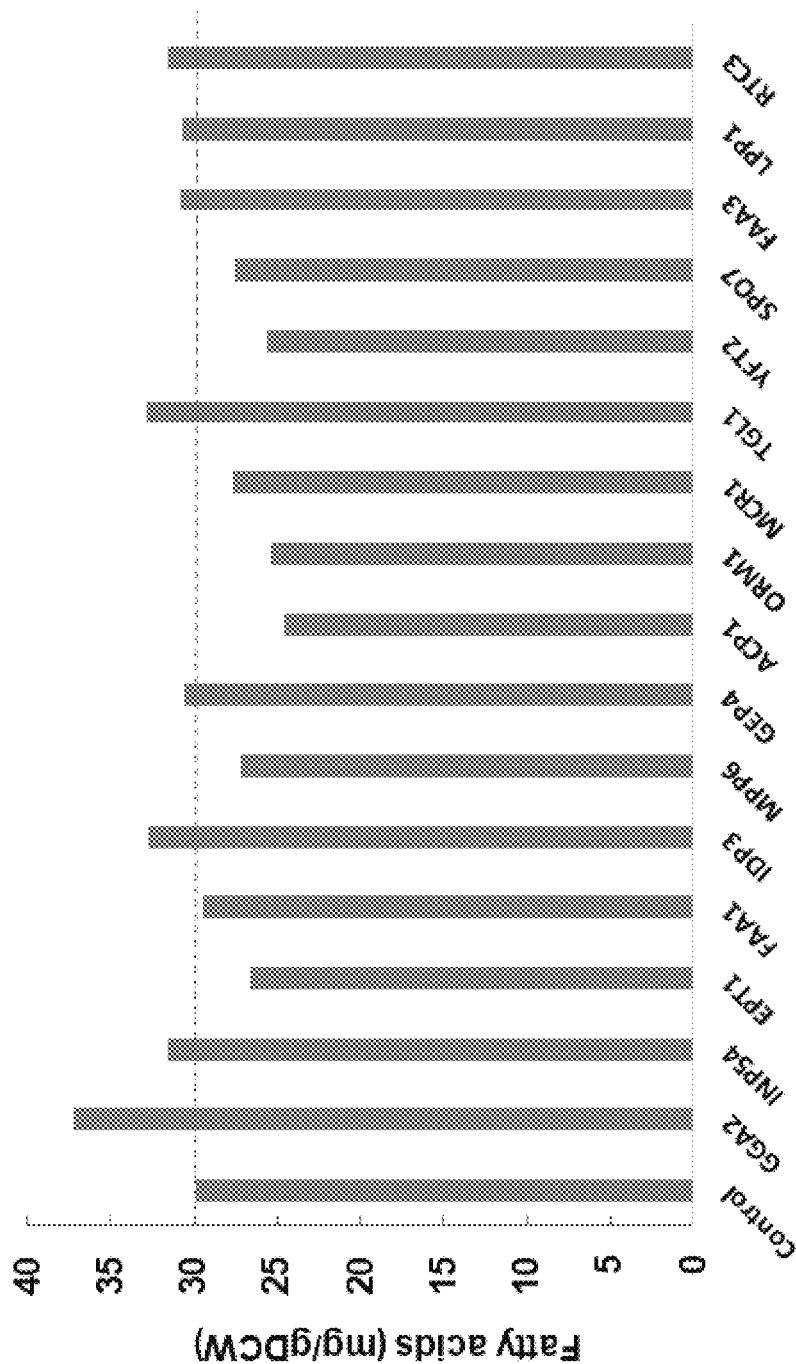
FIG. 12: Effect of individual overexpression of GGA2, INP54, EPT1, FAA1, IDP3, MPP6, GEP4, ACP1, ORM1, MCR1, TGL1, YFT2, SPO7, FAA3, LPP1 and RTC3 on production of fatty acids. IMX581 is the control strain (not overexpressing any of the aforementioned genes). Strains were cultivated at 30° C. and 200 rpm and samples were taken after 48 hours. All numbers are an average of three replicates. Dashed horizontal line indicates production of control strain for easier comparison.

FIG. 12 shows the results for total fatty acid production as a consequence of overexpression of the genes described above. Individual overexpression of GGA2, INP54, IDP3, GEP4, TGL1, FAA3, LPP1 and RTC3 showed a beneficial effect on fatty acid production. Strains overexpressing these genes displayed improved fatty acid production of 24.4%, 5.5%, 9.3%, 2.1%, 9.8%, 2.8%, 2.5% and 5.6% compared to the control strain, respectively (FIG. 12). These results show that overexpression of these genes is a good strategy to improve production of fatty acids in yeast, with overexpression of GGA2 being the most promising strategy.

Figure 13:
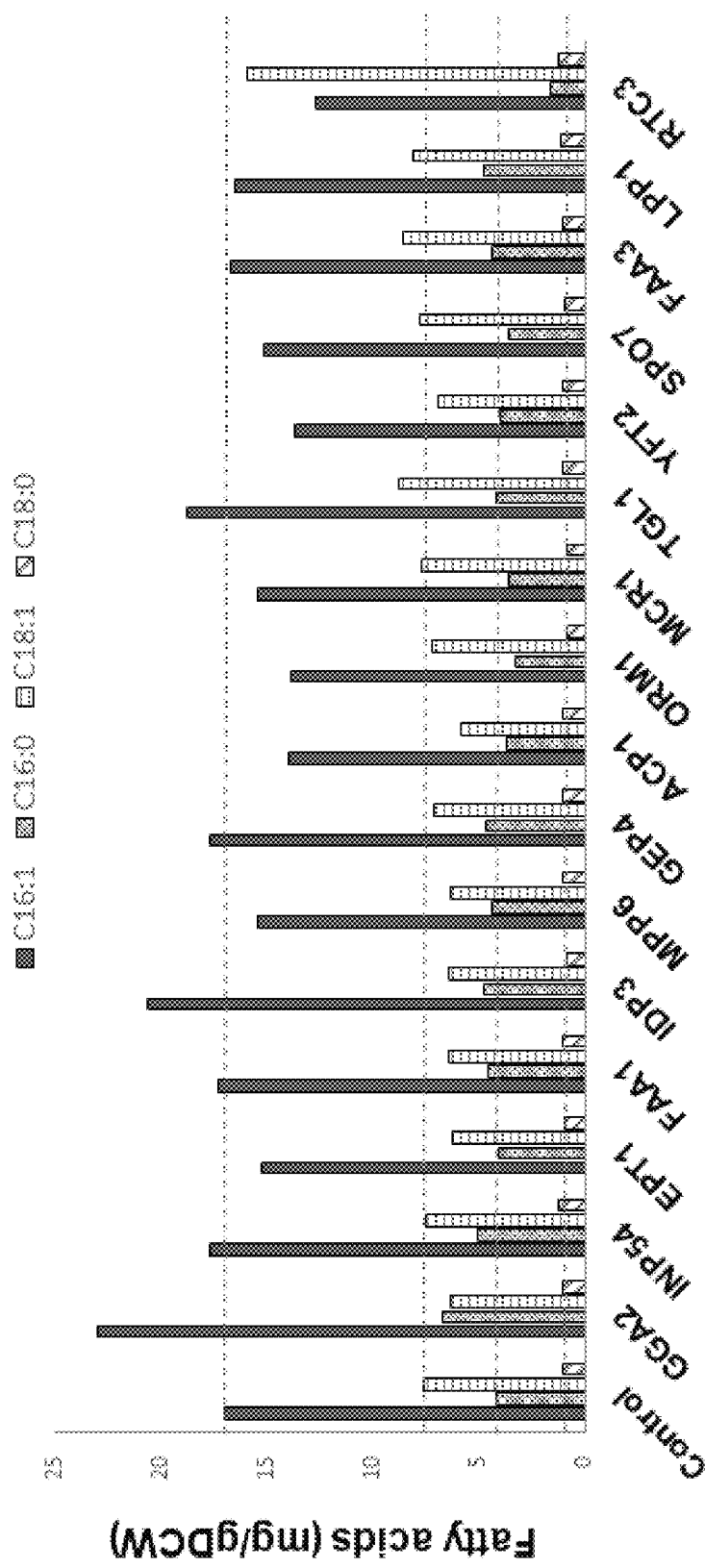
FIG. 13: Effect of individual overexpression of GGA2, INP54, EPT1, FAA1, IDP3, MPP6, GEP4, ACP1, ORM1, MCR1, TGL1, YFT2, SPO7, FAA3, LPP1 and RTC3 on fatty acid composition. IMX581 is the control strain (not overexpressing any of the aforementioned genes). Strains were cultivated at 30° C. and 200 rpm. Samples were taken after 48 hours of cultivation. All numbers are an average of three replicates. C16:0 is palmitic acid, C16:1 is palmitoleic acid, C18:0 is stearic acid, C18:1 is oleic acid. Dashed horizontal lines indicate production of the respective fatty acid by the control strain for easier comparison.

While for some applications production of a mixture of different fatty acids is desirable, in some cases production of specific fatty acids is preferred. Therefore, in addition to measuring total fatty acids, the effects of the overexpression of the aforementioned endogenous genes on production of specific fatty acids, including palmitic acid (C16:0), palmitoleic acid (C16:1), stearic acid (C18:0) and oleic acid (C16:1) were quantified. These results are depicted in FIG. 13. It was found that individual overexpression of GGA2, INP54, FAA1, IDP3, GEP4, FAA3, and LPP1 increased production of palmitic acid (C16:0) by 60.6%, 21.4%, 8%, 13.5%, 10.4%, 3% and 13.3% compared to control, respectively (FIG. 13). It was also found that individual overexpression of GGA2, INP54, IDP3, GEP4 and TGL1 increased production of palmitoleic acid (C16:1) by 35.4%, 4.2%, 21.2%, 3.9% and 10.5% compared to control, respectively (FIG. 13). In addition, individual overexpression of TGL1, SPO7, FAA3, and RTC3 increased production of oleic acid (C18:1) by 14.5%, 2.2%, 12% and 107.8% compared to the control, respectively (FIG. 13). Finally, individual overexpression of GGA2, INP54, FAA1, MPP6, GEP4, TGL1, FAA3, LPP1 and RTC3 increased production of stearic acid (C18:0) by 6.6%, 19.5%, 2.8%, 4.8%, 3%, 2.7%, 4.7%, 14.1% and 24.6% compared to control, respectively. These results indicated that in addition to having beneficial effects on the production of fatty acids in general, several of these genes had beneficial effects on production of specific fatty acids. In particular, production of palmitic acid particularly benefited from overexpression of GGA2 or INP54, production of palmitoleic acid particularly benefited from overexpression of GGA2 or IDP3, production of oleic acid particularly benefited from overexpression of RTC3, and production of stearic acid particularly benefited from overexpression of INP54 or RTC3.

REFERENCES

David and Siewers, Advances in yeast genome engineering, *FEMS yeast research*, 2015, 15(1): 1-14

Deatherage and Barrick, Identification of mutations in laboratory—evolved microbes from next-generation sequencing data using breseq, *Methods Mol. Biol*, 2014, 1151: 165-188

Gietz and Schiestl, High-efficiency yeast transformation using the LiAc/SS carrier DNA/PEG method, *Nature Protocols*, 2007, 2(1): 31-34

Jenjaroenpun et al., Complete genomic and transcriptional landscape analysis using third-generation sequencing: a case study of *Saccharomyces cerevisiae* CEN.PK113-7D, *Nucleic Acids Res*, 2018, 46: e38

Jessop-Fabre, et al., EasyClone-MarkerFree: A vector toolkit for marker-less integration of genes into *Saccharomyces cerevisiae* via CRISPR-Cas9, *Biotechnol J*, 2016, 11(8): 1110-1117

Langmead and Salzberg, Fast gapped-read alignment with Bowtie 2, *Nat. Methods*, 2012, 9: 357-359

Mans et al., CRISPR/Cas9: a molecular Swiss army knife for simultaneous introduction of multiple genetic modifications in *Saccharomyces cerevisiae*, *FEMS Yeast Res*, 2015, 15(2): pii: fov004

Pfleger et al., Metabolic engineering strategies for microbial synthesis of oleochemicals, *Metabolic Engineering*, 2015, 29: 1-11

Zhang et al., Adaptive mutations in sugar metabolism restore growth on glucose in a pyruvate decarboxylase negative yeast strain, *Microbial cell factories*, 2015, 14: 116

Zhou et al., Modular pathway engineering of diterpenoid synthases and the mevalonic acid pathway for miltiradiene production, *J Am Chem Soc*, 2012, 134(6): 3234-3241

Zhou et al., Production of fatty acid-derived oleochemicals and biofuels by synthetic yeast cell factories, *Nature Communications*, 2016, 7: 11709

The invention claimed is:

1. A fungal cell for the production of fatty acids and/or fatty acid-derived products, wherein said fungal cell is genetically modified for overexpression of an endogenous acetyl-CoA carboxylase and an endogenous pyruvate carboxylase, and wherein said fungal cell has an increased production of fatty acids and/or fatty acid-derived products over a wild-type fungal cell that is not genetically modified for overexpression of said endogenous acetyl-CoA carboxylase and said endogenous pyruvate carboxylase.

2. The fungal cell according to claim 1, wherein said endogenous acetyl-CoA carboxylase is ACC1 and said endogenous pyruvate carboxylase is PYC1.

3. The fungal cell according to claim 1, wherein said fungal cell is further genetically modified for overexpression of at least one protein selected from the group consisting of an endogenous mitochondrial pyruvate carrier, a citrate synthase selected from the group consisting of Rhodosporidium toruloides citrate synthase RtCIT1 and Saccharomyces cerevisiae citrate synthase ScCIT1, and an endogenous citrate and oxoglutarate carrier protein.

4. The fungal cell according to claim 3, wherein said endogenous mitochondrial pyruvate carrier is selected from the group consisting of MPC1 and MPC3.

5. The fungal cell according to claim 3, wherein said endogenous citrate and oxoglutarate carrier protein is YHM2.

6. The fungal cell according to claim 1, wherein said fungal cell is further modified for overexpression of at least one protein selected from the group consisting of an endogenous cytosolic isocitrate dehydrogenase and Aspergillus nidulans ATP-citrate lyase AnACL.

7. The fungal cell according to claim 6, wherein said endogenous cytosolic isocitrate dehydrogenase is IDP2.

8. The fungal cell according to claim 1, wherein said fungal cell is further genetically modified for downregulation of at least one endogenous protein selected from the group consisting of an endogenous mitochondrial NAD+-dependent isocitrate dehydrogenase and an endogenous phosphoglucose isomerase.

9. The fungal cell according to claim 8, wherein said endogenous mitochondrial NAD+-dependent isocitrate dehydrogenase is encoded by IDH2.

10. The fungal cell according to claim 8, wherein said endogenous phosphoglucose isomerase is encoded by PGI1.

11. The fungal cell according to claim 8, wherein said fungal cell has a native promoter of said endogenous protein replaced by a weaker promoter.

12. The fungal cell according to claim 11, wherein said weaker promoter is selected from the group consisting of pINH1, pSDH4, pATP5, pGSY2, pGSP2, and pRBK1.

13. The fungal cell according to claim 1, wherein a native promoter of at least one essential gene is replaced by a carbon-source-dependent promoter.

14. The fungal cell according to claim 13, wherein said at least one essential gene is selected from the group consisting of ERG9 and LEU2.

15. The fungal cell according to claim 1, wherein pyruvate decarboxylase activity in said fungal cells is downregulated by the deletion of at least one gene selected from the group consisting of PDC1, PDC5 and PDC6.

16. The fungal cell according to claim 1, wherein said fungal cell is further genetically modified for downregulation of an endogenous fructose-1,6-bisphosphate (FBP)-sensitive pyruvate kinase PYK1.

17. The fungal cell according to claim 1, wherein said fungal cell is further genetically modified for overexpression of an endogenous fructose-1,6-bisphosphate(FBP)-insensitive pyruvate kinase PYK2.

18. The fungal cell according to claim 1, wherein said fungal cell is genetically modified for overexpression of a fatty acid transport protein selected from the group consisting of an endogenous ATP-binding cassette (ABC) protein, an endogenous lipid transfer protein (LTP), an endogenous fatty acid transporter protein (FATP) selected from the group consisting of Homo sapiens FATP1, Homo sapiens FATP4, and Saccharomyces cerevisiae FAT1, and a plant wax ester transporter selected from the group consisting of Arabidopsis ABCG11, ABCG12, LTPG1 and LTPG2.

19. The fungal cell according to claim 1, wherein said fungal cell is genetically modified for overexpression of a gene selected from the group consisting of MPP6, ACP1, EPT1, FAA1, GEP4, GGA2, IDP3, INP54, LPP1, MCR1, ORM1, RTC3, SPO7, TGL1 and YFT2.

20. The fungal cell according to claim 19, wherein said fungal cell is genetically modified for overexpression of GGA2.

21. The fungal cell according to claim 1, wherein said fungal cell is a fungal cell selected from the group consisting of Saccharomyces, Kluyveromyces, Zygosaccharomyces, Candida, Hansenula, Torulopsis, Kloeckera, Pichia, Schizosaccharomyces, Trigonopsis, Brettanomyces, Debaromyces, Nadsonia, Lipomyces, Cryptococcus, Aureobasidium, Trichosporon, Lipomyces, Rhodotorula, Yarrowia, Rhodosporidium, Phaffia, Schwanniomyces, Aspergillus, and Ashbya.

22. The fungal cell according to claim 21, wherein said fungal cell is a fungal cell selected from the group consisting of Saccharomyces cerevisiae, Pichia pastoris, Ashbya gossypii, Saccharomyces boulardii, Zygosaccharomyces bailii, Kluyveromyces lactis, Rhodosporidium toruloides and Yarrowia lipolytica.

23. A method for producing a fatty acid comprising:
culturing a fungal cell according to claim 1 in a culture medium and in culture conditions suitable for production of said fatty acid by said fungal cell, and
collecting said fatty acid from said culture medium and/or said fungal cell.

24. A method for producing a fatty acid derived-product comprising:
culturing a fungal cell according claim 1 in a culture medium and in culture conditions suitable for production of said fatty acid-derived product by said fungal cell; and
collecting said fatty acid-derived product from said culture medium and/or said fungal cell, wherein said fatty acid-derived product is selected from the group consisting of a hydrocarbon, a triacylglyceride, a phospholipid, a lactone, a fatty alcohol, a fatty aldehyde, a fatty acid ester, and a mixture thereof.

* * * * *

SEQUENCE LISTING

```
<160> NUMBER OF SEQ ID NOS: 40

<210> SEQ ID NO 1
<211> LENGTH: 2233
<212> TYPE: PRT
<213> ORGANISM: Saccharomyces cerevisiae

<400> SEQUENCE: 1

Met Ser Glu Glu Ser Leu Phe Glu Ser Ser Pro Gln Lys Met Glu Tyr
1               5                   10                  15

Glu Ile Thr Asn Tyr Ser Glu Arg His Thr Glu Leu Pro Gly His Phe
            20                  25                  30

Ile Gly Leu Asn Thr Val Asp Lys Leu Glu Glu Ser Pro Leu Arg Asp
        35                  40                  45
```

```
Phe Val Lys Ser His Gly Gly His Thr Val Ile Ser Lys Ile Leu Ile
 50                  55                  60

Ala Asn Asn Gly Ile Ala Ala Val Lys Glu Ile Arg Ser Val Arg Lys
 65                  70                  75                  80

Trp Ala Tyr Glu Thr Phe Gly Asp Asp Arg Thr Val Gln Phe Val Ala
                     85                  90                  95

Met Ala Thr Pro Glu Asp Leu Glu Ala Asn Ala Glu Tyr Ile Arg Met
                100                 105                 110

Ala Asp Gln Tyr Ile Glu Val Pro Gly Gly Thr Asn Asn Asn Asn Tyr
                115                 120                 125

Ala Asn Val Asp Leu Ile Val Asp Ile Ala Glu Arg Ala Asp Val Asp
130                 135                 140

Ala Val Trp Ala Gly Trp Gly His Ala Ser Glu Asn Pro Leu Leu Pro
145                 150                 155                 160

Glu Lys Leu Ser Gln Ser Lys Arg Lys Val Ile Phe Ile Gly Pro Pro
                165                 170                 175

Gly Asn Ala Met Arg Ser Leu Gly Asp Lys Ile Ser Ser Thr Ile Val
                180                 185                 190

Ala Gln Ser Ala Lys Val Pro Cys Ile Pro Trp Ser Gly Thr Gly Val
                195                 200                 205

Asp Thr Val His Val Asp Glu Lys Thr Gly Leu Val Ser Val Asp Asp
                210                 215                 220

Asp Ile Tyr Gln Lys Gly Cys Cys Thr Ser Pro Glu Asp Gly Leu Gln
225                 230                 235                 240

Lys Ala Lys Arg Ile Gly Phe Pro Val Met Ile Lys Ala Ser Glu Gly
                245                 250                 255

Gly Gly Gly Lys Gly Ile Arg Gln Val Glu Arg Glu Glu Asp Phe Ile
                260                 265                 270

Ala Leu Tyr His Gln Ala Ala Asn Glu Ile Pro Gly Ser Pro Ile Phe
                275                 280                 285

Ile Met Lys Leu Ala Gly Arg Ala Arg His Leu Glu Val Gln Leu Leu
                290                 295                 300

Ala Asp Gln Tyr Gly Thr Asn Ile Ser Leu Phe Gly Arg Asp Cys Ser
305                 310                 315                 320

Val Gln Arg Arg His Gln Lys Ile Ile Glu Glu Ala Pro Val Thr Ile
                325                 330                 335

Ala Lys Ala Glu Thr Phe His Glu Met Glu Lys Ala Ala Val Arg Leu
                340                 345                 350

Gly Lys Leu Val Gly Tyr Val Ser Ala Gly Thr Val Glu Tyr Leu Tyr
                355                 360                 365

Ser His Asp Asp Gly Lys Phe Tyr Phe Leu Glu Leu Asn Pro Arg Leu
                370                 375                 380

Gln Val Glu His Pro Thr Thr Glu Met Val Ser Gly Val Asn Leu Pro
385                 390                 395                 400

Ala Ala Gln Leu Gln Ile Ala Met Gly Ile Pro Met His Arg Ile Ser
                405                 410                 415

Asp Ile Arg Thr Leu Tyr Gly Met Asn Pro His Ser Ala Ser Glu Ile
                420                 425                 430

Asp Phe Glu Phe Lys Thr Gln Asp Ala Thr Lys Lys Gln Arg Arg Pro
                435                 440                 445

Ile Pro Lys Gly His Cys Thr Ala Cys Arg Ile Thr Ser Glu Asp Pro
450                 455                 460

Asn Asp Gly Phe Lys Pro Ser Gly Gly Thr Leu His Glu Leu Asn Phe
```

```
                465                 470                 475                 480
Arg Ser Ser Ser Asn Val Trp Gly Tyr Phe Ser Val Gly Asn Asn Gly
                    485                 490                 495
Asn Ile His Ser Phe Ser Asp Ser Gln Phe Gly His Ile Phe Ala Phe
                500                 505                 510
Gly Glu Asn Arg Gln Ala Ser Arg Lys His Met Val Ala Leu Lys
            515                 520                 525
Glu Leu Ser Ile Arg Gly Asp Phe Arg Thr Thr Val Glu Tyr Leu Ile
            530                 535                 540
Lys Leu Leu Glu Thr Glu Asp Phe Glu Asp Asn Thr Ile Thr Thr Gly
545                 550                 555                 560
Trp Leu Asp Asp Leu Ile Thr His Lys Met Thr Ala Glu Lys Pro Asp
                565                 570                 575
Pro Thr Leu Ala Val Ile Cys Gly Ala Ala Thr Lys Ala Phe Leu Ala
                580                 585                 590
Ser Glu Glu Ala Arg His Lys Tyr Ile Glu Ser Leu Gln Lys Gly Gln
            595                 600                 605
Val Leu Ser Lys Asp Leu Leu Gln Thr Met Phe Pro Val Asp Phe Ile
    610                 615                 620
His Glu Gly Lys Arg Tyr Lys Phe Thr Val Ala Lys Ser Gly Asn Asp
625                 630                 635                 640
Arg Tyr Thr Leu Phe Ile Asn Gly Ser Lys Cys Asp Ile Ile Leu Arg
                645                 650                 655
Gln Leu Ser Asp Gly Gly Leu Leu Ile Ala Ile Gly Gly Lys Ser His
            660                 665                 670
Thr Ile Tyr Trp Lys Glu Glu Val Ala Ala Thr Arg Leu Ser Val Asp
            675                 680                 685
Ser Met Thr Thr Leu Leu Glu Val Glu Asn Asp Pro Thr Gln Leu Arg
            690                 695                 700
Thr Pro Ser Pro Gly Lys Leu Val Lys Phe Leu Val Glu Asn Gly Glu
705                 710                 715                 720
His Ile Ile Lys Gly Gln Pro Tyr Ala Glu Ile Glu Val Met Lys Met
                725                 730                 735
Gln Met Pro Leu Val Ser Gln Glu Asn Gly Ile Val Gln Leu Leu Lys
                740                 745                 750
Gln Pro Gly Ser Thr Ile Val Ala Gly Asp Ile Met Ala Ile Met Thr
            755                 760                 765
Leu Asp Asp Pro Ser Lys Val Lys His Ala Leu Pro Phe Glu Gly Met
770                 775                 780
Leu Pro Asp Phe Gly Ser Pro Val Ile Glu Gly Thr Lys Pro Ala Tyr
785                 790                 795                 800
Lys Phe Lys Ser Leu Val Ser Thr Leu Glu Asn Ile Leu Lys Gly Tyr
                805                 810                 815
Asp Asn Gln Val Ile Met Asn Ala Ser Leu Gln Gln Leu Ile Glu Val
                820                 825                 830
Leu Arg Asn Pro Lys Leu Pro Tyr Ser Glu Trp Lys Leu His Ile Ser
            835                 840                 845
Ala Leu His Ser Arg Leu Pro Ala Lys Leu Asp Glu Gln Met Glu Glu
            850                 855                 860
Leu Val Ala Arg Ser Leu Arg Arg Gly Ala Val Phe Pro Ala Arg Gln
865                 870                 875                 880
Leu Ser Lys Leu Ile Asp Met Ala Val Lys Asn Pro Glu Tyr Asn Pro
                885                 890                 895
```

-continued

Asp Lys Leu Leu Gly Ala Val Glu Pro Leu Ala Asp Ile Ala His
        900                 905                 910

Lys Tyr Ser Asn Gly Leu Glu Ala His Glu His Ser Ile Phe Val His
        915                 920                 925

Phe Leu Glu Glu Tyr Tyr Glu Val Glu Lys Leu Phe Asn Gly Pro Asn
930                 935                 940

Val Arg Glu Glu Asn Ile Ile Leu Lys Leu Arg Asp Glu Asn Pro Lys
945                 950                 955                 960

Asp Leu Asp Lys Val Ala Leu Thr Val Leu Ser His Ser Lys Val Ser
            965                 970                 975

Ala Lys Asn Asn Leu Ile Leu Ala Ile Leu Lys His Tyr Gln Pro Leu
            980                 985                 990

Cys Lys Leu Ser Ser Lys Val Ser Ala Ile Phe Ser Thr Pro Leu Gln
            995                 1000                1005

His Ile Val Glu Leu Glu Ser Lys Ala Thr Ala Lys Val Ala Leu
        1010                1015                1020

Gln Ala Arg Glu Ile Leu Ile Gln Gly Ala Leu Pro Ser Val Lys
        1025                1030                1035

Glu Arg Thr Glu Gln Ile Glu His Ile Leu Lys Ser Ser Val Val
        1040                1045                1050

Lys Val Ala Tyr Gly Ser Ser Asn Pro Lys Arg Ser Glu Pro Asp
        1055                1060                1065

Leu Asn Ile Leu Lys Asp Leu Ile Asp Ser Asn Tyr Val Val Phe
        1070                1075                1080

Asp Val Leu Leu Gln Phe Leu Thr His Gln Asp Pro Val Val Thr
        1085                1090                1095

Ala Ala Ala Ala Gln Val Tyr Ile Arg Arg Ala Tyr Arg Ala Tyr
        1100                1105                1110

Thr Ile Gly Asp Ile Arg Val His Glu Gly Val Thr Val Pro Ile
        1115                1120                1125

Val Glu Trp Lys Phe Gln Leu Pro Ser Ala Ala Phe Ser Thr Phe
        1130                1135                1140

Pro Thr Val Lys Ser Lys Met Gly Met Asn Arg Ala Val Ser Val
        1145                1150                1155

Ser Asp Leu Ser Tyr Val Ala Asn Ser Gln Ser Ser Pro Leu Arg
        1160                1165                1170

Glu Gly Ile Leu Met Ala Val Asp His Leu Asp Asp Val Asp Glu
        1175                1180                1185

Ile Leu Ser Gln Ser Leu Glu Val Ile Pro Arg His Gln Ser Ser
        1190                1195                1200

Ser Asn Gly Pro Ala Pro Asp Arg Ser Gly Ser Ser Ala Ser Leu
        1205                1210                1215

Ser Asn Val Ala Asn Val Cys Val Ala Ser Thr Glu Gly Phe Glu
        1220                1225                1230

Ser Glu Glu Glu Ile Leu Val Arg Leu Arg Glu Ile Leu Asp Leu
        1235                1240                1245

Asn Lys Gln Glu Leu Ile Asn Ala Ser Ile Arg Arg Ile Thr Phe
        1250                1255                1260

Met Phe Gly Phe Lys Asp Gly Ser Tyr Pro Lys Tyr Tyr Thr Phe
        1265                1270                1275

Asn Gly Pro Asn Tyr Asn Glu Asn Glu Thr Ile Arg His Ile Glu
        1280                1285                1290

```
Pro Ala Leu Ala Phe Gln Leu Glu Leu Gly Arg Leu Ser Asn Phe
    1295                1300                1305

Asn Ile Lys Pro Ile Phe Thr Asp Asn Arg Asn Ile His Val Tyr
    1310                1315                1320

Glu Ala Val Ser Lys Thr Ser Pro Leu Asp Lys Arg Phe Phe Thr
    1325                1330                1335

Arg Gly Ile Ile Arg Thr Gly His Ile Arg Asp Asp Ile Ser Ile
    1340                1345                1350

Gln Glu Tyr Leu Thr Ser Glu Ala Asn Arg Leu Met Ser Asp Ile
    1355                1360                1365

Leu Asp Asn Leu Glu Val Thr Asp Thr Ser Asn Ser Asp Leu Asn
    1370                1375                1380

His Ile Phe Ile Asn Phe Ile Ala Val Phe Asp Ile Ser Pro Glu
    1385                1390                1395

Asp Val Glu Ala Ala Phe Gly Gly Phe Leu Glu Arg Phe Gly Lys
    1400                1405                1410

Arg Leu Leu Arg Leu Arg Val Ser Ser Ala Glu Ile Arg Ile Ile
    1415                1420                1425

Ile Lys Asp Pro Gln Thr Gly Ala Pro Val Pro Leu Arg Ala Leu
    1430                1435                1440

Ile Asn Asn Val Ser Gly Tyr Val Ile Lys Thr Glu Met Tyr Thr
    1445                1450                1455

Glu Val Lys Asn Ala Lys Gly Glu Trp Val Phe Lys Ser Leu Gly
    1460                1465                1470

Lys Pro Gly Ser Met His Leu Arg Pro Ile Ala Thr Pro Tyr Pro
    1475                1480                1485

Val Lys Glu Trp Leu Gln Pro Lys Arg Tyr Lys Ala His Leu Met
    1490                1495                1500

Gly Thr Thr Tyr Val Tyr Asp Phe Pro Glu Leu Phe Arg Gln Ala
    1505                1510                1515

Ser Ser Ser Gln Trp Lys Asn Phe Ser Ala Asp Val Lys Leu Thr
    1520                1525                1530

Asp Asp Phe Phe Ile Ser Asn Glu Leu Ile Glu Asp Glu Asn Gly
    1535                1540                1545

Glu Leu Thr Glu Val Glu Arg Glu Pro Gly Ala Asn Ala Ile Gly
    1550                1555                1560

Met Val Ala Phe Lys Ile Thr Val Lys Thr Pro Glu Tyr Pro Arg
    1565                1570                1575

Gly Arg Gln Phe Val Val Val Ala Asn Asp Ile Thr Phe Lys Ile
    1580                1585                1590

Gly Ser Phe Gly Pro Gln Glu Asp Glu Phe Phe Asn Lys Val Thr
    1595                1600                1605

Glu Tyr Ala Arg Lys Arg Gly Ile Pro Arg Ile Tyr Leu Ala Ala
    1610                1615                1620

Asn Ser Gly Ala Arg Ile Gly Met Ala Glu Glu Ile Val Pro Leu
    1625                1630                1635

Phe Gln Val Ala Trp Asn Asp Ala Ala Asn Pro Asp Lys Gly Phe
    1640                1645                1650

Gln Tyr Leu Tyr Leu Thr Ser Glu Gly Met Glu Thr Leu Lys Lys
    1655                1660                1665

Phe Asp Lys Glu Asn Ser Val Leu Thr Glu Arg Thr Val Ile Asn
    1670                1675                1680

Gly Glu Glu Arg Phe Val Ile Lys Thr Ile Ile Gly Ser Glu Asp
```

-continued

```
            1685                1690                1695
Gly Leu Gly Val Glu Cys Leu Arg Gly Ser Gly Leu Ile Ala Gly
            1700                1705                1710
Ala Thr Ser Arg Ala Tyr His Asp Ile Phe Thr Ile Thr Leu Val
            1715                1720                1725
Thr Cys Arg Ser Val Gly Ile Gly Ala Tyr Leu Val Arg Leu Gly
            1730                1735                1740
Gln Arg Ala Ile Gln Val Glu Gly Gln Pro Ile Ile Leu Thr Gly
            1745                1750                1755
Ala Pro Ala Ile Asn Lys Met Leu Gly Arg Glu Val Tyr Thr Ser
            1760                1765                1770
Asn Leu Gln Leu Gly Gly Thr Gln Ile Met Tyr Asn Asn Gly Val
            1775                1780                1785
Ser His Leu Thr Ala Val Asp Asp Leu Ala Gly Val Glu Lys Ile
            1790                1795                1800
Val Glu Trp Met Ser Tyr Val Pro Ala Lys Arg Asn Met Pro Val
            1805                1810                1815
Pro Ile Leu Glu Thr Lys Asp Thr Trp Asp Arg Pro Val Asp Phe
            1820                1825                1830
Thr Pro Thr Asn Asp Glu Thr Tyr Asp Val Arg Trp Met Ile Glu
            1835                1840                1845
Gly Arg Glu Thr Glu Ser Gly Phe Glu Tyr Gly Leu Phe Asp Lys
            1850                1855                1860
Gly Ser Phe Phe Glu Thr Leu Ser Gly Trp Ala Lys Gly Val Val
            1865                1870                1875
Val Gly Arg Ala Arg Leu Gly Gly Ile Pro Leu Gly Val Ile Gly
            1880                1885                1890
Val Glu Thr Arg Thr Val Glu Asn Leu Ile Pro Ala Asp Pro Ala
            1895                1900                1905
Asn Pro Asn Ser Ala Glu Thr Leu Ile Gln Glu Pro Gly Gln Val
            1910                1915                1920
Trp His Pro Asn Ser Ala Phe Lys Thr Ala Gln Ala Ile Asn Asp
            1925                1930                1935
Phe Asn Asn Gly Glu Gln Leu Pro Met Met Ile Leu Ala Asn Trp
            1940                1945                1950
Arg Gly Phe Ser Gly Gly Gln Arg Asp Met Phe Asn Glu Val Leu
            1955                1960                1965
Lys Tyr Gly Ser Phe Ile Val Asp Ala Leu Val Asp Tyr Lys Gln
            1970                1975                1980
Pro Ile Ile Ile Tyr Ile Pro Pro Thr Gly Glu Leu Arg Gly Gly
            1985                1990                1995
Ser Trp Val Val Val Asp Pro Thr Ile Asn Ala Asp Gln Met Glu
            2000                2005                2010
Met Tyr Ala Asp Val Asn Ala Arg Ala Gly Val Leu Glu Pro Gln
            2015                2020                2025
Gly Met Val Gly Ile Lys Phe Arg Arg Glu Lys Leu Leu Asp Thr
            2030                2035                2040
Met Asn Arg Leu Asp Asp Lys Tyr Arg Glu Leu Arg Ser Gln Leu
            2045                2050                2055
Ser Asn Lys Ser Leu Ala Pro Glu Val His Gln Gln Ile Ser Lys
            2060                2065                2070
Gln Leu Ala Asp Arg Glu Arg Glu Leu Leu Pro Ile Tyr Gly Gln
            2075                2080                2085
```

Ile Ser Leu Gln Phe Ala Asp Leu His Asp Arg Ser Ser Arg Met
    2090                2095                2100

Val Ala Lys Gly Val Ile Ser Lys Glu Leu Glu Trp Thr Glu Ala
    2105                2110                2115

Arg Arg Phe Phe Phe Trp Arg Leu Arg Arg Arg Leu Asn Glu Glu
    2120                2125                2130

Tyr Leu Ile Lys Arg Leu Ser His Gln Val Gly Glu Ala Ser Arg
    2135                2140                2145

Leu Glu Lys Ile Ala Arg Ile Arg Ser Trp Tyr Pro Ala Ser Val
    2150                2155                2160

Asp His Glu Asp Asp Arg Gln Val Ala Thr Trp Ile Glu Glu Asn
    2165                2170                2175

Tyr Lys Thr Leu Asp Asp Lys Leu Lys Gly Leu Lys Leu Glu Ser
    2180                2185                2190

Phe Ala Gln Asp Leu Ala Lys Lys Ile Arg Ser Asp His Asp Asn
    2195                2200                2205

Ala Ile Asp Gly Leu Ser Glu Val Ile Lys Met Leu Ser Thr Asp
    2210                2215                2220

Asp Lys Glu Lys Leu Leu Lys Thr Leu Lys
    2225                2230

<210> SEQ ID NO 2
<211> LENGTH: 1178
<212> TYPE: PRT
<213> ORGANISM: Saccharomyces cerevisiae

<400> SEQUENCE: 2

Met Ser Gln Arg Lys Phe Ala Gly Leu Arg Asp Asn Phe Asn Leu Leu
1               5                   10                  15

Gly Glu Lys Asn Lys Ile Leu Val Ala Asn Arg Gly Glu Ile Pro Ile
                20                  25                  30

Arg Ile Phe Arg Thr Ala His Glu Leu Ser Met Gln Thr Val Ala Ile
            35                  40                  45

Tyr Ser His Glu Asp Arg Leu Ser Thr His Lys Gln Lys Ala Asp Glu
        50                  55                  60

Ala Tyr Val Ile Gly Glu Val Gly Gln Tyr Thr Pro Val Gly Ala Tyr
65                  70                  75                  80

Leu Ala Ile Asp Glu Ile Ile Ser Ile Ala Gln Lys His Gln Val Asp
                85                  90                  95

Phe Ile His Pro Gly Tyr Gly Phe Leu Ser Glu Asn Ser Glu Phe Ala
            100                 105                 110

Asp Lys Val Val Lys Ala Gly Ile Thr Trp Ile Gly Pro Pro Ala Glu
        115                 120                 125

Val Ile Asp Ser Val Gly Asp Lys Val Ser Ala Arg Asn Leu Ala Ala
    130                 135                 140

Lys Ala Asn Val Pro Thr Val Pro Gly Thr Pro Gly Pro Ile Glu Thr
145                 150                 155                 160

Val Glu Glu Ala Leu Asp Phe Val Asn Glu Tyr Gly Tyr Pro Val Ile
                165                 170                 175

Ile Lys Ala Ala Phe Gly Gly Gly Gly Arg Gly Met Arg Val Val Arg
            180                 185                 190

Glu Gly Asp Asp Val Ala Asp Ala Phe Gln Arg Ala Thr Ser Glu Ala
        195                 200                 205

Arg Thr Ala Phe Gly Asn Gly Thr Cys Phe Val Glu Arg Phe Leu Asp

```
           210                 215                 220
Lys Pro Lys His Ile Glu Val Gln Leu Leu Ala Asp Asn His Gly Asn
225                 230                 235                 240

Val Val His Leu Phe Glu Arg Asp Cys Ser Val Gln Arg Arg His Gln
                    245                 250                 255

Lys Val Val Glu Val Ala Pro Ala Lys Thr Leu Pro Arg Glu Val Arg
                260                 265                 270

Asp Ala Ile Leu Thr Asp Ala Val Lys Leu Ala Lys Glu Cys Gly Tyr
            275                 280                 285

Arg Asn Ala Gly Thr Ala Glu Phe Leu Val Asp Asn Gln Asn Arg His
        290                 295                 300

Tyr Phe Ile Glu Ile Asn Pro Arg Ile Gln Val Glu His Thr Ile Thr
305                 310                 315                 320

Glu Glu Ile Thr Gly Ile Asp Ile Val Ala Ala Gln Ile Gln Ile Ala
                    325                 330                 335

Ala Gly Ala Ser Leu Pro Gln Leu Gly Leu Phe Gln Asp Lys Ile Thr
                340                 345                 350

Thr Arg Gly Phe Ala Ile Gln Cys Arg Ile Thr Thr Glu Asp Pro Ala
            355                 360                 365

Lys Asn Phe Gln Pro Asp Thr Gly Arg Ile Glu Val Tyr Arg Ser Ala
        370                 375                 380

Gly Gly Asn Gly Val Arg Leu Asp Gly Gly Asn Ala Tyr Ala Gly Thr
385                 390                 395                 400

Ile Ile Ser Pro His Tyr Asp Ser Met Leu Val Lys Cys Ser Cys Ser
                    405                 410                 415

Gly Ser Thr Tyr Glu Ile Val Arg Arg Lys Met Ile Arg Ala Leu Ile
                420                 425                 430

Glu Phe Arg Ile Arg Gly Val Lys Thr Asn Ile Pro Phe Leu Leu Thr
            435                 440                 445

Leu Leu Thr Asn Pro Val Phe Ile Glu Gly Thr Tyr Trp Thr Thr Phe
        450                 455                 460

Ile Asp Asp Thr Pro Gln Leu Phe Gln Met Val Ser Ser Gln Asn Arg
465                 470                 475                 480

Ala Gln Lys Leu Leu His Tyr Leu Ala Asp Val Ala Val Asn Gly Ser
                    485                 490                 495

Ser Ile Lys Gly Gln Ile Gly Leu Pro Lys Leu Lys Ser Asn Pro Ser
                500                 505                 510

Val Pro His Leu His Asp Ala Gln Gly Asn Val Ile Asn Val Thr Lys
            515                 520                 525

Ser Ala Pro Pro Ser Gly Trp Arg Gln Val Leu Leu Glu Lys Gly Pro
        530                 535                 540

Ala Glu Phe Ala Arg Gln Val Arg Gln Phe Asn Gly Thr Leu Leu Met
545                 550                 555                 560

Asp Thr Thr Trp Arg Asp Ala His Gln Ser Leu Leu Ala Thr Arg Val
                    565                 570                 575

Arg Thr His Asp Leu Ala Thr Ile Ala Pro Thr Thr Ala His Ala Leu
                580                 585                 590

Ala Gly Arg Phe Ala Leu Glu Cys Trp Gly Gly Ala Thr Phe Asp Val
            595                 600                 605

Ala Met Arg Phe Leu His Glu Asp Pro Trp Glu Arg Leu Arg Lys Leu
        610                 615                 620

Arg Ser Leu Val Pro Asn Ile Pro Phe Gln Met Leu Leu Arg Gly Ala
625                 630                 635                 640
```

```
Asn Gly Val Ala Tyr Ser Ser Leu Pro Asp Asn Ala Ile Asp His Phe
                645                 650                 655

Val Lys Gln Ala Lys Asp Asn Gly Val Asp Ile Phe Arg Val Phe Asp
                660                 665                 670

Ala Leu Asn Asp Leu Glu Gln Leu Lys Val Gly Val Asp Ala Val Lys
                675                 680                 685

Lys Ala Gly Gly Val Val Glu Ala Thr Val Cys Phe Ser Gly Asp Met
            690                 695                 700

Leu Gln Pro Gly Lys Lys Tyr Asn Leu Asp Tyr Tyr Leu Glu Ile Ala
705                 710                 715                 720

Glu Lys Ile Val Gln Met Gly Thr His Ile Leu Gly Ile Lys Asp Met
                725                 730                 735

Ala Gly Thr Met Lys Pro Ala Ala Lys Leu Leu Ile Gly Ser Leu
                740                 745                 750

Arg Ala Lys Tyr Pro Asp Leu Pro Ile His Val His Thr His Asp Ser
                755                 760                 765

Ala Gly Thr Ala Val Ala Ser Met Thr Ala Cys Ala Leu Ala Gly Ala
            770                 775                 780

Asp Val Val Asp Val Ala Ile Asn Ser Met Ser Gly Leu Thr Ser Gln
785                 790                 795                 800

Pro Ser Ile Asn Ala Leu Leu Ala Ser Leu Glu Gly Asn Ile Asp Thr
                805                 810                 815

Gly Ile Asn Val Glu His Val Arg Glu Leu Asp Ala Tyr Trp Ala Glu
                820                 825                 830

Met Arg Leu Leu Tyr Ser Cys Phe Glu Ala Asp Leu Lys Gly Pro Asp
                835                 840                 845

Pro Glu Val Tyr Gln His Glu Ile Pro Gly Gly Gln Leu Thr Asn Leu
                850                 855                 860

Leu Phe Gln Ala Gln Gln Leu Gly Leu Gly Glu Gln Trp Ala Glu Thr
865                 870                 875                 880

Lys Arg Ala Tyr Arg Glu Ala Asn Tyr Leu Leu Gly Asp Ile Val Lys
                885                 890                 895

Val Thr Pro Thr Ser Lys Val Val Gly Asp Leu Ala Gln Phe Met Val
                900                 905                 910

Ser Asn Lys Leu Thr Ser Asp Asp Val Arg Arg Leu Ala Asn Ser Leu
                915                 920                 925

Asp Phe Pro Asp Ser Val Met Asp Phe Phe Glu Gly Leu Ile Gly Gln
930                 935                 940

Pro Tyr Gly Gly Phe Pro Glu Pro Phe Arg Ser Asp Val Leu Arg Asn
945                 950                 955                 960

Lys Arg Arg Lys Leu Thr Cys Arg Pro Gly Leu Glu Leu Glu Pro Phe
                965                 970                 975

Asp Leu Glu Lys Ile Arg Glu Asp Leu Gln Asn Arg Phe Gly Asp Val
                980                 985                 990

Asp Glu Cys Asp Val Ala Ser Tyr Asn Met Tyr Pro Arg Val Tyr Glu
                995                 1000                1005

Asp Phe Gln Lys Met Arg Glu Thr Tyr Gly Asp Leu Ser Val Leu
                1010                1015                1020

Pro Thr Arg Ser Phe Leu Ser Pro Leu Glu Thr Asp Glu Glu Ile
                1025                1030                1035

Glu Val Val Ile Glu Gln Gly Lys Thr Leu Ile Ile Lys Leu Gln
                1040                1045                1050
```

| | | | | | | | | | | |
|---|---|---|---|---|---|---|---|---|---|---|
| Ala | Val | Gly | Asp | Leu | Asn | Lys | Lys | Thr | Gly | Glu | Arg | Glu | Val | Tyr |
| | 1055 | | | | 1060 | | | | 1065 | |

Phe Asp Leu Asn Gly Glu Met Arg Lys Ile Arg Val Ala Asp Arg
    1070                1075                1080

Ser Gln Lys Val Glu Thr Val Thr Lys Ser Lys Ala Asp Met His
    1085                1090                1095

Asp Pro Leu His Ile Gly Ala Pro Met Ala Gly Val Ile Val Glu
    1100                1105                1110

Val Lys Val His Lys Gly Ser Leu Ile Lys Lys Gly Gln Pro Val
    1115                1120                1125

Ala Val Leu Ser Ala Met Lys Met Glu Met Ile Ile Ser Ser Pro
    1130                1135                1140

Ser Asp Gly Gln Val Lys Glu Val Phe Val Ser Asp Gly Glu Asn
    1145                1150                1155

Val Asp Ser Ser Asp Leu Leu Val Leu Leu Glu Asp Gln Val Pro
    1160                1165                1170

Val Glu Thr Lys Ala
    1175

<210> SEQ ID NO 3
<211> LENGTH: 1374
<212> TYPE: DNA
<213> ORGANISM: Artificial Sequence
<220> FEATURE:
<223> OTHER INFORMATION: Synthetic Construct

<400> SEQUENCE: 3

```
atgttctctg ctactagaac tgctgctaga acagcagctc aagctgctaa tagaagaaat      60
gtttccacca tcagagaaac cttgaaagaa atcatcccag aaagacaagc cttgttgaag     120
caaatcaaat ctgaacatgg tgctaagacc ttgggtaatg ttactgttga acaagttgtt     180
ggtggtggta gaggtattaa gtttatgttg tgggatccat ccgttttgga tgctgaagaa     240
ggtattagat tttggggtag atctatccct gaatgccaaa gagatttgcc aactgctcca     300
ggtggtcaag aaattttgcc agaagctatg ttttggtact tgttgactgg taagttccaa     360
ccgctgaac aaactaagca attccaagaa gaattggttt ccagatctga attgccagct     420
catgttgaaa aggttttgga ttctttgcca aagaccttgc atccaatgac ccaatttgtt     480
attggtgttg ctgctttgaa ccacgattct caatttgctg caagatacaa agctggtatg     540
aagaaagctg aatattggga accagcattg aagattcttt ggattgtgt tgctaagtcc     600
ttcactattg cagctagaat ctacttgcac tcttacaaag atggtgctgc aaatatggct     660
ccagttgata agacaaaaga tttgtctgct aacttcgcca ctcaaatcgg ttttggtgat     720
tctgaaggtt tcgtcgaatt gatcagatta tacaactcct gcataccga tcatgaaggt     780
ggtaatgttt ctgctcatac cactcatttg gttggttctg cttttgtctga tccattcttg     840
tcttattctg ctgctttagg tggttttggct ggtccattgc atggtttagc taatcaagaa     900
gtcttgagat tcatcttggg tatgcaaaaa gaattgggtg attccccatc tgatgaacaa     960
atcgttcaat atatctggaa aactttgaac tccggtcaag ttattccagg ttatggtcat    1020
gctgttttga gaaaaccaga tcctagattt gctgccttga gagaatttgg taacaaacat    1080
ccagaaaccg ctaacgatcc agttttcaga atggttgatt ccttgtttaa gttgccccca    1140
ggtgttttga cagaacatgg taaaactaag aacccattcc caaatgttga tgctgcttct    1200
ggttctttgt tgtatcatta cggtttgact caattccctt actacactgt tacttcgggt    1260
```

-continued

```
acttctagag ctattggtgc tttgtcacaa tacgtttggg atagagcttt gggtttgcca    1320
attgaaagac caaagtcttt gtccatggaa gccattttga agttggtcaa gtga          1374
```

<210> SEQ ID NO 4
<211> LENGTH: 3651
<212> TYPE: DNA
<213> ORGANISM: Artificial Sequence
<220> FEATURE:
<223> OTHER INFORMATION: Synthetic construct

<400> SEQUENCE: 4

```
atgctttcac tacgtcaatc tataagattt ttcaagccag ccacaagaac tttgtgtagc      60
tctagatatc tgcttatgtc aggcggaggt ggcatgtcgc aaagaaaatt cgccatgtcg     120
caaagaaaat tcgccggctt gagagataac ttcaatctct gggtgaaaaa gaacaaaata     180
ttggtggcta atagaggaga aattccaatc agaatttttc gtaccgctca tgaactgtct     240
atgcagacgg tagctatata ttctcatgaa gatcgtcttt caacgcacaa acaaaaggct     300
gacgaagcat acgtcatagg tgaagtaggc caatataccc ccgtcggcgc ttatttggcc     360
attgacgaaa tcatttccat gcccaaaaa caccaggtag atttcatcca tccaggttat      420
gggttcttgt ctgaaaattc ggaatttgcc gacaaagtag tgaaggccgg tatcacttgg     480
attggccctc cagctgaagt tattgactcc gtgggtgata aggtctcagc tagaaacctg     540
gcagcaaaag ctaatgtgcc caccgttcct ggtacaccag gtcctataga aactgtagag     600
gaagcacttg acttcgtcaa tgaatacggc tacccggtga tcattaaggc cgcctttggt     660
ggtggtggta gaggtatgag agtcgttaga gaaggtgacg acgtggcaga tgcctttcaa     720
cgtgctacct ccgaagcccg tactgccttc ggtaatggta cctgctttgt ggaaagattc     780
ttggacaagc caaagcatat tgaagttcaa ttgttggccg ataaccacgg aaacgtggtt     840
catcttttcg aaagagactg ttccgtgcag agaagacacc aaaaggttgt cgaagtggcc     900
ccagcaaaga ctttaccccg tgaagtccgt gacgccattt tgacagatgc agttaaattg     960
gccaaagagt gtggctacag aaatgcgggt actgctgaat tcttggttga taaccaaaat    1020
agacactatt tcattgaaat taatccaaga atccaagtgg aacataccat cacagaagaa    1080
attaccggta tagatattgt ggcggctcag atccaaattg cggcaggtgc ctctctaccc    1140
cagctgggcc tattccagga caaaattacg actcgtggct ttgccattca gtgccgtatt    1200
accacggaag accctgctaa gaacttccaa ccagataccg gtagaataga agtgtaccgt    1260
tctgcaggtg gtaatggtgt tagactggat ggtggtaacg cctatgcagg aacaataatc    1320
tcacctcatt acgactcaat gctggtcaaa tgctcatgct ccggttccac ctacgaaatc    1380
gttcgtagaa aaatgattcg tgcattaatc gagttcagaa ttagaggtgt caagaccaac    1440
attcccttcc tattgactct tttgaccaat ccagtattta ttgagggtac atactggacg    1500
acttttattg acgacacccc acaactgttc caaatggttt catcacaaaa cagagcccaa    1560
aaacttttac attacctcgc cgacgtggca gtcaatggtt catctatcaa gggtcaaatt    1620
ggcttgccaa aattaaaatc aaatccaagt gtcccccatt gcacgatgc tcagggcaat     1680 gtcatcaacg ttacaaagtc tgcaccacca tccggatgga ggcaagtgct actagaaaag    1740
gggccagctg aatttgccag acaagttaga cagttcaatg gtactttatt gatggacacc    1800
acctggagag acgctcatca atctctactt gcaacaagag tcagaaccca cgatttggct    1860
acaatcgctc caacaaccgc acatgccctt gcaggtcgtt tcgccttaga atgtggggt    1920 ggtgccacat tcgatgttgc aatgagattt ttgcatgagg atccatggga acgtttgaga    1980
```

-continued

```
aaattaagat ctctggtgcc taatattcca ttccaaatgt tattgcgtgg tgccaatggt    2040
gtggcttatt cttcattgcc tgacaatgct attgaccatt tcgtcaagca agccaaggat    2100
aatggtgttg atatatttag agtctttgat gccttaaatg acttggaaca attgaaggtc    2160
ggtgtagatg ctgtgaagaa ggcaggtggt gttgtagaag ccactgtttg tttctctggg    2220
gatatgcttc agccaggcaa gaaatacaat ttggattact acttggaaat tgctgaaaaa    2280
attgtccaaa tgggcactca tatcctgggt atcaaagata tggcaggtac catgaagcca    2340
gcagctgcca aactactgat tggatctttg agggctaagt accctgatct cccaatacat    2400
gttcacactc acgattctgc aggtactgct gttgcatcaa tgactgcgtg tgctctggcg    2460
ggcgccgatg tcgttgatgt tgccatcaac tcaatgtctg gtttaacttc acaaccatca    2520
atcaatgctc tgttggcttc attagaaggt aatattgaca ctggtattaa cgttgagcat    2580
gtccgtgaac tagatgcata ttgggcagag atgagattgt tatactcttg tttcgaggct    2640
gacttgaagg gcccagatcc agaagtttat caacatgaaa tcccaggtgg tcaattgaca    2700
aacttgttgt ttcaagccca acaattgggt cttggagaac aatgggccga acaaaaaga    2760 gcttacagag aagccaatta tttattgggt gatattgtca agttaccccc aacttcgaag    2820
gtcgttggtg atctggcaca atttatggtc tccaataaat taacttccga tgatgtgaga    2880
cgcctggcta attctttgga tttccctgac tctgttatgg atttcttcga aggcttaatc    2940
ggccaaccat atggtgggtt cccagaacca tttagatcag acgttttaag gaacaagaga    3000
agaaagttga cttgtcgtcc aggcctggaa ctagagccat ttgatctcga aaaaattaga    3060
gaagacttgc agaatagatt tggtgatgtt gatgagtgcg acgttgcttc ttataacatg    3120
tacccaagag tttatgaaga cttccaaaag atgagagaaa cgtatggtga tttatctgta    3180
ttgccaacaa gaagcttttt gtctccacta gagactgacg aagaaattga agttgtaatc    3240
gaacaaggta aaacgctaat tatcaagcta caggctgtgg gtgatttgaa caaaaagacc    3300
ggtgaaagag aagtttactt tgatttgaat ggtgaaatga gaaaaattcg tgttgctgac    3360
agatcacaaa aagtggaaac tgttactaaa tccaaagcag acatgcatga tccattacac    3420
attggtgcac caatggcagg tgtcattgtt gaagttaaag ttcataaagg atcactaata    3480
aagaagggcc aacctgtagc cgtattaagc gccatgaaaa tggaaatgat tatatcttct    3540
ccatccgatg acaagttaa agaagtgttt gtctctgatg gtgaaaatgt ggactcttct    3600
gatttattag ttctattaga agaccaagtt cctgttgaaa ctaaggcatg a             3651
```

<210> SEQ ID NO 5
<211> LENGTH: 655
<212> TYPE: PRT
<213> ORGANISM: Aspergillus nidulans

<400> SEQUENCE: 5

```
Met Pro Ala Ala Pro Leu Val Ser Thr Ala Asn Gly Pro Asn Ala Asn
1               5                  10                  15

Asp Asn Ile Thr Arg Phe Glu Pro Pro Ser Arg Val Arg Ser Pro Phe
            20                  25                  30

Ala Asp Ala Leu Phe His Asn Lys Thr Arg Cys Phe Val Tyr Gly Met
        35                  40                  45

Gln Pro Arg Ala Val Gln Gly Met Leu Asp Phe Asp Phe Ile Cys Lys
    50                  55                  60

Arg Ser Thr Pro Ser Val Ala Gly Ile Ile Tyr Thr Phe Gly Gly Gln
65                  70                  75                  80
```

```
Phe Val Ser Lys Met Tyr Trp Gly Thr Ser Glu Thr Leu Pro Val
            85                  90                  95

Tyr Gln Asp Thr Ala Lys Ala Met Ala Lys His Pro Asp Val Asp Thr
            100                 105                 110

Val Val Asn Phe Ala Ser Ser Arg Ser Val Tyr Ser Ser Thr Met Glu
            115                 120                 125

Leu Met Gln Tyr Pro Gln Ile Lys Cys Ile Ala Ile Ile Ala Glu Gly
            130                 135                 140

Val Pro Glu Arg Arg Ala Arg Glu Ile Leu Val Thr Ala Lys Glu Lys
145                 150                 155                 160

Gly Ile Thr Ile Ile Gly Pro Ala Thr Val Gly Gly Ile Lys Pro Gly
                165                 170                 175

Ala Phe Lys Ile Gly Asn Thr Gly Gly Met Met Asp Asn Ile Val Ala
            180                 185                 190

Ser Lys Leu Tyr Arg Lys Gly Ser Val Gly Tyr Val Ser Lys Ser Gly
            195                 200                 205

Gly Met Ser Asn Glu Leu Asn Asn Ile Ile Ser Gln Thr Thr Asp Gly
            210                 215                 220

Val Tyr Glu Gly Val Ala Ile Gly Gly Asp Arg Tyr Pro Gly Thr Thr
225                 230                 235                 240

Phe Ile Asp His Leu Leu Arg Tyr Gln Ala Glu Pro Glu Cys Lys Ile
                245                 250                 255

Leu Val Leu Leu Gly Glu Val Gly Gly Val Glu Glu Tyr Arg Val Ile
                260                 265                 270

Glu Ala Val Lys Asn Gly Val Ile Thr Lys Pro Ile Val Ala Trp Ala
            275                 280                 285

Ile Gly Thr Cys Ala Ser Met Phe Lys Thr Glu Val Gln Phe Gly His
            290                 295                 300

Ala Gly Ala Ser Ala Asn Ser Asp Leu Glu Thr Ala Val Ala Lys Asn
305                 310                 315                 320

Lys Ala Met Arg Glu Ala Gly Ile Tyr Val Pro Asp Thr Phe Glu Asp
            325                 330                 335

Met Pro Ala Val Leu Lys Lys Val Tyr Glu Gln Val Gln Asn Gly
            340                 345                 350

Val Ile Lys Pro Gln Pro Glu Pro Val Pro Pro Lys Ile Pro Ile Asp
            355                 360                 365

Tyr Ser Trp Ala Gln Glu Leu Gly Leu Ile Arg Lys Pro Ala Ala Phe
            370                 375                 380

Ile Ser Thr Ile Ser Asp Arg Gly Gln Glu Leu Leu Tyr Ala Gly
385                 390                 395                 400

Met Pro Ile Ser Asp Val Phe Lys Glu Asp Ile Gly Ile Gly Gly Val
                405                 410                 415

Met Ser Leu Leu Trp Phe Arg Arg Leu Pro Ser Tyr Ala Thr Lys
            420                 425                 430

Phe Leu Glu Met Val Leu Met Leu Thr Ala Asp His Gly Pro Ala Val
            435                 440                 445

Ser Gly Ala Met Asn Thr Ile Ile Thr Thr Arg Ala Gly Lys Asp Leu
450                 455                 460

Ile Ser Ala Leu Val Ser Gly Leu Leu Thr Ile Gly Ser Arg Phe Gly
465                 470                 475                 480

Gly Ala Leu Asp Gly Ala Ala Glu Glu Phe Thr Lys Ala Phe Asp Lys
                485                 490                 495
```

```
Gly Met Ser Pro Arg Asp Phe Val Asp Thr Met Arg Lys Glu Asn Lys
            500                 505                 510
Leu Ile Pro Gly Ile Gly His Arg Ile Lys Ser Arg Asn Asn Pro Asp
        515                 520                 525
Leu Arg Val Glu Leu Val Lys Glu Tyr Val Lys Lys His Phe Pro Ser
    530                 535                 540
Thr Lys Leu Leu Asp Tyr Ala Ile Ala Val Glu Thr Val Thr Thr Ser
545                 550                 555                 560
Lys Lys Asp Asn Leu Ile Leu Asn Val Asp Gly Cys Ile Ala Val Cys
                565                 570                 575
Phe Val Asp Leu Met Arg Asn Cys Gly Ala Phe Ser Ala Glu Glu Ser
            580                 585                 590
Glu Asp Tyr Met Lys Met Gly Val Leu Asn Gly Leu Phe Val Leu Gly
        595                 600                 605
Arg Ser Ile Gly Leu Ile Ala His Tyr Leu Asp Gln Lys Arg Leu Arg
    610                 615                 620
Thr Gly Leu Tyr Arg His Pro Trp Asp Asp Ile Thr Tyr Leu Leu Pro
625                 630                 635                 640
Ala Leu Gln Lys Gly Gly Ser Glu Gly Arg Val Glu Val Asn Val
                645                 650                 655

<210> SEQ ID NO 6
<211> LENGTH: 1287
<212> TYPE: DNA
<213> ORGANISM: Saccharomyces cerevisiae

<400> SEQUENCE: 6
atgagtatgt tatctagaag attattttcc acctctcgcc ttgctgcttt cagtaagatt      60
aaggtcaaac aacccgttgt cgagttggac ggtgatgaaa tgacccgtat catttgggat     120
aagatcaaga agaaattgat tctaccctac ttggacgtag atttgaagta ctacgactta     180
tctgtcgaat ctcgtgacgc cacctccgac aagattactc aggatgctgc tgaggcgatc     240
aagaagtatg gtgttggtat caaatgtgcc accatcactc tgatgaagc tcgtgtgaag      300 gaattcaacc tgcacaagat gtggaaatct cctaatggta ccatcagaaa cattctcggc     360
ggtacagtgt tcagagagcc cattgtgatt cctagaattc ctagactggt cccacgttgg     420
gaaaaaccaa tcattattgg aagacacgcc acggtgatc aatataaagc tacgacaca      480 ctgatcccag gcccaggatc tttggaactg gtctacaagc catccgaccc tacgactgct     540
caaccacaaa ctttgaaagt gtatgactac aagggcagtg gtgtggccat ggccatgtac     600
aatactgacg aatccatcga agggtttgct cattcgtctt tcaagctggc cattgacaaa     660
aagctaaatc ttttcttgtc aaccaagaac actattttga gaaaatatga cggtcggttc     720
aaagacattt tccaagaagt ttatgaagct caatataaat ccaaattcga caactaggg     780 atccactatg aacaccgttt aattgatgat atggtcgctc aaatgataaa atctaaaggt     840
ggctttatca tggcgctaaa gaactatgac ggtgatgtcc aatctgacat cgtcgctcaa     900
ggatttggct ccttaggttt gatgacttct atcttagtta caccagacgg taaaactttc     960
gaaagtgaag ctgctcatgg taccgtgaca agacattata gaaagtacca aaagggtgaa    1020
gaaacttcta caaactccat tgcatccatt ttcgcgtggt cgagaggtct attgaagaga    1080
ggtgaattgg acaatactcc tgctttgtgt aaatttgcca atattttgga atccgccact    1140
ttgaacacag ttcagcaaga cggtatcatg acgaaggact tggctttggc ttgcggtaac    1200
aacgaaagat ctgcttatgt taccacagaa gaatttttgg atgccgttga aaaaagacta    1260
```
caaaaagaaa tcaagtcgat cgagtaa                                    1287

<210> SEQ ID NO 7
<211> LENGTH: 563
<212> TYPE: PRT
<213> ORGANISM: Saccharomyces cerevisiae

<400> SEQUENCE: 7

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

```
Trp Met Trp Asn Gln Leu Gly Asn Phe Leu Gln Gly Asp Val Val
            370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
                435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
                500                 505                 510

Ala Thr Thr Gly Glu Trp Asp Lys Leu Thr Gln Asp Lys Ser Phe Asn
                515                 520                 525

Asp Asn Ser Lys Ile Arg Met Ile Glu Ile Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln

<210> SEQ ID NO 8
<211> LENGTH: 563
<212> TYPE: PRT
<213> ORGANISM: Saccharomyces cerevisiae

<400> SEQUENCE: 8

Met Ser Glu Ile Thr Leu Gly Lys Tyr Leu Phe Glu Arg Leu Ser Gln
1               5                   10                  15

Val Asn Cys Asn Thr Val Phe Gly Leu Pro Gly Asp Phe Asn Leu Ser
                20                  25                  30

Leu Leu Asp Lys Leu Tyr Glu Val Lys Gly Met Arg Trp Ala Gly Asn
                35                  40                  45

Ala Asn Glu Leu Asn Ala Ala Tyr Ala Ala Asp Gly Tyr Ala Arg Ile
            50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
                100                 105                 110

Leu His His Thr Leu Gly Asn Gly Asp Phe Thr Val Phe His Arg Met
            115                 120                 125

Ser Ala Asn Ile Ser Glu Thr Thr Ala Met Ile Thr Asp Ile Ala Asn
            130                 135                 140

Ala Pro Ala Glu Ile Asp Arg Cys Ile Arg Thr Thr Tyr Thr Thr Gln
145                 150                 155                 160

Arg Pro Val Tyr Leu Gly Leu Pro Ala Asn Leu Val Asp Leu Asn Val
                165                 170                 175
```

Pro Ala Lys Leu Leu Glu Thr Pro Ile Asp Leu Ser Leu Lys Pro Asn
            180                 185                 190

Asp Ala Glu Ala Glu Ala Val Val Arg Thr Val Val Glu Leu Ile
            195                 200                 205

Lys Asp Ala Lys Asn Pro Val Ile Leu Ala Asp Ala Cys Ala Ser Arg
210                 215                 220

His Asp Val Lys Ala Glu Thr Lys Lys Leu Met Asp Leu Thr Gln Phe
225                 230                 235                 240

Pro Val Tyr Val Thr Pro Met Gly Lys Gly Ala Ile Asp Glu Gln His
            245                 250                 255

Pro Arg Tyr Gly Gly Val Tyr Val Gly Thr Leu Ser Arg Pro Glu Val
            260                 265                 270

Lys Lys Ala Val Glu Ser Ala Asp Leu Ile Leu Ser Ile Gly Ala Leu
            275                 280                 285

Leu Ser Asp Phe Asn Thr Gly Ser Phe Ser Tyr Ser Tyr Lys Thr Lys
            290                 295                 300

Asn Ile Val Glu Phe His Ser Asp His Ile Lys Ile Arg Asn Ala Thr
305                 310                 315                 320

Phe Pro Gly Val Gln Met Lys Phe Ala Leu Gln Lys Leu Leu Asp Ala
            325                 330                 335

Ile Pro Glu Val Val Lys Asp Tyr Lys Pro Val Ala Val Pro Ala Arg
            340                 345                 350

Val Pro Ile Thr Lys Ser Thr Pro Ala Asn Thr Pro Met Lys Gln Glu
            355                 360                 365

Trp Met Trp Asn His Leu Gly Asn Phe Leu Arg Glu Gly Asp Ile Val
            370                 375                 380

Ile Ala Glu Thr Gly Thr Ser Ala Phe Gly Ile Asn Gln Thr Thr Phe
385                 390                 395                 400

Pro Thr Asp Val Tyr Ala Ile Val Gln Val Leu Trp Gly Ser Ile Gly
            405                 410                 415

Phe Thr Val Gly Ala Leu Leu Gly Ala Thr Met Ala Ala Glu Glu Leu
            420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
            450                 455                 460

Tyr Ile Phe Val Leu Asn Asn Asn Gly Tyr Thr Ile Glu Lys Leu Ile
465                 470                 475                 480

His Gly Pro His Ala Glu Tyr Asn Glu Ile Gln Gly Trp Asp His Leu
            485                 490                 495

Ala Leu Leu Pro Thr Phe Gly Ala Arg Asn Tyr Glu Thr His Arg Val
            500                 505                 510

Ala Thr Thr Gly Glu Trp Glu Lys Leu Thr Gln Asp Lys Asp Phe Gln
            515                 520                 525

Asp Asn Ser Lys Ile Arg Met Ile Glu Val Met Leu Pro Val Phe Asp
            530                 535                 540

Ala Pro Gln Asn Leu Val Lys Gln Ala Gln Leu Thr Ala Ala Thr Asn
545                 550                 555                 560

Ala Lys Gln

<210> SEQ ID NO 9
<211> LENGTH: 563
<212> TYPE: PRT

<213> ORGANISM: Saccharomyces cerevisiae

<400> SEQUENCE: 9

Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
    130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Glu Gly Asp Val Ile
    370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
            405                 410                 415

Phe Thr Thr Gly Ala Thr Leu Gly Ala Ala Phe Ala Ala Glu Glu Ile
        420                 425                 430

Asp Pro Asn Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
        515                 520                 525

Lys Asn Ser Val Ile Arg Leu Ile Glu Leu Lys Leu Pro Val Phe Asp
    530                 535                 540

Ala Pro Glu Ser Leu Ile Lys Gln Ala Gln Leu Thr Ala Ala Thr Asn
545                 550                 555                 560

Ala Lys Gln

<210> SEQ ID NO 10
<211> LENGTH: 1077
<212> TYPE: DNA
<213> ORGANISM: Saccharomyces cerevisiae

<400> SEQUENCE: 10

```
atgtttgttt caccaccacc agcaacttcg aaaaaccaag ttttacaacg acgtccatta      60
gaatcgacta acagtaatca tgggtttgca agctccctac aggccattcc ggaaaacacg     120
atgagtggca gtgataatgc ttcttttcaa agtttgccac tatcaatgtt ttctgccccc     180
tctactgtgc acacgcaact aactaatgac tcttcgttct ccgaatttcc taaccacaag     240
ttaatcacga gagtgagcct ggatgaagca ttacccaaaa cgttttatga catgtattcg     300
ccagatattc tattagcaga cccatccaac attctctgta acgggcgtcc caagtttacc     360
aagagagagt tattggattg ggatttaaac gatataagat cgttattgat agtcgagaag     420
ttaaggcccg aatggggtaa tcaactaccg gaagtaataa cggtgggtga taatatgccc     480
cagtttaggt tacaattatt accactatat tctagcgatg agaccataat cgcaacgtta     540
gtccattcgg atctgtacat ggaggctaac ttagattatg aattcaaact aaccagcgcc     600
aaatatacag tagcgaccgc tagaaaaaga catgagcata taactggtag aaatgaagcc     660
gtcatgaatt tgtcgaaacc ggaatggaga aatatcatcg aaaattacct cttaaatata     720
gcagtagagg cacaatgcag gtttgatttc aaacaaagat gctccgaata taagaaatgg     780
aagttacaac agtccaactt aaaaagaccg gacatgcccc accaagcat aataccgcgg     840
aaaaacagca cagaaacaaa atcgcttctg aaaaaggctt tattgaagaa cattcagttg     900
aaaaacccca ataataacct tgatgaattg atgatgagat caagcgccgc aacaaatcaa     960
cagggaaaaa acaaagtcag cttatctaaa gaagaaaagg ctacgatatg gtcgcaatgt    1020
caggcacaag tttaccaaag attaggattg gattggcagc cggattcagt atcctga      1077
```

<210> SEQ ID NO 11
<211> LENGTH: 500

<212> TYPE: PRT
<213> ORGANISM: Saccharomyces cerevisiae

<400> SEQUENCE: 11

```
Met Ser Arg Leu Glu Arg Leu Thr Ser Leu Asn Val Val Ala Gly Ser
1               5                   10                  15

Asp Leu Arg Arg Thr Ser Ile Ile Gly Thr Ile Gly Pro Lys Thr Asn
            20                  25                  30

Asn Pro Glu Thr Leu Val Ala Leu Arg Lys Ala Gly Leu Asn Ile Val
        35                  40                  45

Arg Met Asn Phe Ser His Gly Ser Tyr Glu Tyr His Lys Ser Val Ile
    50                  55                  60

Asp Asn Ala Arg Lys Ser Glu Glu Leu Tyr Pro Gly Arg Pro Leu Ala
65                  70                  75                  80

Ile Ala Leu Asp Thr Lys Gly Pro Glu Ile Arg Thr Gly Thr Thr Thr
                85                  90                  95

Asn Asp Val Asp Tyr Pro Ile Pro Pro Asn His Glu Met Ile Phe Thr
            100                 105                 110

Thr Asp Asp Lys Tyr Ala Lys Ala Cys Asp Asp Lys Ile Met Tyr Val
        115                 120                 125

Asp Tyr Lys Asn Ile Thr Lys Val Ile Ser Ala Gly Arg Ile Ile Tyr
130                 135                 140

Val Asp Asp Gly Val Leu Ser Phe Gln Val Leu Glu Val Val Asp Asp
145                 150                 155                 160

Lys Thr Leu Lys Val Lys Ala Leu Asn Ala Gly Lys Ile Cys Ser His
                165                 170                 175

Lys Gly Val Asn Leu Pro Gly Thr Asp Val Asp Leu Pro Ala Leu Ser
            180                 185                 190

Glu Lys Asp Lys Glu Asp Leu Arg Phe Gly Val Lys Asn Gly Val His
        195                 200                 205

Met Val Phe Ala Ser Phe Ile Arg Thr Ala Asn Asp Val Leu Thr Ile
    210                 215                 220

Arg Glu Val Leu Gly Glu Gln Gly Lys Asp Val Lys Ile Ile Val Lys
225                 230                 235                 240

Ile Glu Asn Gln Gln Gly Val Asn Asn Phe Asp Glu Ile Leu Lys Val
                245                 250                 255

Thr Asp Gly Val Met Val Ala Arg Gly Asp Leu Gly Ile Glu Ile Pro
            260                 265                 270

Ala Pro Glu Val Leu Ala Val Gln Lys Lys Leu Ile Ala Lys Ser Asn
        275                 280                 285

Leu Ala Gly Lys Pro Val Ile Cys Ala Thr Gln Met Leu Glu Ser Met
    290                 295                 300

Thr Tyr Asn Pro Arg Pro Thr Arg Ala Glu Val Ser Asp Val Gly Asn
305                 310                 315                 320

Ala Ile Leu Asp Gly Ala Asp Cys Val Met Leu Ser Gly Glu Thr Ala
                325                 330                 335

Lys Gly Asn Tyr Pro Ile Asn Ala Val Thr Thr Met Ala Glu Thr Ala
            340                 345                 350

Val Ile Ala Glu Gln Ala Ile Ala Tyr Leu Pro Asn Tyr Asp Asp Met
        355                 360                 365

Arg Asn Cys Thr Pro Lys Pro Thr Ser Thr Thr Glu Thr Val Ala Ala
    370                 375                 380

Ser Ala Val Ala Ala Val Phe Glu Gln Lys Ala Lys Ala Ile Ile Val
385                 390                 395                 400
```

```
Leu Ser Thr Ser Gly Thr Thr Pro Arg Leu Val Ser Lys Tyr Arg Pro
                405                 410                 415

Asn Cys Pro Ile Ile Leu Val Thr Arg Cys Pro Arg Ala Ala Arg Phe
            420                 425                 430

Ser His Leu Tyr Arg Gly Val Phe Pro Phe Val Phe Glu Lys Glu Pro
        435                 440                 445

Val Ser Asp Trp Thr Asp Val Glu Ala Arg Ile Asn Phe Gly Ile
    450                 455                 460

Glu Lys Ala Lys Glu Phe Gly Ile Leu Lys Lys Gly Asp Thr Tyr Val
465                 470                 475                 480

Ser Ile Gln Gly Phe Lys Ala Gly Ala Gly His Ser Asn Thr Leu Gln
                485                 490                 495

Val Ser Thr Val
            500

<210> SEQ ID NO 12
<211> LENGTH: 506
<212> TYPE: PRT
<213> ORGANISM: Saccharomyces cerevisiae

<400> SEQUENCE: 12

Met Pro Glu Ser Arg Leu Gln Arg Leu Ala Asn Leu Lys Ile Gly Thr
1               5                   10                  15

Pro Gln Gln Leu Arg Arg Thr Ser Ile Ile Gly Thr Ile Gly Pro Lys
            20                  25                  30

Thr Asn Ser Cys Glu Ala Ile Thr Ala Leu Arg Lys Ala Gly Leu Asn
        35                  40                  45

Ile Ile Arg Leu Asn Phe Ser His Gly Ser Tyr Glu Phe His Gln Ser
    50                  55                  60

Val Ile Glu Asn Ala Val Lys Ser Glu Gln Gln Phe Pro Gly Arg Pro
65                  70                  75                  80

Leu Ala Ile Ala Leu Asp Thr Lys Gly Pro Glu Ile Arg Thr Gly Arg
                85                  90                  95

Thr Leu Asn Asp Gln Asp Leu Tyr Ile Pro Val Asp His Gln Met Ile
            100                 105                 110

Phe Thr Thr Asp Ala Ser Phe Ala Asn Thr Ser Asn Asp Lys Ile Met
        115                 120                 125

Tyr Ile Asp Tyr Ala Asn Leu Thr Lys Val Ile Val Pro Gly Arg Phe
    130                 135                 140

Ile Tyr Val Asp Asp Gly Ile Leu Ser Phe Lys Val Leu Gln Ile Ile
145                 150                 155                 160

Asp Glu Ser Asn Leu Arg Val Gln Ala Val Asn Ser Gly Tyr Ile Ala
                165                 170                 175

Ser His Lys Gly Val Asn Leu Pro Asn Thr Asp Val Asp Leu Pro Pro
            180                 185                 190

Leu Ser Ala Lys Asp Met Lys Asp Leu Gln Phe Gly Val Arg Asn Gly
        195                 200                 205

Ile His Ile Val Phe Ala Ser Phe Ile Arg Thr Ser Glu Asp Val Leu
    210                 215                 220

Ser Ile Arg Lys Ala Leu Gly Ser Glu Gly Gln Asp Ile Lys Ile Ile
225                 230                 235                 240

Ser Lys Ile Glu Asn Gln Gln Gly Leu Asp Asn Phe Asp Glu Ile Leu
                245                 250                 255

Glu Val Thr Asp Gly Val Met Ile Ala Arg Gly Asp Leu Gly Ile Glu
```

```
            260                 265                 270
Ile Leu Ala Pro Glu Val Leu Ala Ile Gln Lys Lys Leu Ile Ala Lys
            275                 280                 285

Cys Asn Leu Ala Gly Lys Pro Val Ile Cys Ala Thr Gln Met Leu Asp
        290                 295                 300

Ser Met Thr His Asn Pro Arg Pro Thr Arg Ala Glu Val Ser Asp Val
305                 310                 315                 320

Gly Asn Ala Val Leu Asp Gly Ala Asp Cys Val Met Leu Ser Gly Glu
                325                 330                 335

Thr Ala Lys Gly Asp Tyr Pro Val Asn Ala Val Asn Ile Met Ala Ala
                340                 345                 350

Thr Ala Leu Ile Ala Glu Ser Thr Ile Ala His Leu Ala Leu Tyr Asp
            355                 360                 365

Asp Leu Arg Asp Ala Thr Pro Lys Pro Thr Ser Thr Glu Thr Val
            370                 375                 380

Ala Ala Ala Ala Thr Ala Ala Ile Leu Glu Gln Asp Gly Lys Ala Ile
385                 390                 395                 400

Val Val Leu Ser Thr Thr Gly Asn Thr Ala Arg Leu Leu Ser Lys Tyr
                405                 410                 415

Arg Pro Ser Cys Pro Ile Ile Leu Val Thr Arg His Ala Arg Thr Ala
                420                 425                 430

Arg Ile Ala His Leu Tyr Arg Gly Val Phe Pro Phe Leu Tyr Glu Pro
            435                 440                 445

Lys Arg Leu Asp Asp Trp Gly Glu Asp Val His Arg Arg Leu Lys Phe
            450                 455                 460

Gly Val Glu Met Ala Arg Ser Phe Gly Met Val Asp Asn Gly Asp Thr
465                 470                 475                 480

Val Val Ser Ile Gln Gly Phe Lys Gly Val Gly His Ser Asn Thr
                485                 490                 495

Leu Arg Ile Ser Thr Val Gly Gln Glu Phe
                500                 505

<210> SEQ ID NO 13
<211> LENGTH: 585
<212> TYPE: PRT
<213> ORGANISM: Saccharomyces cerevisiae

<400> SEQUENCE: 13

Met Ser His Pro His Ser His Ser Ile Tyr Leu Ser Glu Leu Pro Val
1               5                   10                  15

Arg Lys Pro Gln Ala Leu Gly Asn Pro Leu Leu Arg Lys Ile Gln Arg
            20                  25                  30

Ala Cys Arg Met Ser Leu Ala Glu Pro Asp Leu Ala Leu Asn Leu Asp
        35                  40                  45

Ile Ala Asp Tyr Ile Asn Glu Lys Gln Gly Ala Ala Pro Arg Asp Ala
    50                  55                  60

Ala Ile Ala Leu Ala Lys Leu Ile Asn Asn Arg Glu Ser His Val Ala
65                  70                  75                  80

Ile Phe Ala Leu Ser Leu Leu Asp Val Leu Val Lys Asn Cys Gly Tyr
                85                  90                  95

Pro Phe His Leu Gln Ile Ser Arg Lys Glu Phe Leu Asn Glu Leu Val
            100                 105                 110

Lys Arg Phe Pro Gly His Pro Pro Leu Arg Tyr Ser Lys Ile Gln Arg
        115                 120                 125
```

```
Leu Ile Leu Thr Ala Ile Glu Glu Trp Tyr Gln Thr Ile Cys Lys His
        130                 135                 140

Ser Ser Tyr Lys Asn Asp Met Gly Tyr Ile Arg Asp Met His Arg Leu
145                 150                 155                 160

Leu Lys Tyr Lys Gly Tyr Ala Phe Pro Lys Ile Ser Glu Ser Asp Leu
                165                 170                 175

Ala Val Leu Lys Pro Ser Asn Gln Leu Lys Thr Ala Ser Glu Ile Gln
                180                 185                 190

Lys Glu Gln Glu Ile Ala Gln Ala Lys Leu Glu Leu Ile Arg
            195                 200                 205

Arg Gly Lys Pro Glu Asp Leu Arg Glu Ala Asn Lys Leu Met Lys Ile
210                 215                 220

Met Ala Gly Phe Lys Glu Asp Asn Ala Val Gln Ala Lys Gln Ala Ile
225                 230                 235                 240

Ser Ser Glu Leu Asn Lys Leu Lys Arg Lys Ala Asp Leu Leu Asn Glu
                245                 250                 255

Met Leu Glu Ser Pro Asp Ser Gln Asn Trp Asp Asn Glu Thr Thr Gln
                260                 265                 270

Glu Leu His Ser Ala Leu Lys Val Ala Gln Pro Lys Phe Gln Lys Ile
            275                 280                 285

Ile Glu Glu Glu Gln Glu Asp Asp Ala Leu Val Gln Asp Leu Leu Lys
290                 295                 300

Phe Asn Asp Thr Val Asn Gln Leu Leu Glu Lys Phe Asn Leu Leu Lys
305                 310                 315                 320

Asn Gly Asp Ser Asn Ala Ala Ser Gln Ile His Pro Ser His Val Ser
                325                 330                 335

Ala Pro Leu Gln Gln Ser Ser Gly Ala Leu Thr Asn Glu Ile Asn Leu
                340                 345                 350

Ile Asp Phe Asn Asp Leu Asp Glu Ala Pro Ser Gln Gly Asn Asn Asn
            355                 360                 365

Thr Asn Gly Thr Gly Thr Pro Ala Ala Ala Glu Thr Ser Val Asn Asp
        370                 375                 380

Leu Leu Gly Asp Leu Thr Asp Leu Ser Ile Ser Asn Pro Ser Thr Ala
385                 390                 395                 400

Asn Gln Ala Ser Phe Gly Leu Gly Gly Asp Ile Val Leu Gly Ser Ser
                405                 410                 415

Gln Pro Ala Pro Pro Val Thr Thr Asn Ser Asn Asn Thr Leu
            420                 425                 430

Asp Leu Leu Gly Leu Ser Thr Pro Gln Ser Pro Thr Asn Ser Gln Ala
            435                 440                 445

Val Asn Ser Ser Gly Phe Asp Leu Leu Met Gly Phe Asn Pro Thr Thr
450                 455                 460

Gly Thr Thr Thr Ala Pro Ala Arg Thr Leu Val Asn Gln Ser Pro Asn
465                 470                 475                 480

Leu Lys Ile Glu Phe Glu Ile Ser Arg Glu Ser Asn Ser Val Ile Arg
                485                 490                 495

Ile Lys Ser Phe Phe Thr Asn Leu Ser Ser Ser Pro Ile Ser Asn Leu
            500                 505                 510

Val Phe Leu Leu Ala Val Pro Lys Ser Met Ser Leu Lys Leu Gln Pro
            515                 520                 525

Gln Ser Ser Asn Phe Met Ile Gly Asn Ala Lys Asp Gly Ile Ser Gln
530                 535                 540

Glu Gly Thr Ile Glu Asn Ala Pro Ala Asn Pro Ser Lys Ala Leu Lys
```

```
            545                 550                 555                 560
Val Lys Trp Lys Val Asn Tyr Ser Val Asn Ser Thr Gln Ala Glu Glu
                565                 570                 575

Thr Ala Val Phe Thr Leu Pro Asn Val
            580                 585

<210> SEQ ID NO 14
<211> LENGTH: 369
<212> TYPE: PRT
<213> ORGANISM: Saccharomyces cerevisiae

<400> SEQUENCE: 14

Met Leu Arg Asn Thr Phe Phe Arg Asn Thr Ser Arg Arg Phe Leu Ala
1               5                   10                  15

Thr Val Lys Gln Pro Ser Ile Gly Arg Tyr Thr Gly Lys Pro Asn Pro
            20                  25                  30

Ser Thr Gly Lys Tyr Thr Val Ser Phe Ile Glu Gly Asp Gly Ile Gly
        35                  40                  45

Pro Glu Ile Ser Lys Ser Val Lys Lys Ile Phe Ser Ala Ala Asn Val
50                  55                  60

Pro Ile Glu Trp Glu Ser Cys Asp Val Ser Pro Ile Phe Val Asn Gly
65                  70                  75                  80

Leu Thr Thr Ile Pro Asp Pro Ala Val Gln Ser Ile Thr Lys Asn Leu
                85                  90                  95

Val Ala Leu Lys Gly Pro Leu Ala Thr Pro Ile Gly Lys Gly His Arg
            100                 105                 110

Ser Leu Asn Leu Thr Leu Arg Lys Thr Phe Gly Leu Phe Ala Asn Val
        115                 120                 125

Arg Pro Ala Lys Ser Ile Glu Gly Phe Lys Thr Thr Tyr Glu Asn Val
130                 135                 140

Asp Leu Val Leu Ile Arg Glu Asn Thr Glu Gly Glu Tyr Ser Gly Ile
145                 150                 155                 160

Glu His Ile Val Cys Pro Gly Val Val Gln Ser Ile Lys Leu Ile Thr
                165                 170                 175

Arg Asp Ala Ser Glu Arg Val Ile Arg Tyr Ala Phe Glu Tyr Ala Arg
            180                 185                 190

Ala Ile Gly Arg Pro Arg Val Ile Val Val His Lys Ser Thr Ile Gln
        195                 200                 205

Arg Leu Ala Asp Gly Leu Phe Val Asn Val Ala Lys Glu Leu Ser Lys
210                 215                 220

Glu Tyr Pro Asp Leu Thr Leu Glu Thr Glu Leu Ile Asp Asn Ser Val
225                 230                 235                 240

Leu Lys Val Val Thr Asn Pro Ser Ala Tyr Thr Asp Ala Val Ser Val
                245                 250                 255

Cys Pro Asn Leu Tyr Gly Asp Ile Leu Ser Asp Leu Asn Ser Gly Leu
            260                 265                 270

Ser Ala Gly Ser Leu Gly Leu Thr Pro Ser Ala Asn Ile Gly His Lys
        275                 280                 285

Ile Ser Ile Phe Glu Ala Val His Gly Ser Ala Pro Asp Ile Ala Gly
290                 295                 300

Gln Asp Lys Ala Asn Pro Thr Ala Leu Leu Leu Ser Ser Val Met Met
305                 310                 315                 320

Leu Asn His Met Gly Leu Thr Asn His Ala Asp Gln Ile Gln Asn Ala
                325                 330                 335
```

Val Leu Ser Thr Ile Ala Ser Gly Pro Glu Asn Arg Thr Gly Asp Leu
             340                 345                 350

Ala Gly Thr Ala Thr Thr Ser Ser Phe Thr Glu Ala Val Ile Lys Arg
         355                 360                 365

Leu

<210> SEQ ID NO 15
<211> LENGTH: 904
<212> TYPE: DNA
<213> ORGANISM: Saccharomyces cerevisiae

<400> SEQUENCE: 15

| | | | | | |
|---|---|---|---|---|---|
| aacctagatt | gctatctcca | ctccctatgc | ttgctttggt | ggactattgt | ttccgttatt | 60 |
| cgcaatttct | ataggactac | tatagattat | ataaactgaa | ttttagcttt | atgctgtggt | 120 |
| gttatttccc | aaaacacgct | cttctttctt | acgctttccg | ttagcttatt | tgctcacggt | 180 |
| atcaagatta | cttttttttt | tttcttcttt | tcttttttctt | gcactaccct | cttcttcttg | 240 |
| ttcttccttg | cgttttttacc | cctcttccct | ttattttgca | gcaaaaagaa | agatggaaag | 300 |
| gcaaaagtga | aggcatgatg | atgacaaact | tgaaaagaaa | gagaacagcg | aaaagagatg | 360 |
| aataatccat | ggcaatgact | gcacgctcat | gggtatcaat | tggctaggtc | taatattgtt | 420 |
| attgtttgga | gtatggcgta | gagaagtggt | tccttaacct | taattaatgc | ccgtgccatg | 480 |
| atgattgcat | cactgagacg | taatgtggaa | acaccacttc | tcggtccgcg | gacatcaacc | 540 |
| gaaggaaaaa | tgacaagcta | tttccgtgta | tatccgcgcc | aatcccttcg | gggccgaagt | 600 |
| tcggaggctt | tatctccgct | tagccaaggc | cgtcaaaggc | gataaggtgc | gttgcacccc | 660 |
| aattagccat | ggagaaggaa | aaaaaaagca | tgtatgatca | tgatgatgca | aaaattgaga | 720 |
| ggaaaaatga | ctcaggctat | ttatataagt | aaatgaaagg | gtttcgttgt | agccttttct | 780 |
| gctctcttcc | ttcgctcttc | cgcatatata | tttgtgttca | gagattattc | ttaaatccat | 840 |
| aagaacatcc | cttcatataa | caattgaata | aggaaaacac | aacacataac | acatatttaa | 900 |
| cctg | | | | | | 904 |

<210> SEQ ID NO 16
<211> LENGTH: 999
<212> TYPE: DNA
<213> ORGANISM: Saccharomyces cerevisiae

<400> SEQUENCE: 16

| | | | | | |
|---|---|---|---|---|---|
| tttgtcgccc | ttgagtaaaa | gaaagcgaca | aggtgtgcaa | ttgttatgag | taggattcag | 60 |
| ttataattat | cacttagcat | tgttctaaa | catgaacaca | caacgaatgc | ctgtaaacac | 120 |
| gcttgccgcg | ctagacatgc | aaacgatcct | caaaaaaaaa | aaaacgctcg | tatgaagacc | 180 |
| taatttacgt | atttttttttt | ttttgttttt | cgtttacgcg | ttaattgatc | gattatgagc | 240 |
| ttttggggaa | agtaattgc | cgcagcggct | gtcgtaccgg | aagagtgttg | ttttcatta | 300 |
| ccaaaaaggg | ataatagtgg | ttcctttatg | tgacattggt | aagctgattg | gcataatta | 360 |
| cttgcctgat | gacgaataac | gcgagaactg | cccatataga | atctgacgac | gtaaggagaa | 420 |
| gaaaaagcgg | gaaacggatt | tctcgttcta | ggcctcggcg | gctcttaaaa | ttgtaaaatg | 480 |
| aaaatgagaa | taaaattaaa | ctatacacag | ctgatcagcg | ttctaatgaa | aaaaaatgc | 540 |
| attggaagga | aaagccgaaa | tacttcattt | tctgggcatt | gacgttctgt | tgcctcttgt | 600 |
| gcatacacac | ttgtttttat | tgaaatcgag | cttattgtaa | gagaacttgc | gcttatcttc | 660 |
| aaatgccgct | ttcctcgaaa | aagcatttaa | acatcattca | agattattag | tctatcaagc | 720 |

| | |
|---|---|
| ttgtccagac tgcttgttat tatgtaaaac aagtatgttg gtattgtatt tgattgccga | 780 |
| ttctcatatc gccatacacg aaccaattat gcatcataaa aaaagcgtag ttcttttacc | 840 |
| cgaccaacca acttcttcct ttgtcctcaa tatcaaagaa aaaaaaaaaa acccactgct | 900 |
| cagatgttat aaggaagggg tgttaactta tatacaggtt catctaccag tcaccagtcc | 960 |
| atacaaactt gaaccgtctg cgtaccagtc ctaatcaaa | 999 |

<210> SEQ ID NO 17
<211> LENGTH: 457
<212> TYPE: DNA
<213> ORGANISM: Saccharomyces cerevisiae

<400> SEQUENCE: 17

| | |
|---|---|
| gcttctcatt ctattttaat tatactagta cgatttctca ctctgtaatt taatatcagt | 60 |
| gtaatatgca cctagttatg ggtagttttt gctaacgtta cgagccgcga aactgtcctc | 120 |
| aatcttcacc actacctcta atgactgaag aatgctatgc gatataacgc tgtcgcactt | 180 |
| tgaatatata cttatattta catagttttc aagtgcgtat tactattgca aagtagtatt | 240 |
| ttgtcacgtg attttgatcc aattaaaact aaatatggtt caacccgttg tttccgcatc | 300 |
| aaaaaaccat accatttatc aaggggacgg gatatatcac ataacagttt gaatgcataa | 360 |
| tttgttatag atatcttctg gaataatctt cacagcaaaa gcgcaagtcg aataatatat | 420 |
| cgataaatac aatccataag acttaaaact aacctca | 457 |

<210> SEQ ID NO 18
<211> LENGTH: 438
<212> TYPE: DNA
<213> ORGANISM: Saccharomyces cerevisiae

<400> SEQUENCE: 18

| | |
|---|---|
| gctgggcgat cttccttgtg cgtctgttgt ctcacaattg cttgaaggaa gatttcataa | 60 |
| gatcatatga gtccctcttt atatgggcaa gtggaattat gtgagtcaaa atccgcgcgt | 120 |
| gacccgtaaa gcgttatcag aaggtgcaaa cggtgctatt tagctcataa aaggaatgat | 180 |
| tcaagctctt ttggattgta agacaccttt atttagtcca agatcattgc agacccttgt | 240 |
| tatggtcttt agcagagtcc tcctctatat ctcttcattt actgcaacct gattggcccg | 300 |
| ctaccacgat gcccgctttg ttcctgtggt attaaaagaa tcgatgaaag agactcttat | 360 |
| cttcagggaa aattaggacc gagaattaga gcaagcaaga tatttgcaaa ctactaacta | 420 |
| caagcgactt acacagac | 438 |

<210> SEQ ID NO 19
<211> LENGTH: 546
<212> TYPE: DNA
<213> ORGANISM: Saccharomyces cerevisiae

<400> SEQUENCE: 19

| | |
|---|---|
| tcattctacc atctttcatg tccctacgcc attctcgttc gtataccata taaaccaatt | 60 |
| atagattta catagaataa tagttaaatt tgattataga atatcttcgg attcaataaa | 120 |
| aaattattat tatcagactc tttctgtcca ctccttgaag tatgcaaagt gcttcgagaa | 180 |
| cgccatgaca ttcgacaatt caaaattgag agaggactgc taaggaaact ctttgagttg | 240 |
| attatataat cgctatttaa tcttttaaag ggggaatact gctaaatttt cattattgta | 300 |
| caactggaga catgataggc ctgaaatgtg ccaccaaatt gcatgacctt gctaatgagg | 360 |

```
tcgctgggtt gcgtatgcac ttttacccct gctccgcgtc gaaacagaac ataatacaga      420
gtaaagagga aagagcgaaa atgaaaaagt ttctacactc aaaagtcaaa ccttttaaa       480 aagtgatgtt cagattcctt gtttaagaca ataccattg aggaaggcga ttgaccctaa       540
cgaagt                                                                 546

<210> SEQ ID NO 20
<211> LENGTH: 1000
<212> TYPE: DNA
<213> ORGANISM: Saccharomyces cerevisiae

<400> SEQUENCE: 20
ggccacaatg aaacttcaat tcatatcgac cgactatttt tctccgaacc aaaaaaatag       60
cagggcgaga ttggagctgc ggaaaaaaga ggaaaaaatt ttttcgtagt tttcttgtgc      120
aaattagggt gtaaggtttc tagggcttat tggttcaagc agaagagaca acaattgtag      180
gtcctaaatt caaggcggat gtaaggagta ttggtttcga agttttttcc gaagcggcat      240
ggcagggact acttgcgcat gcgctcggat tatcttcatt tttgcttgca aaaacgtaga      300
atcatggtaa attacatgaa gaattctctt ttttttttt tttttttttt ttttacctct      360
aaagagtgtt gaccaactga aaaaacccct cttcaagaga gttaaactaa gactaaccat      420
cataacttcc aaggaattaa tcgatatctt gcactcctga tttttcttca aagagacagc      480 gcaaggatt atgacactgt tgcattgagt caaaagtttt tccgaagtga cccagtgctc       540
tttttttttt ccgtgaagga ctgacaaata tgcgcacaag atccaatacg taatggaaat      600
tcggaaaaac taggaagaaa tgctgcaggg cattgccgtg ccgatcttt gtctttcaga      660 tatatgagaa aaagaatatt catcaagtgc tgatagaaga ataccactca tatgacgtgg      720
gcagaagaca gcaaacgtaa acatgagctg ctgcgacatt tgatggcttt tatccgacaa      780
gccaggaaac tccaccatta tctaatgtag caaaatattt cttaacaccc gaagttgcgt      840 gtcccctca cgtttttaat catttgaatt agtatattga aattatatat aaaggcaaca      900
atgtccccat aatcaattcc atctggggtc tcatgttctt tccccacctt aaaatctata      960
aagatatcat aatcgtcaac tagttgatat acgtaaaatc                           1000

<210> SEQ ID NO 21
<211> LENGTH: 455
<212> TYPE: DNA
<213> ORGANISM: Saccharomyces cerevisiae

<400> SEQUENCE: 21
cgttcccaaa ccattacatt atgttctttc acttattaca tacgatatat agcatctaca       60
tctacatatc taaatgatgt tttttcccat ctactttgtc cgatacgcat taaaagaaga      120
agatttactc tcccgtgatg ccgggccaat cagacgcgcg cattcgcggc agaataaggg      180
gaggctgctg cgggtaccaa atatccagat attcacaatt atgccaatca actgtctagt      240
tgctgacacc catcgtttcc cactgcaacg aggttttggg gctagaaaag gcgttaacaa      300
tcgttagaga aggagggggtt cataacttga cttgttgtat cttgtttaaa actttctttg      360
aatttgttcg tggttgaatt tgttttttgct atcccaaagg agtgcatttt acacgcatta      420
ctacagcaca cttttataca gttccacaat agaat                                 455

<210> SEQ ID NO 22
<211> LENGTH: 424
<212> TYPE: DNA
<213> ORGANISM: Saccharomyces cerevisiae
```

<400> SEQUENCE: 22

```
atagataaaa aaaaaacgca ccaagtaagt aagtaaataa agaataaata aactatatga    60
gtaaaacacc aagcgaggat gtttcattgt gcatccgtgt tcttgatgat cacataactg   120
taaaagaata atacggcacg ttaaatgtta ttttagaata tataaacacc ttatgtgcca   180
taagcattga gccaatcgct gctgtttttt ttattccggg gcaccttcgg aagaacacag   240
gcgcaattta gttatataag gagaagccct cgagcgatca ggggaccgac tgcggatcgc   300
tttaaggcaa agatagaagg ataaatatct gctttggaag atagtcgtat ctaatttccc   360
attctgttgt tttcttgatc tttcctacgc tttcgacttt cttcctacgc gctttataat   420
agct                                                                 424
```

<210> SEQ ID NO 23
<211> LENGTH: 812
<212> TYPE: DNA
<213> ORGANISM: Saccharomyces cerevisiae

<400> SEQUENCE: 23

```
cttttttgc tctatattta ttggtaacag tgcttattgt tactcaatgt atggtacgct    60
gcatacctat caagatgcga ctacatatat acaattatct catctcatcg cgtattgaaa   120
aattttccat cttctaattt ttcagaaccc ataaattcgg gtaacgatca gtggaaaaaa   180
cttaaatccg cagtaatagg cttgcaaagg accaaagaca gcatatgcag cagttaagaa   240
atctaagaat gcattgtata ttagagtagt atatggaaaa gctcggactg ggagccgtaa   300
aatctctttc ccgtaagatc tggctgcaaa cctggtctac ataaatgtag tacattataa   360
gggactacca agaaatacga agcgctcaga tatctcttaa agttcatttt tttgccggaa   420
taatcttggt ttagtaactt ataaaactac ttacgtccaa taaatcgtta tatttatgc    480
cgtcgtcata aagtggacac tttcgagaga cggtgctggc caataagatg ctgatatttg   540
aaatatcatt tacccgggcc cgggtgggaa aaacaaggaa ttaaagataa tgaagtgatc   600
tttttggcgag atagtaaaac tttcaattat ctaggaacaa tttcaaacgc caattgttaa   660
ctttgtgtac agtatttcta gtttttatct cattgaaaac aaaattcagt caacttggaa   720
atttaagcag gctactgtgg cattgagata ttttccgca gagtaagaac cgattagcaa   780
gttaccgcat tattttaaa ccgtggacaa tc                                  812
```

<210> SEQ ID NO 24
<211> LENGTH: 1000
<212> TYPE: DNA
<213> ORGANISM: Saccharomyces cerevisiae

<400> SEQUENCE: 24

```
tttgatggaa gacgaggta atgaagaata caccaaagat ttggaagaag cagctaacaa    60
agctcaacca cagtagaatg gaatattgaa actggagtga cttctgatga agtttccaat   120
tatttatatg tatacattat ttatttgtct atcattaaaa tttctgtcaa gtaatggctt   180
tttatgttta tttcatggat tacgaaattt gctggctttt tagagtgacc gatgagttgc   240
atgtacatat gtgcgaaata aaacaatacg gtagtaaaac atgaatactt cgagaagtaa   300
attcaagatt gcaggcgtag cacaagaatg tccttccgcc tgctagtgtg ttgagcaaag   360
cacgccatca ctaatggaac ccttacaaaa tctcgcatgg agcagcaaac cttaaatcca   420
ttttctatca ttcgttcctg aggacccgga tatcgtttta gagacaaaaa tagatactac   480
```

```
aagaggaata gggatatctg cacatggggc ctcgagcatg gctcattttc gattttccgg      540
cacgatgctg acttagtact atcatgccag gcaggacagg ccttatgggg ttcttgcagc      600
ttaccaattc tgacactgga ctgccctgg attagcgacc ccgcgacccc gcgaccagac      660
tccctgaaaa tggtaattgg tgatgatata tgtgactgag ttcagcctgg gcatacaatg      720 tttaacccctt ttggacatgg aattaggcca gcaaagggag cagctttccc cgaaagcgta     780 gttttctcc aggaacgcaa ttcaccccctt tcttcttat gcaagctcct cgtacatata      840
taaaaatata tgagtatata tagtgcttct acagcataat caatttaagg ttccttgcct     900
ttccttaaat atgttagcta tctctaaagc atcactgaga agtggtagtt tttttgataa     960
ctgtgattga agttttgact acctcagaga aaaattttga                          1000

<210> SEQ ID NO 25
<211> LENGTH: 1000
<212> TYPE: DNA
<213> ORGANISM: Saccharomyces cerevisiae

<400> SEQUENCE: 25
aagatctgtt acgtagtatt tgagagaagg agtaaactaa ccttgaattg aggtcttgat       60
tacaagttgc ttgcttagtg acacatttga caagaaaaaa cagtaatacg ccagaacatt      120
tgcggcccct ttttatatca aaagtgctaa acatgctatt taagtatttc ttttgctgtt      180
gatacgcaat tttcattgcg ctgctgcaga tgtggtaccc tttaccgcac aaaaatactt      240
ctatctggat attattccgt gtacttggcg aagaagccat cccgttttga acgccattgc      300
cgctaacctc cgcgctttcg cttgcagcaa tggctacatc cgcacggttc cgctattgcc      360
acgacattgt ggtggtaata gccaaggcaa tggtgtgtac aacttacgat ccctctgctt      420
gcggaagcag tcaaaaggca agtgagatct actctataaa ctgacacttt atccagggaa      480
ttatcgagaa aattctgtct tgtcaattag agaagtaagg ggccacaggg aataatact       540 ttcgaaggga gtttctttcc ttaaggaggt gcaaaatgca aaagatatac agtttatagg      600
ttgatacaca tagagcaagt ggtctcaagt ggtcttaatg agtcacggga ggtcaagatg      660
ctcttttttt cttcatcgtt tcagttttgt atcttgagcg gagtgaactt gccctttaag      720
cgggccatac ccttacatgg cgttagcact tattttcaag gtgaatatat acaatgtcag      780
ttacccgttt ttttgtcttc cgctgtataa gcttgctatc attaaaagcc gcatgtggca      840
tcctgaattc tgccaccct taaatacaaa aaatagtgta aatggtactt gatctcttct      900
ggaggaataa acaataattc ttgatggaat ttgagagaaa gtaagtgttc ggctaagcac      960
aataaagata taaacctgtg actacctata taagttcgta                          1000

<210> SEQ ID NO 26
<211> LENGTH: 278
<212> TYPE: DNA
<213> ORGANISM: Saccharomyces cerevisiae

<400> SEQUENCE: 26
ttccaatatt agatgcctgt gaaactactg tcaaacttat tgtgtaaca atactcatcg       60 tctaatttgt ccattattgt tatatactct gtcataaaaa aagaaagaaa atcttatac      120 tttcgtcgac tgtgatttga aaatctctcc agatcaaacg ggaataaaag ggtttatatc     180
cgaaggtggc cagaacaatc atgaagcaaa taggataaaa atagccaata agatgtttgt     240
tgtctttcat cccaaagttc caacagcata tttcaaag                            278
```

<210> SEQ ID NO 27
<211> LENGTH: 186
<212> TYPE: PRT
<213> ORGANISM: Saccharomyces cerevisiae

<400> SEQUENCE: 27

Met Ser Ala Asn Asn Gly Val Thr Gly Lys Leu Ser Ser Arg Val Met
1               5                   10                  15

Asn Met Lys Phe Met Lys Phe Gly Lys Thr Asp Asp Glu Glu Ser Ser
            20                  25                  30

Asn Ser Asn Thr Pro Ser Asn Ile Asn Ser Asp Val Glu Pro Ile Glu
        35                  40                  45

Gln Lys Gly Lys Leu Phe Gly Leu Asp Asp Ser Ala Trp Asp Leu Asn
    50                  55                  60

Ser Tyr Lys Asp Asp Leu Lys Lys Ile Ser Gly Lys Glu Lys Lys Lys
65                  70                  75                  80

Val Lys Arg Val Val Tyr Lys Lys Arg Pro Asn Leu Ile Ile Ser Asn
                85                  90                  95

Val Gly Tyr Ser Glu Leu Arg Lys Pro Glu Val Ile Ser Gly Arg
            100                 105                 110

Lys Thr Phe Gly Asp Asn Ser Asp Ser Gly Ser Arg Lys Arg Lys
            115                 120                 125

Phe Asp Glu Gly Glu Gln Asn Glu Asp Lys Arg Asp Ala Lys Asp
130                 135                 140

Lys Glu Phe Thr Gly Ser Gln Asp Asp Gly Glu Asp Glu Tyr Asp Leu
145                 150                 155                 160

Asp Lys Leu Phe Lys Asp Ser Ile Lys Lys Lys Thr Asn His Asn
                165                 170                 175

Gly Lys Asn Lys Asn Arg Asn Ser Lys Lys
            180                 185

<210> SEQ ID NO 28
<211> LENGTH: 125
<212> TYPE: PRT
<213> ORGANISM: Saccharomyces cerevisiae

<400> SEQUENCE: 28

Met Phe Arg Ser Val Cys Arg Ile Ser Ser Arg Val Ala Pro Ser Ala
1               5                   10                  15

Tyr Arg Thr Ile Met Gly Arg Ser Val Met Ser Asn Thr Ile Leu Ala
            20                  25                  30

Gln Arg Phe Tyr Ser Ala Asn Leu Ser Lys Asp Gln Val Ser Gln Arg
        35                  40                  45

Val Ile Asp Val Ile Lys Ala Phe Asp Lys Asn Ser Pro Asn Ile Ala
    50                  55                  60

Asn Lys Gln Ile Ser Ser Asp Thr Gln Phe His Lys Asp Leu Gly Leu
65                  70                  75                  80

Asp Ser Leu Asp Thr Val Glu Leu Leu Val Ala Ile Glu Glu Glu Phe
                85                  90                  95

Asp Ile Glu Ile Pro Asp Lys Val Ala Asp Glu Leu Arg Ser Val Gly
            100                 105                 110

Glu Thr Val Asp Tyr Ile Ala Ser Asn Pro Asp Ala Asn
            115                 120                 125

<210> SEQ ID NO 29
<211> LENGTH: 391
<212> TYPE: PRT

<213> ORGANISM: Saccharomyces cerevisiae

<400> SEQUENCE: 29

```
Met Gly Tyr Phe Val Pro Asp Ser His Ile Glu Asn Leu Lys Ser Tyr
 1               5                  10                  15
Lys Tyr Gln Ser Glu Asp Arg Ser Leu Val Ser Lys Tyr Phe Leu Lys
            20                  25                  30
Pro Phe Trp Gln Arg Phe Cys His Ile Phe Pro Thr Trp Met Ala Pro
        35                  40                  45
Asn Ile Ile Thr Leu Ser Gly Phe Ala Phe Ile Val Ile Asn Val Leu
    50                  55                  60
Thr Val Phe Tyr Tyr Asp Pro Asn Leu Asn Thr Asp Thr Pro Arg Trp
65                  70                  75                  80
Thr Tyr Phe Ser Tyr Ala Leu Gly Val Phe Leu Tyr Gln Thr Phe Asp
                85                  90                  95
Gly Cys Asp Gly Val His Ala Arg Arg Ile Asn Gln Ser Gly Pro Leu
           100                 105                 110
Gly Glu Leu Phe Asp His Ser Ile Asp Ala Ile Asn Ser Thr Leu Ser
       115                 120                 125
Ile Phe Ile Phe Ala Ser Glu Thr Gly Met Gly Phe Ser Tyr Asn Leu
   130                 135                 140
Met Leu Ser Gln Phe Ala Met Leu Thr Asn Phe Tyr Leu Ser Thr Trp
145                 150                 155                 160
Glu Glu Tyr His Thr His Thr Leu Tyr Leu Ser Glu Phe Ser Gly Pro
                165                 170                 175
Val Glu Gly Ile Leu Ile Val Cys Val Ser Leu Ile Leu Thr Gly Ile
            180                 185                 190
Tyr Gly Lys Gln Val Ile Trp His Thr Tyr Leu Phe Thr Ile Thr Val
        195                 200                 205
Gly Asp Lys Val Ile Asp Val Asp Thr Leu Asp Ile Val Phe Ser Leu
    210                 215                 220
Ala Val Phe Gly Leu Val Met Asn Ala Leu Ser Ala Lys Arg Asn Val
225                 230                 235                 240
Asp Lys Tyr Arg Asn Ser Thr Ser Ser Ala Asn Asn Ile Thr Gln
                245                 250                 255
Ile Glu Gln Asp Ser Ala Ile Lys Gly Leu Leu Pro Phe Phe Ala Tyr
            260                 265                 270
Tyr Ala Ser Ile Ala Leu Leu Val Trp Met Gln Pro Ser Phe Ile Thr
        275                 280                 285
Leu Ser Phe Ile Leu Ser Val Gly Phe Thr Gly Ala Phe Thr Val Gly
    290                 295                 300
Arg Ile Ile Val Cys His Leu Thr Lys Gln Ser Phe Pro Met Phe Asn
305                 310                 315                 320
Ala Pro Met Leu Ile Pro Leu Cys Gln Ile Val Leu Tyr Lys Ile Cys
                325                 330                 335
Leu Ser Leu Trp Gly Ile Glu Ser Asn Lys Ile Val Phe Ala Leu Ser
            340                 345                 350
Trp Leu Gly Phe Gly Leu Ser Leu Gly Val His Ile Met Phe Met Asn
        355                 360                 365
Asp Ile Ile His Glu Phe Thr Glu Tyr Leu Asp Val Tyr Ala Leu Ser
    370                 375                 380
Ile Lys Arg Ser Lys Leu Thr
385                 390
```

<210> SEQ ID NO 30
<211> LENGTH: 700
<212> TYPE: PRT
<213> ORGANISM: Saccharomyces cerevisiae

<400> SEQUENCE: 30

Met Val Ala Gln Tyr Thr Val Pro Val Gly Lys Ala Ala Asn Glu His
1               5                   10                  15

Glu Thr Ala Pro Arg Arg Asn Tyr Gln Cys Arg Glu Lys Pro Leu Val
            20                  25                  30

Arg Pro Pro Asn Thr Lys Cys Ser Thr Val Tyr Glu Phe Val Leu Glu
        35                  40                  45

Cys Phe Gln Lys Asn Lys Asn Ser Asn Ala Met Gly Trp Arg Asp Val
    50                  55                  60

Lys Glu Ile His Glu Glu Ser Lys Ser Val Met Lys Lys Val Asp Gly
65                  70                  75                  80

Lys Glu Thr Ser Val Glu Lys Lys Trp Met Tyr Tyr Glu Leu Ser His
                85                  90                  95

Tyr His Tyr Asn Ser Phe Asp Gln Leu Thr Asp Ile Met His Glu Ile
            100                 105                 110

Gly Arg Gly Leu Val Lys Ile Gly Leu Lys Pro Asn Asp Asp Asp Lys
        115                 120                 125

Leu His Leu Tyr Ala Ala Thr Ser His Lys Trp Met Lys Met Phe Leu
    130                 135                 140

Gly Ala Gln Ser Gln Gly Ile Pro Val Val Thr Ala Tyr Asp Thr Leu
145                 150                 155                 160

Gly Glu Lys Gly Leu Ile His Ser Leu Val Gln Thr Gly Ser Lys Ala
                165                 170                 175

Ile Phe Thr Asp Asn Ser Leu Leu Pro Ser Leu Ile Lys Pro Val Gln
            180                 185                 190

Ala Ala Gln Asp Val Lys Tyr Ile Ile His Phe Asp Ser Ile Ser Ser
        195                 200                 205

Glu Asp Arg Arg Gln Ser Gly Lys Ile Tyr Gln Ser Ala His Asp Ala
    210                 215                 220

Ile Asn Arg Ile Lys Glu Val Arg Pro Asp Ile Lys Thr Phe Ser Phe
225                 230                 235                 240

Asp Asp Ile Leu Lys Leu Gly Lys Glu Ser Cys Asn Glu Ile Asp Val
                245                 250                 255

His Pro Pro Gly Lys Asp Asp Leu Cys Cys Ile Met Tyr Thr Ser Gly
            260                 265                 270

Ser Thr Gly Glu Pro Lys Gly Val Val Leu Lys His Ser Asn Val Val
        275                 280                 285

Ala Gly Val Gly Gly Ala Ser Leu Asn Val Leu Lys Phe Val Gly Asn
    290                 295                 300

Thr Asp Arg Val Ile Cys Phe Leu Pro Leu Ala His Ile Phe Glu Leu
305                 310                 315                 320

Val Phe Glu Leu Leu Ser Phe Tyr Trp Gly Ala Cys Ile Gly Tyr Ala
                325                 330                 335

Thr Val Lys Thr Leu Thr Ser Ser Val Arg Asn Cys Gln Gly Asp
            340                 345                 350

Leu Gln Glu Phe Lys Pro Thr Ile Met Val Gly Val Ala Ala Val Trp
        355                 360                 365

Glu Thr Val Arg Lys Gly Ile Leu Asn Gln Ile Asp Asn Leu Pro Phe
    370                 375                 380

-continued

```
Leu Thr Lys Lys Ile Phe Trp Thr Ala Tyr Asn Thr Lys Leu Asn Met
385                 390                 395                 400

Gln Arg Leu His Ile Pro Gly Gly Gly Ala Leu Gly Asn Leu Val Phe
            405                 410                 415

Lys Lys Ile Arg Thr Ala Thr Gly Gly Gln Leu Arg Tyr Leu Leu Asn
        420                 425                 430

Gly Gly Ser Pro Ile Ser Arg Asp Ala Gln Glu Phe Ile Thr Asn Leu
    435                 440                 445

Ile Cys Pro Met Leu Ile Gly Tyr Gly Leu Thr Glu Thr Cys Ala Ser
450                 455                 460

Thr Thr Ile Leu Asp Pro Ala Asn Phe Glu Leu Gly Val Ala Gly Asp
465                 470                 475                 480

Leu Thr Gly Cys Val Thr Val Lys Leu Val Asp Val Glu Glu Leu Gly
            485                 490                 495

Tyr Phe Ala Lys Asn Asn Gln Gly Glu Val Trp Ile Thr Gly Ala Asn
        500                 505                 510

Val Thr Pro Glu Tyr Tyr Lys Asn Glu Glu Thr Ser Gln Ala Leu
    515                 520                 525

Thr Ser Asp Gly Trp Phe Lys Thr Gly Asp Ile Gly Glu Trp Glu Ala
530                 535                 540

Asn Gly His Leu Lys Ile Ile Asp Arg Lys Lys Asn Leu Val Lys Thr
545                 550                 555                 560

Met Asn Gly Glu Tyr Ile Ala Leu Glu Lys Leu Glu Ser Val Tyr Arg
            565                 570                 575

Ser Asn Glu Tyr Val Ala Asn Ile Cys Val Tyr Ala Asp Gln Ser Lys
        580                 585                 590

Thr Lys Pro Val Gly Ile Ile Val Pro Asn His Ala Pro Leu Thr Lys
    595                 600                 605

Leu Ala Lys Lys Leu Gly Ile Met Glu Gln Lys Asp Ser Ser Ile Asn
610                 615                 620

Ile Glu Asn Tyr Leu Glu Asp Ala Lys Leu Ile Lys Ala Val Tyr Ser
625                 630                 635                 640

Asp Leu Leu Lys Thr Gly Lys Asp Gln Gly Leu Val Gly Ile Glu Leu
            645                 650                 655

Leu Ala Gly Ile Val Phe Phe Asp Gly Glu Trp Thr Pro Gln Asn Gly
        660                 665                 670

Phe Val Thr Ser Ala Gln Lys Leu Lys Arg Lys Asp Ile Leu Asn Ala
    675                 680                 685

Val Lys Asp Lys Val Asp Ala Val Tyr Ser Ser Ser
690                 695                 700

<210> SEQ ID NO 31
<211> LENGTH: 185
<212> TYPE: PRT
<213> ORGANISM: Saccharomyces cerevisiae

<400> SEQUENCE: 31

Met Asn Ile Ser Gly Thr Leu Asn Thr Leu Arg Leu Leu Tyr Asn Pro
1               5                   10                  15

Ser Leu Cys Lys Pro Ser Leu Val Val Pro Thr Phe Asn Asp Leu Pro
            20                  25                  30

Ile Pro Ile His Asp Ser Ile Lys Ala Val Val Leu Asp Lys Asp Asn
        35                  40                  45

Cys Ile Ala Phe Pro His Asp Asp Lys Ile Trp Pro Asp Tyr Leu Gln
```

```
            50                  55                  60
His Trp Glu Thr Leu Arg Ser Lys Tyr Ser Asn Lys Ala Leu Leu Ile
 65                  70                  75                  80

Val Ser Asn Thr Ala Gly Ser Asn Ser Asp Lys Asp Tyr Ser Gln Ala
                 85                  90                  95

Lys Leu Leu Glu Asp Lys Thr Gly Ile Pro Val Leu Arg His Ser Thr
            100                 105                 110

Lys Lys Pro Gly Cys His Asn Glu Ile Leu Asp Tyr Phe Tyr Arg Asn
        115                 120                 125

Lys Thr Ile Thr Asn Pro Lys Glu Val Ala Val Gly Asp Arg Leu
    130                 135                 140

Phe Thr Asp Ile Leu Met Ala Asn Leu Met Gly Ser Tyr Gly Val Trp
145                 150                 155                 160

Ile Arg Asp Gly Val Lys Val Ser Ala Asn Pro Leu Ser Lys Phe Glu
                165                 170                 175

Lys Lys Leu Tyr Asn Phe Leu Gly Phe
            180                 185

<210> SEQ ID NO 32
<211> LENGTH: 420
<212> TYPE: PRT
<213> ORGANISM: Saccharomyces cerevisiae

<400> SEQUENCE: 32

Met Ser Lys Ile Lys Val Val His Pro Ile Val Glu Met Asp Gly Asp
  1               5                  10                  15

Glu Gln Thr Arg Val Ile Trp Lys Leu Ile Lys Glu Lys Leu Ile Leu
                 20                  25                  30

Pro Tyr Leu Asp Val Asp Leu Lys Tyr Tyr Asp Leu Ser Ile Gln Glu
             35                  40                  45

Arg Asp Arg Thr Asn Asp Gln Val Thr Lys Asp Ser Ser Tyr Ala Thr
         50                  55                  60

Leu Lys Tyr Gly Val Ala Val Lys Cys Ala Thr Ile Thr Pro Asp Glu
 65                  70                  75                  80

Ala Arg Met Lys Glu Phe Asn Leu Lys Glu Met Trp Lys Ser Pro Asn
                 85                  90                  95

Gly Thr Ile Arg Asn Ile Leu Gly Gly Thr Val Phe Arg Glu Pro Ile
            100                 105                 110

Ile Ile Pro Lys Ile Pro Arg Leu Val Pro His Trp Glu Lys Pro Ile
        115                 120                 125

Ile Ile Gly Arg His Ala Phe Gly Asp Gln Tyr Arg Ala Thr Asp Ile
    130                 135                 140

Lys Ile Lys Lys Ala Gly Lys Leu Arg Leu Gln Phe Ser Ser Asp Asp
145                 150                 155                 160

Gly Lys Glu Asn Ile Asp Leu Lys Val Tyr Glu Phe Pro Lys Ser Gly
                165                 170                 175

Gly Ile Ala Met Ala Met Phe Asn Thr Asn Asp Ser Ile Lys Gly Phe
            180                 185                 190

Ala Lys Ala Ser Phe Glu Leu Ala Leu Lys Arg Lys Leu Pro Leu Phe
        195                 200                 205

Phe Thr Thr Lys Asn Thr Ile Leu Lys Asn Tyr Asp Asn Gln Phe Lys
    210                 215                 220

Gln Ile Phe Asp Asn Leu Phe Asp Lys Glu Tyr Lys Glu Lys Phe Gln
225                 230                 235                 240
```

Ala Leu Lys Ile Thr Tyr Glu His Arg Leu Ile Asp Asp Met Val Ala
            245                 250                 255

Gln Met Leu Lys Ser Lys Gly Gly Phe Ile Ile Ala Met Lys Asn Tyr
        260                 265                 270

Asp Gly Asp Val Gln Ser Asp Ile Val Ala Gln Gly Phe Gly Ser Leu
    275                 280                 285

Gly Leu Met Thr Ser Ile Leu Ile Thr Pro Asp Gly Lys Thr Phe Glu
290                 295                 300

Ser Glu Ala Ala His Gly Thr Val Thr Arg His Phe Arg Lys His Gln
305                 310                 315                 320

Arg Gly Glu Glu Thr Ser Thr Asn Ser Ile Ala Ser Ile Phe Ala Trp
                325                 330                 335

Thr Arg Ala Ile Ile Gln Arg Gly Lys Leu Asp Asn Thr Asp Asp Val
            340                 345                 350

Ile Lys Phe Gly Asn Leu Leu Glu Lys Ala Thr Leu Asp Thr Val Gln
        355                 360                 365

Val Gly Gly Lys Met Thr Lys Asp Leu Ala Leu Met Leu Gly Lys Thr
    370                 375                 380

Asn Arg Ser Ser Tyr Val Thr Thr Glu Glu Phe Ile Asp Glu Val Ala
385                 390                 395                 400

Lys Arg Leu Gln Asn Met Met Leu Ser Ser Asn Glu Asp Lys Lys Gly
                405                 410                 415

Met Cys Lys Leu
            420

<210> SEQ ID NO 33
<211> LENGTH: 384
<212> TYPE: PRT
<213> ORGANISM: Saccharomyces cerevisiae

<400> SEQUENCE: 33

Met Asn Lys Thr Asn Trp Lys Val Ser Val Thr Thr Phe Asn Cys Gly
1               5                   10                  15

Lys Glu Phe Pro Val Glu Asn Ser Lys Ala Ile Val Lys Gln Leu Leu
            20                  25                  30

Phe Pro Tyr Asp Asp Gly Ile Ser Gln Leu Glu Leu Gln Asp Leu Tyr
        35                  40                  45

Val Leu Gly Phe Gln Glu Val Val Pro Ile Trp Gln Gly Ser Phe Pro
    50                  55                  60

Ala Val Asn Arg Asp Leu Ile Asp Arg Ile Thr Thr Thr Ala Val Asn
65                  70                  75                  80

Cys Leu Asn Glu Lys Val Ser Ala Thr Gln Gly Asp Glu Gln Tyr Ser
                85                  90                  95

Cys Leu Gly Val Asn Ser Leu Gly Ala Ile Thr Ile Val Leu Tyr
            100                 105                 110

Asn Asn Asn Ala Leu Lys Val Lys Asp Asp Ile Leu Lys Arg Asn Gly
        115                 120                 125

Lys Cys Gly Trp Phe Gly Thr His Leu Lys Gly Gly Thr Leu Ile Ser
    130                 135                 140

Phe Gln Met Thr Arg Asn Gly Glu Glu Asn Trp Glu Arg Phe Ser Tyr
145                 150                 155                 160

Ile Cys Ala His Leu Asn Ala Asn Glu Gly Val Asn Asn Arg Asn Gln
                165                 170                 175

Arg Ile Asp Asp Tyr Lys Arg Ile Met Ser Glu Val Cys Asp Ser Glu
            180                 185                 190

Val Ala Lys Ser Asp His Phe Phe Phe Leu Gly Asp Leu Asn Phe Arg
            195                 200                 205

Val Thr Ser Thr Tyr Asp Pro Thr Thr Asn Tyr Ser Ser Thr Thr Thr
            210                 215                 220

Leu Arg Arg Leu Leu Glu Asn His Glu Glu Leu Asn Leu Leu Arg Lys
225                 230                 235                 240

Gly Glu Asp Glu Pro Leu Cys Lys Gly Phe Gln Glu Leu Lys Ile Thr
                245                 250                 255

Phe Pro Pro Thr Tyr Lys Phe Lys Leu Phe Glu Lys Glu Thr Tyr Asn
                260                 265                 270

Thr Lys Arg Ile Pro Ser Trp Cys Asp Arg Ile Leu Tyr Lys Ser Tyr
            275                 280                 285

Ala Val Pro Thr Phe Ala Gln Glu Gly Thr Tyr His Ser Val Pro Arg
            290                 295                 300

Ser Asn Ala Leu Leu Phe Ser Asp His Gln Pro Val Asn Leu Thr Val
305                 310                 315                 320

Arg Leu Pro Arg Ser Thr Gly Thr Pro Val Pro Leu Ser Leu His Ile
                325                 330                 335

Glu Lys Tyr Pro Leu Ser Trp Ser Ser Gly Leu Ile Gly Gln Ile Gly
                340                 345                 350

Asp Ala Val Ile Gly Tyr Cys Gly Trp Leu Val Thr Lys Asn Val His
            355                 360                 365

Tyr Trp Ile Leu Gly Ser Leu Leu Leu Tyr Leu Leu Leu Lys Ile Leu
            370                 375                 380

<210> SEQ ID NO 34
<211> LENGTH: 274
<212> TYPE: PRT
<213> ORGANISM: Saccharomyces cerevisiae

<400> SEQUENCE: 34

Met Ile Ser Val Met Ala Asp Glu Lys His Lys Glu Tyr Phe Lys Leu
1               5                   10                  15

Tyr Tyr Phe Gln Tyr Met Ile Ile Gly Leu Cys Thr Ile Leu Phe Leu
                20                  25                  30

Tyr Ser Glu Ile Ser Leu Val Pro Arg Gly Gln Asn Ile Glu Phe Ser
            35                  40                  45

Leu Asp Asp Pro Ser Ile Ser Lys Arg Tyr Val Pro Asn Glu Leu Val
50                  55                  60

Gly Pro Leu Glu Cys Leu Ile Leu Ser Val Gly Leu Ser Asn Met Val
65                  70                  75                  80

Val Phe Trp Thr Cys Met Phe Asp Lys Asp Leu Leu Lys Lys Asn Arg
                85                  90                  95

Val Lys Arg Leu Arg Glu Arg Pro Asp Gly Ile Ser Asn Asp Phe His
            100                 105                 110

Phe Met His Thr Ser Ile Leu Cys Leu Met Leu Ile Ile Ser Ile Asn
        115                 120                 125

Ala Ala Leu Thr Gly Ala Leu Lys Leu Ile Gly Asn Leu Arg Pro
    130                 135                 140

Asp Phe Val Asp Arg Cys Ile Pro Asp Leu Gln Lys Met Ser Asp Ser
145                 150                 155                 160

Asp Ser Leu Val Phe Gly Leu Asp Ile Cys Lys Gln Thr Asn Lys Trp
                165                 170                 175

Ile Leu Tyr Glu Gly Leu Lys Ser Thr Pro Ser Gly His Ser Ser Phe

```
                    180                 185                 190
Ile Val Ser Thr Met Gly Phe Thr Tyr Leu Trp Gln Arg Val Phe Thr
                195                 200                 205

Thr Arg Asn Thr Arg Ser Cys Ile Trp Cys Pro Leu Leu Ala Leu Val
            210                 215                 220

Val Met Val Ser Arg Val Ile Asp His Arg His His Trp Tyr Asp Val
225                 230                 235                 240

Val Ser Gly Ala Val Leu Ala Phe Leu Val Ile Tyr Cys Cys Trp Lys
                245                 250                 255

Trp Thr Phe Thr Asn Leu Ala Lys Arg Asp Ile Leu Pro Ser Pro Val
            260                 265                 270

Ser Val

<210> SEQ ID NO 35
<211> LENGTH: 302
<212> TYPE: PRT
<213> ORGANISM: Saccharomyces cerevisiae

<400> SEQUENCE: 35

Met Phe Ser Arg Leu Ser Arg Ser His Ser Lys Ala Leu Pro Ile Ala
1               5                   10                  15

Leu Gly Thr Val Ala Ile Ala Ala Thr Ala Phe Tyr Phe Ala Asn
            20                  25                  30

Arg Asn Gln His Ser Phe Val Phe Asn Glu Ser Asn Lys Val Phe Lys
            35                  40                  45

Gly Asp Asp Lys Trp Ile Asp Leu Pro Ile Ser Lys Ile Glu Glu Glu
        50                  55                  60

Ser His Asp Thr Arg Arg Phe Thr Phe Lys Leu Pro Thr Glu Asp Ser
65                  70                  75                  80

Glu Met Gly Leu Val Leu Ala Ser Ala Leu Phe Ala Lys Phe Val Thr
                85                  90                  95

Pro Lys Gly Ser Asn Val Val Arg Pro Tyr Thr Pro Val Ser Asp Leu
            100                 105                 110

Ser Gln Lys Gly His Phe Gln Leu Val Val Lys His Tyr Glu Gly Gly
            115                 120                 125

Lys Met Thr Ser His Leu Phe Gly Leu Lys Pro Asn Asp Thr Val Ser
130                 135                 140

Phe Lys Gly Pro Ile Met Lys Trp Lys Trp Gln Pro Asn Gln Phe Lys
145                 150                 155                 160

Ser Ile Thr Leu Leu Gly Ala Gly Thr Gly Ile Asn Pro Leu Tyr Gln
                165                 170                 175

Leu Ala His His Ile Val Glu Asn Pro Asn Asp Lys Thr Lys Val Asn
            180                 185                 190

Leu Leu Tyr Gly Asn Lys Thr Pro Gln Asp Ile Leu Leu Arg Lys Glu
            195                 200                 205

Leu Asp Ala Leu Lys Glu Lys Tyr Pro Asp Lys Phe Asn Val Thr Tyr
        210                 215                 220

Phe Val Asp Asp Lys Gln Asp Gln Asp Phe Asp Gly Glu Ile Ser
225                 230                 235                 240

Phe Ile Ser Lys Asp Phe Ile Gln Glu His Val Pro Gly Pro Lys Glu
                245                 250                 255

Ser Thr His Leu Phe Val Cys Gly Pro Pro Pro Phe Met Asn Ala Tyr
            260                 265                 270

Ser Gly Glu Lys Lys Ser Pro Lys Asp Gln Gly Glu Leu Ile Gly Ile
```

```
                    275                 280                 285
Leu Asn Asn Leu Gly Tyr Ser Lys Asp Gln Val Phe Lys Phe
    290                 295                 300

<210> SEQ ID NO 36
<211> LENGTH: 222
<212> TYPE: PRT
<213> ORGANISM: Saccharomyces cerevisiae

<400> SEQUENCE: 36

Met Thr Glu Leu Asp Tyr Gln Gly Thr Ala Glu Ala Ser Thr Ser
1               5                   10                  15

Tyr Ser Arg Asn Gln Thr Asp Leu Lys Pro Phe Pro Ser Ala Gly Ser
                20                  25                  30

Ala Ser Ser Ser Ile Lys Thr Thr Glu Pro Val Lys Asp His Arg Arg
            35                  40                  45

Arg Arg Ser Ser Ser Ile Ile Ser His Val Glu Pro Glu Thr Phe Glu
    50                  55                  60

Asp Glu Asn Asp Gln Gln Leu Leu Pro Asn Met Asn Ala Thr Trp Val
65                  70                  75                  80

Asp Gln Arg Gly Ala Trp Ile Ile His Val Val Ile Ile Leu Leu
                85                  90                  95

Lys Leu Phe Tyr Asn Leu Phe Pro Gly Val Thr Thr Glu Trp Ser Trp
            100                 105                 110

Thr Leu Thr Asn Met Thr Tyr Val Ile Gly Ser Tyr Val Met Phe His
        115                 120                 125

Leu Ile Lys Gly Thr Pro Phe Asp Phe Asn Gly Gly Ala Tyr Asp Asn
    130                 135                 140

Leu Thr Met Trp Glu Gln Ile Asp Asp Glu Thr Leu Tyr Thr Pro Ser
145                 150                 155                 160

Arg Lys Phe Leu Ile Ser Val Pro Ile Ala Leu Phe Leu Val Ser Thr
                165                 170                 175

His Tyr Ala His Tyr Asp Leu Lys Leu Phe Ser Trp Asn Cys Phe Leu
            180                 185                 190

Thr Thr Phe Gly Ala Val Val Pro Lys Leu Pro Val Thr His Arg Leu
        195                 200                 205

Arg Ile Ser Ile Pro Gly Ile Thr Gly Arg Ala Gln Ile Ser
    210                 215                 220

<210> SEQ ID NO 37
<211> LENGTH: 111
<212> TYPE: PRT
<213> ORGANISM: Saccharomyces cerevisiae

<400> SEQUENCE: 37

Met Ser Thr Val Thr Lys Tyr Phe Tyr Lys Gly Glu Asn Thr Asp Leu
1               5                   10                  15

Ile Val Phe Ala Ala Ser Glu Glu Leu Val Asp Glu Tyr Leu Lys Asn
                20                  25                  30

Pro Ser Ile Gly Lys Leu Ser Glu Val Val Glu Leu Phe Glu Val Phe
            35                  40                  45

Thr Pro Gln Asp Gly Arg Gly Ala Glu Gly Glu Leu Gly Ala Ala Ser
        50                  55                  60

Lys Ala Gln Val Glu Asn Glu Phe Gly Lys Gly Lys Lys Ile Glu Glu
65                  70                  75                  80

Val Ile Asp Leu Ile Leu Arg Asn Gly Lys Pro Asn Ser Thr Thr Ser
```

```
                  85                  90                  95

Ser Leu Lys Thr Lys Gly Gly Asn Ala Gly Thr Lys Ala Tyr Asn
            100                 105                 110

<210> SEQ ID NO 38
<211> LENGTH: 259
<212> TYPE: PRT
<213> ORGANISM: Saccharomyces cerevisiae

<400> SEQUENCE: 38

Met Glu Pro Glu Ser Ile Gly Asp Val Gly Asn His Ala Gln Asp Asp
1               5                   10                  15

Ser Ala Ser Ile Val Ser Gly Pro Arg Arg Ser Thr Ser Lys Thr
            20                  25                  30

Ser Ser Ala Lys Asn Ile Arg Asn Ser Ser Asn Ile Ser Pro Ala Ser
            35                  40                  45

Met Ile Phe Arg Asn Leu Leu Ile Leu Glu Asp Asp Leu Arg Arg Gln
50                  55                  60

Ala His Glu Gln Lys Ile Leu Lys Trp Gln Phe Thr Leu Phe Leu Ala
65                  70                  75                  80

Ser Met Ala Gly Val Gly Ala Phe Thr Phe Tyr Glu Leu Tyr Phe Thr
                85                  90                  95

Ser Asp Tyr Val Lys Gly Leu His Arg Val Ile Leu Gln Phe Thr Leu
            100                 105                 110

Ser Phe Ile Ser Ile Thr Val Val Leu Phe His Ile Ser Gly Gln Tyr
            115                 120                 125

Arg Arg Thr Ile Val Ile Pro Arg Arg Phe Phe Thr Ser Thr Asn Lys
            130                 135                 140

Gly Ile Arg Gln Phe Asn Val Lys Leu Val Lys Val Gln Ser Thr Trp
145                 150                 155                 160

Asp Glu Lys Tyr Thr Asp Ser Val Arg Phe Val Ser Arg Thr Ile Ala
                165                 170                 175

Tyr Cys Asn Ile Tyr Cys Leu Lys Lys Phe Leu Trp Leu Lys Asp Asp
                180                 185                 190

Asn Ala Ile Val Lys Phe Trp Lys Ser Val Thr Ile Gln Ser Gln Pro
            195                 200                 205

Arg Ile Gly Ala Val Asp Val Lys Leu Val Leu Asn Pro Arg Ala Phe
210                 215                 220

Ser Ala Glu Ile Arg Glu Gly Trp Glu Ile Tyr Arg Asp Glu Phe Trp
225                 230                 235                 240

Ala Arg Glu Gly Ala Arg Arg Lys Gln Ala His Glu Leu Arg Pro
                245                 250                 255

Lys Ser Glu

<210> SEQ ID NO 39
<211> LENGTH: 548
<212> TYPE: PRT
<213> ORGANISM: Saccharomyces cerevisiae

<400> SEQUENCE: 39

Met Tyr Phe Pro Phe Leu Gly Arg Leu Ser Ile Thr Asp Tyr Ile Ile
1               5                   10                  15

Val Val Leu Val Tyr Ile Glu Ser Ile Ile Ser Ser Val Leu Lys Leu
            20                  25                  30

Ile Pro Gln Pro Met Ile Asn Leu Phe Glu Trp Leu Ile Asn Phe Ser
            35                  40                  45
```

```
Thr Ser Ser Asp Asp Asn Thr Ile Glu Glu Lys Leu Arg Ser Ala Pro
    50                  55                  60

Thr Ile His Glu Met Cys Ala Ile Phe Asp Ile Ser Val Glu Asp His
65                  70                  75                  80

Leu Val Arg Thr Glu Asp Asn Tyr Ile Leu Thr Leu His Arg Ile Pro
                85                  90                  95

Pro Ile Ser Lys Asn Arg Phe Asn Asn Lys Val Val Tyr Leu His His
                100                 105                 110

Gly Leu Leu Met Cys Ser Asp Val Trp Cys Cys Asn Ile Glu Arg His
                115                 120                 125

Lys Asn Leu Pro Phe Val Leu His Asp Leu Gly Tyr Asp Val Trp Met
130                 135                 140

Gly Asn Asn Arg Gly Asn Lys Tyr Ser Thr Ala His Leu Asn Lys Pro
145                 150                 155                 160

Pro Lys Ser Asn Lys Phe Trp Asp Phe Ser Ile Asp Glu Phe Ala Phe
                165                 170                 175

Phe Asp Ile Pro Asn Ser Ile Glu Phe Ile Leu Asp Ile Thr Lys Val
                180                 185                 190

Asp Lys Val Ile Cys Ile Gly Phe Ser Gln Gly Ser Ala Gln Met Phe
                195                 200                 205

Ala Ala Phe Ser Leu Ser Glu Lys Leu Asn Arg Lys Val Ser His Phe
210                 215                 220

Ile Ala Ile Ala Pro Ala Met Thr Pro Lys Gly Leu His Asn Arg Ile
225                 230                 235                 240

Val Asp Thr Leu Ala Lys Ser Ser Pro Gly Phe Met Tyr Leu Phe Phe
                245                 250                 255

Gly Arg Lys Ile Val Leu Pro Ser Ala Val Ile Trp Gln Arg Thr Leu
                260                 265                 270

His Pro Thr Leu Phe Asn Leu Cys Ile Asp Ile Ala Asn Lys Ile Leu
            275                 280                 285

Phe Asn Trp Lys Ser Phe Asn Ile Leu Pro Arg Gln Lys Ile Ala Ser
290                 295                 300

Tyr Ala Lys Leu Tyr Ser Thr Thr Ser Val Lys Ser Ile Val His Trp
305                 310                 315                 320

Phe Gln Ile Leu Arg Ser Gln Lys Phe Gln Met Phe Glu Glu Ser Asp
                325                 330                 335

Asn Met Leu Asn Ser Leu Thr Arg Pro Tyr Gln Ile Ala Asn Phe Pro
                340                 345                 350

Thr Arg Thr Asn Ile Lys Ile Pro Ile Leu Leu Ile Tyr Gly Gly Ile
                355                 360                 365

Asp Ser Leu Val Asp Ile Asp Val Met Lys Lys Asn Leu Pro Phe Asn
370                 375                 380

Ser Val Phe Asp Val Lys Val Asp Asn Tyr Glu His Leu Asp Leu Ile
385                 390                 395                 400

Trp Gly Lys Asp Ala Asp Thr Leu Val Ile Ala Lys Val Leu Arg Phe
                405                 410                 415

Ile Glu Phe Phe Asn Pro Gly Asn Val Ser Val Lys Thr Asn Gln Leu
                420                 425                 430

Leu Pro Ser Ala Ser Leu Val Glu Glu Leu Pro Ser Thr Thr Trp Lys
            435                 440                 445

Thr Thr His Pro Thr His Gly Leu Ser Tyr Arg Thr His Ser Ala Asp
    450                 455                 460
```

```
Arg Ser Pro Leu Ser Val Gln Ala Asp Glu Ala Asp Glu Val His Asn
465                 470                 475                 480

Ala Asp Asn Ser Arg Phe Leu Arg Arg Val Phe Ser Thr Ser Ala Ile
                485                 490                 495

Asp Glu Asp Asn Glu Asn Glu His Gln Asp Asp Thr Glu Asp Gln Ile
            500                 505                 510

His Lys Glu Gln Gln Arg Arg Leu Ser Ala Tyr Leu Glu Ser Ser Lys
            515                 520                 525

Asp Leu Arg Gln Leu Asp Ala Asn Ser Ser Thr Thr Ala Leu Asp Ala
            530                 535                 540

Leu Asn Lys Glu
545

<210> SEQ ID NO 40
<211> LENGTH: 274
<212> TYPE: PRT
<213> ORGANISM: Saccharomyces cerevisiae

<400> SEQUENCE: 40

Met Ile Arg Gln Leu Asn Tyr Trp Ser Arg Lys Ala Tyr Leu Ile Tyr
1               5                   10                  15

Pro Phe Gln Val Phe Val Gly Ala Leu Leu Ser Ile Val Val Ser Ser
                20                  25                  30

Glu Thr Leu Asn His Gln Lys Glu Thr Cys Ala Leu Leu Lys Ser Ser
            35                  40                  45

Asn Ile Phe Asn Val Ile Phe Ala Tyr Lys Ala Asn Gln Leu Trp Pro
50                  55                  60

Phe Leu Phe Phe Ser Leu Ala Phe Leu Gln Ile Tyr Phe His Tyr Leu
65                  70                  75                  80

Ala Arg Met Asp Ile Leu Pro Leu Pro Ile Ser Ser Thr Glu Thr Ser
                85                  90                  95

Ser Ser Tyr Leu Thr Tyr Thr Asn His Trp Pro Leu Leu Lys Asn Arg
            100                 105                 110

Ile Ile Ser Ile Met Ile Thr Gln Tyr Ala Cys Lys Phe Val Leu Lys
            115                 120                 125

Tyr Leu Leu Leu Phe Leu Asn Phe Gln Phe Ile Asp His Val Phe Ile
130                 135                 140

Trp Thr Gly Gly Glu Cys Ser Ser Gly Ser Lys Thr Thr Ser Ala Glu
145                 150                 155                 160

Lys Cys Arg Leu Glu Asn Gly Lys Trp Asp Gly Gly Phe Asp Ile Ser
                165                 170                 175

Gly His Phe Cys Phe Leu Val Ser Ile Ser Met Ile Leu Trp Met Glu
            180                 185                 190

Leu His Leu Phe Ser Arg Phe Val Gln Ala Glu Asp Met Phe Trp Val
            195                 200                 205

Val Asn Lys Trp Val Arg Ala Cys Leu Ala Ile Val Cys Ala Val Leu
210                 215                 220

Val Ile Trp Ile Cys Ile Leu Trp Val Thr Ala Ile Tyr Tyr His Thr
225                 230                 235                 240

Ile Leu Glu Lys Val Leu Gly Cys Leu Met Gly Phe Ile Cys Pro Val
                245                 250                 255

Phe Ile Tyr His Ile Leu Pro Lys Ile Gly Ile Leu His Asn Tyr Leu
            260                 265                 270

Tyr Leu
```